United States Patent
Nakayama et al.

(10) Patent No.: US 10,513,561 B2
(45) Date of Patent: Dec. 24, 2019

(54) ANTI-MYL9 ANTIBODY

(71) Applicants: National University Corporation Chiba University, Chiba-shi, Chiba (JP); Eisai R&D Management Co., Ltd., Bunkyo-ku, Tokyo (JP)

(72) Inventors: Toshinori Nakayama, Chiba (JP); Motoko Kimura, Chiba (JP); Koji Hayashizaki, Chiba (JP); Toshifumi Hirayama, Kobe (JP); Jungo Kakuta, Kobe (JP); Yoshimasa Sakamoto, Kobe (JP); Ryu Gejima, Kobe (JP); Daisuke Tokita, Kobe (JP); Kenzo Muramoto, Kobe (JP); Toshio Imai, Kobe (JP)

(73) Assignees: National University Corporation Chiba University, Chiba (JP); Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 16/063,515

(22) PCT Filed: Jan. 11, 2017

(86) PCT No.: PCT/JP2017/000605
§ 371 (c)(1),
(2) Date: Jun. 18, 2018

(87) PCT Pub. No.: WO2017/122666
PCT Pub. Date: Jul. 20, 2017

(65) Prior Publication Data
US 2019/0002588 A1  Jan. 3, 2019

(30) Foreign Application Priority Data
Jan. 12, 2016 (JP) .................... 2016-003429

(51) Int. Cl.
*A61K 39/395* (2006.01)
*A61P 37/08* (2006.01)
*A61P 37/02* (2006.01)
*A61P 35/00* (2006.01)
*A61P 1/00* (2006.01)
*C07K 16/18* (2006.01)
*C07K 16/46* (2006.01)
*A61P 11/00* (2006.01)
*A61P 1/04* (2006.01)
*C07K 16/28* (2006.01)
*C07K 14/47* (2006.01)
*C12N 15/09* (2006.01)

(52) U.S. Cl.
CPC ............ *C07K 16/46* (2013.01); *A61K 39/395* (2013.01); *A61K 39/3955* (2013.01); *A61P 1/04* (2018.01); *A61P 11/00* (2018.01); *A61P 35/00* (2018.01); *A61P 37/02* (2018.01); *A61P 37/08* (2018.01); *C07K 16/18* (2013.01); *C07K 16/2803* (2013.01); *C07K 14/4716* (2013.01); *C12N 15/09* (2013.01)

(58) Field of Classification Search
None
See application file for complete search history.

(56) References Cited

U.S. PATENT DOCUMENTS

| | | | |
|---|---|---|---|
| 2010/0093789 A1 | 4/2010 | Yamada et al. | |
| 2012/0087927 A1 | 4/2012 | Matsushima et al. | |
| 2016/0102139 A1 | 4/2016 | Nakayama et al. | |
| 2016/0145332 A1 | 5/2016 | Mackay et al. | |

FOREIGN PATENT DOCUMENTS

| | | |
|---|---|---|
| JP | 2009-508812 | 3/2019 |
| WO | WO 2007/019563 | 2/2007 |
| WO | WO 2008/105058 | 9/2008 |
| WO | WO 2010/123012 | 10/2010 |
| WO | WO 2014/192915 | 4/2014 |
| WO | WO 2014/205501 | 12/2014 |
| WO | WO 2015/190538 | 12/2018 |

OTHER PUBLICATIONS

International Preliminary Report on Patentability in International No. PCT/JP2017/000605, dated Jul. 17, 2018, 9 pages (English Translation).
International Search Report in International Application No. PCT/JP2017/000605, dated Feb. 28, 2017, 2 pages (English Translation).
Ishihara et al., "Irradiation-tolerant lung cancer cells acquire invasive ability dependent on dephosphorylation of the myosin regulatory light chain," FEBS Letters, 587, 2013, p. 732-p. 736.
Luo et al., "Histone methyltransferase SMYD3 promotes MRTF-A-mediated transactivation of MYL9 and migration of MCF-7 breast cancer cells," Cancer Letters, 344, 2014, p. 129-p. 137.
Miki-Hosokawa et al., "CD69 Controls the Pathogenesis of Allergic Airway Inflammation," J. Immunol., 183, 2009, p. 8203-p. 8215.
Murata et al., "CD69-null mice protected from arthritis induced with anti-type II collagen antibodies," Int. Immunol., 15, 2003, p. 987-p. 992.
Testi et al., "The CD69 receptor: a multipurpose cell-surface trigger for hematopoietic cells," Immunol. Today, 15, 1994, p. 479-p. 483.
Benjamini's Immunology a Short Course, 2nd ed., Department of Medical Microbiology and Immunology School of Medicine, Wiley-Liss, Inc., 1991, p. 40.

(Continued)

*Primary Examiner* — Zachary C Howard
(74) *Attorney, Agent, or Firm* — Fish & Richardson P.C.

(57) ABSTRACT

The present invention provides an anti-Myl9 antibody or a Myl9 binding fragment thereof that binds to Myl9 and may inhibit the interaction between Myl9 and CD69 in humans, as well as a pharmaceutical composition comprising the same. A mouse anti-human/mouse Myl9 monoclonal antibody having binding affinity against Myl9 was obtained, and the sequence for the complementarity determining region (CDR) of said mouse anti-human/mouse Myl9 monoclonal antibody was identified. Accordingly, a humanized antibody comprising the CDR sequence of said mouse anti-human/mouse Myl9 monoclonal antibody in the variable region of heavy and light chains was produced.

31 Claims, 29 Drawing Sheets
Specification includes a Sequence Listing.

(56) References Cited

OTHER PUBLICATIONS

European Extended Search Report in European Patent Application No. 14805019.8, dated Feb. 1, 2017, 5 pages.

Ferrara et al., "Recombinant Renewable Polyclonal Antibodies," mAbs, 2015, 7(1):32-41.

Hayashizaki et al, "Myosin light chains 9 and 12 are functional ligands for CD69 that regulate airway inflammation," Science Immunology, 2016, 1.eaaf9154, XP055335879.

Ikegaki, "Novel Protein Kinase Inhibitor: FASUDIL Pharmacological Effects on Cerebral Vasospasm following Subarachnoid Hemorrhage," Brain 21, 2000, 3(4):453-456 (with English Translation).

International Search Report and Written Opinion in International Patent Application No. PCT/JP2014/064399, dated Aug. 5, 2014, 12 pages (English Translation).

Office Action in Japanese Patent Application No. 2015-519959, dated Feb. 13, 2018, 8 pages (with English Translation).

Office Action in U.S. Appl. No. 14/893,122, dated Apr. 10, 2017, 9 pages.

Office Action in U.S. Appl. No. 14/893,122, dated Sep. 13, 2016, 13 pages.

Office Action in U.S. Appl. No. 15/667,644, dated Mar. 14, 2018, 14 pages.

Office Action in U.S. Appl. No. 16/122,903, dated May 9, 2019, 12 pages.

O'Hara et al, "Cholangiocyte Myosin IIB Is Required for Localized Aggregation of Sodium Glucose Cotransporter 1 to Sites of Cryptosporidium parvum Cellular Invasion and Facilitates Parasite Internalization," Infection and Immunity, 2010, 78(7):2927-p. 2936.

Park et al, "Myosin regulatory light chains are required to maintain the stability of myosin II and cellular integrity," Biochemical Journal, 2011, 434:171-184, XP055337479.

scbt.com [online], "Datasheet for sc-19849-R," [retrieved on Jul. 22, 2019], retrieved from: URL<http://datasheets.scbt.com/sc-19849.pdf>, 1 page.

Xu et al, ""Nonmuscle myosin light-chain kinase mediates neutrophil transmigration in sepsis-induced lung inflammation by activating $\beta 2$ integrins,"" Nat Immunol, 2008, 9(8): 880-886.

European Extended Search Report in European Patent Application No. 17738420.3, dated Jul. 8, 2019, 5 pages.

Huang et al., "Decreased expression of myosin light chain MYL9 in stroma predicts malignant progression and poor biochemical recurrence-free survival in prostate cancer," Medical Oncology, 2014, 31(1):820, 9 pages.

Office Action in Israeli Patent Application No. 260083, dated Sep. 22, 2019, 5 pages (with English Translation).

SEQUENCE LISTING

```
<160> NUMBER OF SEQ ID NOS: 97

<210> SEQ ID NO 1
<211> LENGTH: 172
<212> TYPE: PRT
<213> ORGANISM: Mus musculus

<400> SEQUENCE: 1

Met Ser Ser Lys Arg Ala Lys Ala Lys Thr Thr Lys Lys Arg Pro Gln
1               5                   10                  15

Arg Ala Thr Ser Asn Val Phe Ala Met Phe Asp Gln Ser Gln Ile Gln
            20                  25                  30

Glu Phe Lys Glu Ala Phe Asn Met Ile Asp Gln Asn Arg Asp Gly Phe
        35                  40                  45

Ile Asp Lys Glu Asp Leu His Asp Met Leu Ala Ser Leu Gly Lys Asn
    50                  55                  60

Pro Thr Asp Glu Tyr Leu Glu Gly Met Met Asn Glu Ala Pro Gly Pro
```

```
                65                  70                  75                  80
Ile Asn Phe Thr Met Phe Leu Thr Met Phe Gly Glu Lys Leu Asn Gly
                    85                  90                  95

Thr Asp Pro Glu Asp Val Ile Arg Asn Ala Phe Ala Cys Phe Asp Glu
                100                 105                 110

Glu Ala Ser Gly Phe Ile His Glu Asp His Leu Arg Glu Leu Leu Thr
                115                 120                 125

Thr Met Gly Asp Arg Phe Thr Asp Glu Glu Val Asp Glu Met Tyr Arg
            130                 135                 140

Glu Ala Pro Ile Asp Lys Lys Gly Asn Phe Asn Tyr Val Glu Phe Thr
145                 150                 155                 160

Arg Ile Leu Lys His Gly Ala Lys Asp Lys Asp
                165                 170

<210> SEQ ID NO 2
<211> LENGTH: 172
<212> TYPE: PRT
<213> ORGANISM: Homo sapiens

<400> SEQUENCE: 2

Met Ser Ser Lys Arg Ala Lys Ala Lys Thr Thr Lys Lys Arg Pro Gln
1               5                   10                  15

Arg Ala Thr Ser Asn Val Phe Ala Met Phe Asp Gln Ser Gln Ile Gln
                20                  25                  30

Glu Phe Lys Glu Ala Phe Asn Met Ile Asp Gln Asn Arg Asp Gly Phe
            35                  40                  45

Ile Asp Lys Glu Asp Leu His Asp Met Leu Ala Ser Leu Gly Lys Asn
50                  55                  60

Pro Thr Asp Glu Tyr Leu Glu Gly Met Met Ser Glu Ala Pro Gly Pro
65                  70                  75                  80

Ile Asn Phe Thr Met Phe Leu Thr Met Phe Gly Glu Lys Leu Asn Gly
                    85                  90                  95

Thr Asp Pro Glu Asp Val Ile Arg Asn Ala Phe Ala Cys Phe Asp Glu
                100                 105                 110

Glu Ala Ser Gly Phe Ile His Glu Asp His Leu Arg Glu Leu Leu Thr
                115                 120                 125

Thr Met Gly Asp Arg Phe Thr Asp Glu Glu Val Asp Glu Met Tyr Arg
            130                 135                 140

Glu Ala Pro Ile Asp Lys Lys Gly Asn Phe Asn Tyr Val Glu Phe Thr
145                 150                 155                 160

Arg Ile Leu Lys His Gly Ala Lys Asp Lys Asp
                165                 170

<210> SEQ ID NO 3
<211> LENGTH: 28
<212> TYPE: PRT
<213> ORGANISM: Homo sapiens

<400> SEQUENCE: 3

Met Ser Ser Lys Arg Ala Lys Ala Lys Thr Thr Lys Lys Arg Pro Gln
1               5                   10                  15

Arg Ala Thr Ser Asn Val Phe Ala Met Phe Asp Cys
                20                  25

<210> SEQ ID NO 4
<211> LENGTH: 138
<212> TYPE: PRT
```

-continued

<213> ORGANISM: Mus musculus

<400> SEQUENCE: 4

| | | | | | | | | | | | | | | | |
|---|---|---|---|---|---|---|---|---|---|---|---|---|---|---|---|
| Asn | Val | Gly | Lys | Tyr | Asn | Cys | Pro | Gly | Leu | Tyr | Glu | Lys | Leu | Glu | Ser |
| 1 | | | | 5 | | | | | 10 | | | | | 15 | |
| Ser | Asp | His | His | Val | Ala | Thr | Cys | Lys | Asn | Glu | Trp | Ile | Ser | Tyr | Lys |
| | | | 20 | | | | | 25 | | | | | 30 | | |
| Arg | Thr | Cys | Tyr | Phe | Phe | Ser | Thr | Thr | Thr | Lys | Ser | Trp | Ala | Leu | Ala |
| | | 35 | | | | | 40 | | | | | 45 | | | |
| Gln | Arg | Ser | Cys | Ser | Glu | Asp | Ala | Ala | Thr | Leu | Ala | Val | Ile | Asp | Ser |
| | 50 | | | | | 55 | | | | | 60 | | | | |
| Glu | Lys | Asp | Met | Thr | Phe | Leu | Lys | Arg | Tyr | Ser | Gly | Glu | Leu | Glu | His |
| 65 | | | | | 70 | | | | | 75 | | | | | 80 |
| Trp | Ile | Gly | Leu | Lys | Asn | Glu | Ala | Asn | Gln | Thr | Trp | Lys | Trp | Ala | Asn |
| | | | | 85 | | | | | 90 | | | | | 95 | |
| Gly | Lys | Glu | Phe | Asn | Ser | Trp | Phe | Asn | Leu | Thr | Gly | Ser | Gly | Arg | Cys |
| | | | 100 | | | | | 105 | | | | | 110 | | |
| Val | Ser | Val | Asn | His | Lys | Asn | Val | Thr | Ala | Val | Asp | Cys | Glu | Ala | Asn |
| | | 115 | | | | | 120 | | | | | 125 | | | |
| Phe | His | Trp | Val | Cys | Ser | Lys | Pro | Ser | Arg | | | | | | |
| | 130 | | | | | 135 | | | | | | | | | |

<210> SEQ ID NO 5
<211> LENGTH: 204
<212> TYPE: PRT
<213> ORGANISM: Mus musculus

<400> SEQUENCE: 5

| | | | | | | | | | | | | | | | |
|---|---|---|---|---|---|---|---|---|---|---|---|---|---|---|---|
| Met | Ala | Pro | Lys | Lys | Pro | Glu | Pro | Lys | Lys | Asp | Asp | Ala | Lys | Ala | Ala |
| 1 | | | | 5 | | | | | 10 | | | | | 15 | |
| Ala | Pro | Lys | Ala | Ala | Pro | Ala | Pro | Ala | Ala | Ala | Pro | Ala | Ala | Ala | Pro |
| | | | 20 | | | | | 25 | | | | | 30 | | |
| Ala | Ala | Ala | Pro | Glu | Pro | Glu | Arg | Pro | Lys | Glu | Ala | Glu | Phe | Asp | Ala |
| | | 35 | | | | | 40 | | | | | 45 | | | |
| Ser | Lys | Ile | Lys | Ile | Glu | Phe | Thr | Pro | Glu | Gln | Ile | Glu | Glu | Phe | Lys |
| | 50 | | | | | 55 | | | | | 60 | | | | |
| Glu | Ala | Phe | Leu | Leu | Phe | Asp | Arg | Thr | Pro | Lys | Gly | Glu | Met | Lys | Ile |
| 65 | | | | | 70 | | | | | 75 | | | | | 80 |
| Thr | Tyr | Gly | Gln | Cys | Gly | Asp | Val | Leu | Arg | Ala | Leu | Gly | Gln | Asn | Pro |
| | | | | 85 | | | | | 90 | | | | | 95 | |
| Thr | Gln | Ala | Glu | Val | Leu | Arg | Val | Leu | Gly | Lys | Pro | Lys | Gln | Glu | Glu |
| | | | 100 | | | | | 105 | | | | | 110 | | |
| Leu | Asn | Ser | Lys | Met | Met | Asp | Phe | Glu | Thr | Phe | Leu | Pro | Met | Leu | Gln |
| | | 115 | | | | | 120 | | | | | 125 | | | |
| His | Ile | Ser | Lys | Asn | Lys | Asp | Thr | Gly | Thr | Tyr | Glu | Asp | Phe | Val | Glu |
| | 130 | | | | | 135 | | | | | 140 | | | | |
| Gly | Leu | Arg | Val | Phe | Asp | Lys | Glu | Gly | Asn | Gly | Thr | Val | Met | Gly | Ala |
| 145 | | | | | 150 | | | | | 155 | | | | | 160 |
| Glu | Leu | Arg | His | Val | Leu | Ala | Thr | Leu | Gly | Glu | Arg | Leu | Thr | Glu | Asp |
| | | | | 165 | | | | | 170 | | | | | 175 | |
| Glu | Val | Glu | Lys | Leu | Met | Ala | Gly | Gln | Glu | Asp | Ser | Asn | Gly | Cys | Ile |
| | | | 180 | | | | | 185 | | | | | 190 | | |
| Asn | Tyr | Glu | Ala | Phe | Val | Lys | His | Ile | Met | Ala | Ser | | | | |
| | | | 195 | | | | | 200 | | | | | | | |

<210> SEQ ID NO 6
<211> LENGTH: 195
<212> TYPE: PRT
<213> ORGANISM: Homo sapiens

<400> SEQUENCE: 6

Met Ala Pro Lys Lys Pro Glu Pro Lys Lys Asp Asp Ala Lys Ala Ala
1               5                   10                  15

Pro Lys Ala Ala Pro Ala Pro Ala Pro Pro Glu Pro Glu Arg Pro
            20                  25                  30

Lys Glu Val Glu Phe Asp Ala Ser Lys Ile Lys Ile Glu Phe Thr Pro
        35                  40                  45

Glu Gln Ile Glu Glu Phe Lys Glu Ala Phe Met Leu Phe Asp Arg Thr
    50                  55                  60

Pro Lys Cys Glu Met Lys Ile Thr Tyr Gly Gln Cys Gly Asp Val Leu
65                  70                  75                  80

Arg Ala Leu Gly Gln Asn Pro Thr Gln Ala Glu Val Leu Arg Val Leu
                85                  90                  95

Gly Lys Pro Arg Gln Glu Glu Leu Asn Thr Lys Met Met Asp Phe Glu
            100                 105                 110

Thr Phe Leu Pro Met Leu Gln His Ile Ser Lys Asn Lys Asp Thr Gly
        115                 120                 125

Thr Tyr Glu Asp Phe Val Glu Gly Leu Arg Val Phe Asp Lys Glu Gly
    130                 135                 140

Asn Gly Thr Val Met Gly Ala Glu Leu Arg His Val Leu Ala Thr Leu
145                 150                 155                 160

Gly Glu Arg Leu Thr Glu Asp Glu Val Glu Lys Leu Met Ala Gly Gln
                165                 170                 175

Glu Asp Ser Asn Gly Cys Ile Asn Tyr Glu Ala Phe Val Lys His Ile
            180                 185                 190

Met Ser Ser
        195

<210> SEQ ID NO 7
<211> LENGTH: 12
<212> TYPE: DNA
<213> ORGANISM: Artificial Sequence
<220> FEATURE:
<223> OTHER INFORMATION: Synthetic primer

<400> SEQUENCE: 7
acatcactcc gt                                                           12

<210> SEQ ID NO 8
<211> LENGTH: 50
<212> TYPE: DNA
<213> ORGANISM: Artificial Sequence
<220> FEATURE:
<223> OTHER INFORMATION: Synthetic primer

<400> SEQUENCE: 8
acggagtgat gtccgtcgac gtatctctgc gttgatactt cagcgtagct                  50

<210> SEQ ID NO 9
<211> LENGTH: 26
<212> TYPE: DNA
<213> ORGANISM: Artificial Sequence
<220> FEATURE:
<223> OTHER INFORMATION: Synthetic primer

<400> SEQUENCE: 9

-continued agctacgctg aagtatcaac gcagag                                                        26

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
gccagtggat agactgatgg                                                               20

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
gatggataca gttggtgcag c                                                             21

<210> SEQ ID NO 12
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 12

Met Glu Trp Ser Trp Val Phe Leu Phe Leu Leu Ser Val Ile Ala Gly
1               5                   10                  15

Val Gln Ser

<210> SEQ ID NO 13
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 13

Gln Val Gln Leu Gln Gln Ser Gly Ala Glu Val Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Thr Asp Tyr Asp Tyr Asp Gly Phe Ala Tyr Trp Gly Gln Gly Thr Leu
            100                 105                 110

Val Thr Val Ser Ala
        115

<210> SEQ ID NO 14
<211> LENGTH: 19

<212> TYPE: PRT
<213> ORGANISM: Artificial Sequence
<220> FEATURE:
<223> OTHER INFORMATION: Synthetic polypeptide

<400> SEQUENCE: 14

Met Lys Leu Pro Val Arg Leu Leu Val Leu Met Phe Trp Ile Pro Ala
1               5                   10                  15

Ser Ser Ser

<210> SEQ ID NO 15
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 15

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Arg Ser
        35                  40                  45

Pro Lys Leu Leu Ile Ser Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Thr Arg Val Glu Ala Glu Asp Leu Gly Val Tyr Phe Cys Ser Gln Asn
                85                  90                  95

Thr His Val Pro Pro Leu Thr Phe Gly Ala Gly Thr Lys Leu Glu Leu
            100                 105                 110

Lys

<210> SEQ ID NO 16
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 16
atggaatgga gctgggtctt tctcttcctc ctgtcagtaa ttgcaggtgt ccaatcc       57

<210> SEQ ID NO 17
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 17
caggttcaac tgcagcagtc tggggctgag gtggtgaggc ctggggcttc agtgacgctg       60
tcctgcaagg cttcgggcta cacatttact gactatgaaa tgcactgggt gaagcagaca      120
cctgtgcatg gcctggaatg gattggagct attgatcctg aaactggtgg tactgcctac      180
aatcagaagt tcaagggcaa ggccatactg actgcagaca atcctccaa cacagcctac       240 atggagctcc gcagcctgac atctgaggac tctgccgtct attactgtac agactatgat      300
tacgacgggt tgcttactg gggccaaggg actctggtca ctgtctctgc a               351

<210> SEQ ID NO 18
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 18
atgaagttgc ctgttaggct gttggtgctg atgttctgga ttcctgcttc cagcagt    57

<210> SEQ ID NO 19
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 19
gatgttgtga tgacccaaac tccactctcc ctgcctgtca gtcttggaga tcaagcctcc    60
atctcttgca gatctagtca gagccttgta cacagtaatg aaacaccta tttacattgg   120 tacctgcaga agccaggccg gtctccaaag ctcctgatct ccaaagtttc caaccgattt   180
tctggggtcc cagacaggtt cagtggcagt ggatcaggga cagatttcac actcaagatc   240
accagagtgg aggctgagga tctgggagtt tatttctgct ctcaaaatac acatgttcct   300
ccgctcacgt tcggtgctgg gaccaagctg gagctgaaa                          339

<210> SEQ ID NO 20
<211> LENGTH: 40
<212> TYPE: DNA
<213> ORGANISM: Artificial Sequence
<220> FEATURE:
<223> OTHER INFORMATION: Synthetic primer

<400> SEQUENCE: 20
gcgaagcttg ccgccaccat ggaatggagc tgggtctttc                         40

<210> SEQ ID NO 21
<211> LENGTH: 39
<212> TYPE: DNA
<213> ORGANISM: Artificial Sequence
<220> FEATURE:
<223> OTHER INFORMATION: Synthetic primer

<400> SEQUENCE: 21
gcgaagcttg ccgccaccat gaagttgcct gttaggctg                          39

<210> SEQ ID NO 22
<211> LENGTH: 36
<212> TYPE: DNA
<213> ORGANISM: Artificial Sequence
<220> FEATURE:
<223> OTHER INFORMATION: Synthetic primer

<400> SEQUENCE: 22
gcggaattca tcatttaccc agagaccggg agatgg                             36

<210> SEQ ID NO 23
<211> LENGTH: 40
<212> TYPE: DNA
<213> ORGANISM: Artificial Sequence
<220> FEATURE:
<223> OTHER INFORMATION: Synthetic primer

<400> SEQUENCE: 23
gcggaattca ctaacactca ttcctgttga agctcttgac 40

<210> SEQ ID NO 24
<211> LENGTH: 335
<212> TYPE: PRT
<213> ORGANISM: Artificial Sequence
<220> FEATURE:
<223> OTHER INFORMATION: Synthetic polypeptide

<400> SEQUENCE: 24

```
Ala Lys Thr Thr Ala Pro Ser Val Tyr Pro Leu Ala Pro Val Cys Gly
 1               5                  10                  15

Gly Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Leu Leu Gln Ser Gly Leu Tyr Thr Leu
    50                  55                  60

Ser Ser Ser Val Thr Val Thr Ser Asn Thr Trp Pro Ser Gln Thr Ile
65                  70                  75                  80

Thr Cys Asn Val Ala His Pro Ala Ser Ser Thr Lys Val Asp Lys Lys
                85                  90                  95

Ile Glu Pro Arg Val Pro Ile Thr Gln Asn Pro Cys Pro Pro Leu Lys
            100                 105                 110

Glu Cys Pro Pro Cys Ala Ala Pro Asp Leu Leu Gly Gly Pro Ser Val
        115                 120                 125

Phe Ile Phe Pro Pro Lys Ile Lys Asp Val Leu Met Ile Ser Leu Ser
    130                 135                 140

Pro Met Val Thr Cys Val Val Asp Val Ser Glu Asp Asp Pro Asp
145                 150                 155                 160

Val Gln Ile Ser Trp Phe Val Asn Asn Val Glu Val His Thr Ala Gln
                165                 170                 175

Thr Gln Thr His Arg Glu Asp Tyr Asn Ser Thr Leu Arg Val Val Ser
            180                 185                 190

Ala Leu Pro Ile Gln His Gln Asp Trp Met Ser Gly Lys Glu Phe Lys
        195                 200                 205

Cys Lys Val Asn Asn Arg Ala Leu Pro Ser Pro Ile Glu Lys Thr Ile
    210                 215                 220

Ser Lys Pro Arg Gly Pro Val Arg Ala Pro Gln Val Tyr Val Leu Pro
225                 230                 235                 240

Pro Pro Ala Glu Glu Met Thr Lys Lys Glu Phe Ser Leu Thr Cys Met
                245                 250                 255

Ile Thr Gly Phe Leu Pro Ala Glu Ile Ala Val Asp Trp Thr Ser Asn
            260                 265                 270

Gly Arg Thr Glu Gln Asn Tyr Lys Asn Thr Ala Thr Val Leu Asp Ser
        275                 280                 285

Asp Gly Ser Tyr Phe Met Tyr Ser Lys Leu Arg Val Gln Lys Ser Thr
    290                 295                 300

Trp Glu Arg Gly Ser Leu Phe Ala Cys Ser Val Val His Glu Gly Leu
305                 310                 315                 320

His Asn His Leu Thr Thr Lys Thr Ile Ser Arg Ser Leu Gly Lys
                325                 330                 335
```

<210> SEQ ID NO 25
<211> LENGTH: 107

```
<212> TYPE: PRT
<213> ORGANISM: Artificial Sequence
<220> FEATURE:
<223> OTHER INFORMATION: Synthetic polypeptide

<400> SEQUENCE: 25

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 26
<211> LENGTH: 1008
<212> TYPE: DNA
<213> ORGANISM: Artificial Sequence
<220> FEATURE:
<223> OTHER INFORMATION: Synthetic polynucleotide

<400> SEQUENCE: 26
gccaaaacaa cagccccatc ggtctatcca ctggcccctg tgtgtggagg tacaactggc     60
tcctcggtga ctctaggatg cctggtcaag ggttatttcc ctgagccagt gaccttgacc    120
tggaactctg gatccctgtc cagtggtgtg cacaccttcc cagctctcct gcagtctggc    180
ctctacaccc tcagcagctc agtgactgta acctcgaaca cctggcccag ccagaccatc    240
acctgcaatg tggcccaccc ggcaagcagc accaaagtgg acaagaaaat tgagcccaga    300
gtgcccataa cacagaaccc ctgtcctcca ctcaaagagt gtccccccatg cgcagctcca    360
gacctcttgg gtggaccatc cgtcttcatc ttccctccaa agatcaagga tgtactcatg    420
atctccctga gccccatggt cacatgtgtg gtggtggatg tgagcgagga tgacccagac    480
gtccagatca gctggttgt gaacaacgtg aagtacaca cagctcagac acaaacccat    540
agagaggatt acaacagtac tctccgggtg gtcagtgccc tccccatcca gcaccaggac    600
tggatgagtg gcaaggagtt caaatgcaag gtcaacaaca gagccctccc atcccccatc    660
gagaaaacca tctcaaaacc cagagggcca gtaagagctc cacaggtata tgtcttgcct    720
ccaccagcag aagagatgac taagaaagag ttcagtctga cctgcatgat cacaggcttc    780
ttacctgccg aaattgctgt ggactggacc agcaatgggc gtacagagca aaactacaag    840
aacaccgcaa cagtcctgga ctctgatggt tcctacttca tgtacagcaa gctcagagta    900
caaaagagca cttgggaaag aggaagtctt ttcgcctgct cagtggtcca cgagggtctg    960
cacaatcacc ttacgactaa gaccatctcc cggtctctgg gtaaatga              1008

<210> SEQ ID NO 27
<211> LENGTH: 324
<212> TYPE: DNA
<213> ORGANISM: Artificial Sequence
<220> FEATURE:
<223> OTHER INFORMATION: Synthetic polynucleotide
```

-continued

<400> SEQUENCE: 27

```
cgggctgatg ctgcaccaac tgtatccatc ttcccaccat ccagtgagca gttaacatct    60
ggaggtgcct cagtcgtgtg cttcttgaac aacttctacc ccaaagacat caatgtcaag   120
tggaagattg atggcagtga acgacaaaat ggcgtcctga acagttggac tgatcaggac   180
agcaaagaca gcacctacag catgagcagc accctcacgt tgaccaagga cgagtatgaa   240
cgacataaca gctatacctg tgaggccact cacaagacat caacttcacc cattgtcaag   300
agcttcaaca ggaatgagtg ttag                                          324
```

<210> SEQ ID NO 28
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 28

```
Asp Tyr Glu Met His
1               5
```

<210> SEQ ID NO 29
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 29

```
Gly Tyr Thr Phe Thr Asp Tyr Glu Met His
1               5                   10
```

<210> SEQ ID NO 30
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 30

```
Ala Ile Asp Pro Glu Thr Gly Gly Thr Ala Tyr Asn Gln Lys Phe Lys
1               5                   10                  15

Gly
```

<210> SEQ ID NO 31
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 31

```
Ala Ile Asp Pro Glu Thr Gly Gly Thr Ala
1               5                   10
```

<210> SEQ ID NO 32
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 32

Tyr Asp Tyr Asp Gly Phe Ala Tyr
1               5

<210> SEQ ID NO 33
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 33

Arg Ser Ser Gln Ser Leu Val His Ser Asn Gly Asn Thr Tyr Leu His
1               5                   10                  15

<210> SEQ ID NO 34
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 34

Lys Val Ser Asn Arg Phe Ser
1               5

<210> SEQ ID NO 35
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 35

Ser Gln Asn Thr His Val Pro Pro Leu Thr
1               5                   10

<210> SEQ ID NO 36
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 36
gactatgaaa tgcac                                                         15

<210> SEQ ID NO 37
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 37
ggctacacat ttactgacta tgaaatgcac                                         30

<210> SEQ ID NO 38
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 38
gctattgatc ctgaaactgg tggtactgcc tacaatcaga gttcaagggc                   51

```
<210> SEQ ID NO 39
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 39
gctattgatc ctgaaactgg tggtactgcc                                    30

<210> SEQ ID NO 40
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 40
tatgattacg acgggtttgc ttac                                          24

<210> SEQ ID NO 41
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 41
agatctagtc agagccttgt acacagtaat ggaaacacct atttacat                48

<210> SEQ ID NO 42
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 42
aaagtttcca accgattttc t                                             21

<210> SEQ ID NO 43
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 43
tctcaaaata cacatgttcc tccgctcacg                                    30

<210> SEQ ID NO 44
<211> LENGTH: 325
<212> TYPE: PRT
<213> ORGANISM: Artificial Sequence
<220> FEATURE:
<223> OTHER INFORMATION: Synthetic polypeptide

<400> SEQUENCE: 44

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
            50                  55                  60
Leu Ser Ser Val Val Thr Val Pro Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
                115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
                195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 45
<211> LENGTH: 978
<212> TYPE: DNA
<213> ORGANISM: Artificial Sequence
<220> FEATURE:
<223> OTHER INFORMATION: Synthetic polynucleotide

<400> SEQUENCE: 45
gctagcacaa aaggcccctc tgtcttccct ctggctccct gctcccgctc cacctccgag      60
tccactgccg ctctgggctg tctggtcaag gattacttcc ctgagccagt cactgtgagt     120
tggaactcag gcgccctgac cagcggagtc cacacatttc ccgctgtgct gcagagctcc     180
ggcctgtact ccctgtctag tgtggtcacc gtgccttcaa gcaatttcgg gactcagacc     240
tatacatgca acgtggacca taagccatct aatactaagg tcgataaaac cgtggagcga     300
aaatgctgcg tggaatgccc accttgtcct gctccaccag ccgctgcacc aagcgtgttc     360
ctgtttcctc caaagcccaa agacacactg atgatcagca gaactcctga ggtcacctgc     420
gtggtcgtgg acgtgtccca cgaggatccc gaagtccagt ttaactggta cgtggatggg     480
```

```
gtcgaagtgc ataatgcaaa gactaaacct cgggaggaac agttcaactc tacctttaga      540
gtcgtgagtg tgctgacagt cgtgcaccag gactggctga acggaaagga gtataagtgc      600
aaagtgtcta ataagggcct gcccgcccct atcgagaaaa caattagtaa gactaaaggc      660
cagccaaggg aaccccaggt gtacacactg cccctagtc gcgaggaaat gacaaagaac       720
caggtctcac tgacttgtct ggtgaaaggg ttctatccat ccgacattgc cgtggagtgg      780
gaatctaatg gacagcccga aaacaattac aagaccacac cacccatgct ggacagcgat     840
ggatccttct ttctgtattc aaagctgacc gtggataaaa gccggtggca gcagggcaat      900 gtctttcct gctctgtgat gcacgaagcc ctgcacaacc actacactca gaagtccctg       960
tccctgtctc ctggctga                                                    978
```

<210> SEQ ID NO 46
<211> LENGTH: 107
<212> TYPE: PRT
<213> ORGANISM: Homo sapiens

<400> SEQUENCE: 46

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 47
<211> LENGTH: 324
<212> TYPE: DNA
<213> ORGANISM: Homo sapiens

<400> SEQUENCE: 47

```
cgtacggtcg ccgcccctc cgtgtttatt tttcctccat ctgacgaaca gctgaagagt       60
gggaccgcct ccgtggtgtg cctgctgaac aatttctacc cccgggaggc caaggtgcag     120
tggaaagtcg acaacgctct gcagtctggc aatagtcagg agtcagtgac tgaacaggac     180
agcaaggatt ccacctattc tctgagctcc accctgacac tgagcaaagc agattacgaa    240
aagcacaaag tctatgcctg cgaagtgacc caccagggc tgagcagtcc agtgaccaag     300 tccttaaca ggggagagtg ttga                                              324
```

<210> SEQ ID NO 48
<211> LENGTH: 101
<212> TYPE: PRT
<213> ORGANISM: Artificial Sequence
<220> FEATURE:
<223> OTHER INFORMATION: Synthetic polypeptide

<400> SEQUENCE: 48

```
Asp Ile Val Met Thr Gln Ser Pro Leu Ser Leu Pro Val Thr Pro Gly
1               5                   10                  15
```

```
Glu Pro Ala Ser Ile Ser Cys Arg Ser Ser Gln Ser Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro
            100

<210> SEQ ID NO 49
<211> LENGTH: 100
<212> TYPE: PRT
<213> ORGANISM: Artificial Sequence
<220> FEATURE:
<223> OTHER INFORMATION: Synthetic polypeptide

<400> SEQUENCE: 49

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro
            100

<210> SEQ ID NO 50
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 50

Leu Thr Phe Gly Gly Gly Thr Lys Val Glu Ile Lys
1               5                   10

<210> SEQ ID NO 51
<211> LENGTH: 98
<212> TYPE: PRT
<213> ORGANISM: Artificial Sequence
<220> FEATURE:
<223> OTHER INFORMATION: Synthetic polypeptide

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

```
Thr Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg
```

<210> SEQ ID NO 52
<211> LENGTH: 98
<212> TYPE: PRT
<213> ORGANISM: Artificial Sequence
<220> FEATURE:
<223> OTHER INFORMATION: Synthetic polypeptide

<400> SEQUENCE: 52

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg
```

<210> SEQ ID NO 53
<211> LENGTH: 98
<212> TYPE: PRT
<213> ORGANISM: Artificial Sequence
<220> FEATURE:
<223> OTHER INFORMATION: Synthetic polypeptide

<400> SEQUENCE: 53

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Ser Tyr
             20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
 50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg
```

<210> SEQ ID NO 54
<211> LENGTH: 15
<212> TYPE: PRT
<213> ORGANISM: Artificial Sequence

```
<220> FEATURE:
<223> OTHER INFORMATION: Synthetic polypeptide

<400> SEQUENCE: 54

Tyr Phe Asp Tyr Trp Gly Gln Gly Thr Leu Val Thr Val Ser Ser
1               5                   10                  15

<210> SEQ ID NO 55
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Glu Met His Trp Val Arg Gln Ala Pro Gly Gln Gly Leu Glu Trp Met
        35                  40                  45

Gly Ala Ile Asp Pro Glu Thr Gly Gly Thr Ala Tyr Asn Gln Lys Phe
    50                  55                  60

Lys Gly Arg Ala Thr Ile Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Asp Tyr Asp Tyr Asp Gly Phe Ala Tyr Trp Gly Gln Gly Thr Leu
            100                 105                 110

Val Thr Val Ser Ser
        115

<210> SEQ ID NO 56
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Glu Met His Trp Val Arg Gln Ala Pro Gly Gln Gly Leu Glu Trp Met
        35                  40                  45

Gly Ala Ile Asp Pro Glu Thr Gly Gly Thr Ala Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asp Tyr Asp Tyr Asp Gly Phe Ala Tyr Trp Gly Gln Gly Thr Leu
            100                 105                 110

Val Thr Val Ser Ser
        115

<210> SEQ ID NO 57
<211> LENGTH: 117
```

```
<212> TYPE: PRT
<213> ORGANISM: Artificial Sequence
<220> FEATURE:
<223> OTHER INFORMATION: Synthetic polypeptide

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Glu Met His Trp Val Arg Gln Ala Pro Gly Gln Gly Leu Glu Trp Met
        35                  40                  45

Gly Ala Ile Asp Pro Glu Thr Gly Gly Thr Ala Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Asp Tyr Asp Tyr Asp Gly Phe Ala Tyr Trp Gly Gln Gly Thr Leu
            100                 105                 110

Val Thr Val Ser Ser
        115

<210> SEQ ID NO 58
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Glu Met His Trp Val Arg Gln Ala Pro Gly Gln Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Arg Ala Thr Ile Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Thr Asp Tyr Asp Tyr Asp Gly Phe Ala Tyr Trp Gly Gln Gly Thr Leu
            100                 105                 110

Val Thr Val Ser Ser
        115

<210> SEQ ID NO 59
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
```

```
                    20                  25                  30

Glu Met His Trp Val Arg Gln Ala Pro Gly Gln Gly Leu Glu Trp Met
            35                  40                  45

Gly Ala Ile Asp Pro Glu Thr Gly Gly Thr Ala Tyr Asn Gln Lys Phe
        50                  55                  60

Lys Gly Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asp Tyr Asp Tyr Asp Gly Phe Ala Tyr Trp Gly Gln Gly Thr Leu
            100                 105                 110

Val Thr Val Ser Ser
        115

<210> SEQ ID NO 60
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Ile Asp Pro Glu Thr Gly Gly Thr Ala Tyr Asn Gln Lys Phe
    50                  55                  60

Lys Gly Arg Ala Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asp Tyr Asp Tyr Asp Gly Phe Ala Tyr Trp Gly Gln Gly Thr Leu
            100                 105                 110

Val Thr Val Ser Ser
        115

<210> SEQ ID NO 61
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Ile Asp Pro Glu Thr Gly Gly Thr Ala Tyr Asn Gln Lys Phe
    50                  55                  60

Lys Gly Arg Val Thr Met Thr Ala Asp Lys Ser Thr Ser Thr Ala Tyr
65                  70                  75                  80
```

Met Glu Leu Ser Ser Leu Arg Ser Glu Asp Thr Ala Val Tyr Tyr Cys
                85                  90                  95

Ala Asp Tyr Asp Tyr Asp Gly Phe Ala Tyr Trp Gly Gln Gly Thr Leu
            100                 105                 110

Val Thr Val Ser Ser
        115

<210> SEQ ID NO 62
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 62

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Ile Asp Pro Glu Thr Gly Gly Thr Ala Tyr Asn Gln Lys Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asp Tyr Asp Tyr Asp Gly Phe Ala Tyr Trp Gly Gln Gly Thr Leu
            100                 105                 110

Val Thr Val Ser Ser
        115

<210> SEQ ID NO 63
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 63

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Ile Asp Pro Glu Thr Gly Gly Thr Ala Tyr Ala Gln Lys Phe
    50                  55                  60

Gln Gly Arg Ala Thr Ile Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Asp Tyr Asp Tyr Asp Gly Phe Ala Tyr Trp Gly Gln Gly Thr Leu
            100                 105                 110

Val Thr Val Ser Ser
        115

<210> SEQ ID NO 64

<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 64

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Ile Asp Pro Glu Thr Gly Gly Thr Ala Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Asp Tyr Asp Tyr Asp Gly Phe Ala Tyr Trp Gly Gln Gly Thr Leu
            100                 105                 110

Val Thr Val Ser Ser
        115

<210> SEQ ID NO 65
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 65

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Ser Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Asn
                85                  90                  95

Thr His Val Pro Pro Leu Thr Phe Gly Gly Gly Thr Lys Val Glu Ile
            100                 105                 110

Lys

<210> SEQ ID NO 66
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 66

Asp Ile Val Met Thr Gln Ser Pro Leu Ser Leu Ser Ile Thr Pro Gly
1               5                   10                  15

Glu Gln Ala Ser Ile Ser Cys Arg Ser Ser Gln Ser Leu Val His Ser

```
            20                  25                  30
Asn Gly Asn Thr Tyr Leu His Trp Tyr Leu Gln Lys Pro Gly Gln Ser
            35                  40                  45

Pro Gln Leu Leu Ile Ser Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Asn
                85                  90                  95

Thr His Val Pro Pro Leu Thr Phe Gly Gly Gly Thr Lys Val Glu Ile
            100                 105                 110

Lys

<210> SEQ ID NO 67
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 67

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
            35                  40                  45

Pro Gln Leu Leu Ile Ser Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Asn
                85                  90                  95

Thr His Val Pro Pro Leu Thr Phe Gly Gly Gly Thr Lys Val Glu Ile
            100                 105                 110

Lys

<210> SEQ ID NO 68
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 68

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Pro
            35                  40                  45

Pro Arg Leu Leu Ile Ser Lys Val Ser Asn Arg Phe Ser Gly Val Pro
        50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Phe Cys Ser Gln Asn
                85                  90                  95
```

Thr His Val Pro Pro Leu Thr Phe Gly Gly Gly Thr Lys Val Glu Ile
            100                 105                 110
Lys

<210> SEQ ID NO 69
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 69

Met Glu Trp Ser Trp Val Phe Leu Phe Phe Leu Ser Val Thr Thr Gly
1               5                   10                  15

Val His Ser

<210> SEQ ID NO 70
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 70
caggtccagc tggtccagtc aggagccgaa gtgaagaaac ccggagctc cgtgaaggtc       60 agttgcaaag cctccggcgg gactttcagc gactacgaga tgcactgggt gaggcaggct    120
ccaggacagg gactggagtg gatgggagct atcgatcctg aaacaggagg cactgcatac    180
aaccagaagt ttaaaggccg gcgaccatt acagcagaca gtccacttc taccgcctat     240 atggagctgc gtagtctgcg gtctgaagat acagccgtct actattgtgc tgattacgac    300
tatgatggct cgcctattg gggccagggg accctggtga cagtctcaag c              351

<210> SEQ ID NO 71
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 71
caggtccagc tggtccagtc aggagccgaa gtgaagaaac ccggagctc cgtgaaggtc       60 agttgcaaag cctccggcgg gactttcagc gactacgaga tgcactgggt gaggcaggct    120
ccaggacagg gactggagtg gatgggagct atcgatcctg aaacaggagg cactgcatac    180
aaccagaagt ttaaaggccg ggtgaccatt acagcagaca gtccacttc taccgcctat     240 atggagctgt ctagtctgcg gtctgaagat acagccgtct actattgtgc tgattacgac    300
tatgatggct cgcctattg gggccagggg accctggtga cagtctcaag c              351

<210> SEQ ID NO 72
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 72
caggtccagc tggtccagtc aggagccgaa gtgaagaaac ccggagctc cgtgaaggtc       60 agttgcaaag cctccggcgg gactttcagc gactacgaga tgcactgggt gaggcaggct    120

```
ccaggacagg gactggagtg gatgggagct atcgatcctg aaacaggagg cactgcatac      180
aaccagaagt ttaaaggccg ggtgaccatt acagcagaca agtccacttc taccgcctat      240
atggagctgc gtagtctgcg gtctgaagat acagccgtct actattgtgc tgattacgac      300
tatgatggct cgcctattg gggccagggg accctggtga cagtctcaag c                351
```

<210> SEQ ID NO 73
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 73

```
atggaatggt cttgggtctt tctgttctt ctgtctgtca caaccggagt gcatagc          57
```

<210> SEQ ID NO 74
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 74

```
caggtccagc tggtccagtc aggagccgag gtgaagaaac ccggcagctc cgtgaaggtc      60
agttgcaagg ccagcgggta cacattcagc gattatgaga tgcactgggt caggcaggca      120
ccaggacagg gactggagtg gatcggagca attgaccctg aaacaggcgg gactgcctac      180
aaccagaagt ttaaaggccg ggccaccatc acagctgata agtcaactag caccgcttat      240
atggagctgc ggtccctgag atctgaagac actgcagtgt actattgtac cgactacgat      300
tatgacgggt cgcctactg ggggcaggga accctggtga cagtctctag t                351
```

<210> SEQ ID NO 75
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 75

```
atggaatggt catgggtctt tctgttctt ctgtcagtca caaccggagt gcatagc          57
```

<210> SEQ ID NO 76
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 76

```
caggtccagc tggtgcagtc aggagccgaa gtgaagaaac ccggcgcatc cgtgaaggtc      60
tcttgcaaag ccagcgggta caccttcaca gactatgaga tgcactgggt ccgacaggca      120
ccaggacagg gactggagtg gatgggagct atcgatcctg aaacaggcgg gactgcatac      180
aaccagaagt ttaaaggccg ggtgactatg accgcagaca catcaactag caccgcctat      240
atggagctga gctccctgag gagcgaagat accgccgtgt actattgtgc tgattacgac      300
tatgatgggt cgcttactg ggggcaggga accctggtga cagtctctag t                351
```

<210> SEQ ID NO 77
<211> LENGTH: 351

<212> TYPE: DNA
<213> ORGANISM: Artificial Sequence
<220> FEATURE:
<223> OTHER INFORMATION: Synthetic polynucleotide

<400> SEQUENCE: 77

```
caggtccagc tggtgcagtc aggagccgaa gtgaagaaac ccggcgcatc cgtgaaggtc      60
tcttgcaaag ccagcgggta caccttcaca gactatgaga tgcactgggt ccgacaggca     120
ccaggacagg gactggagtg gatgggagct atcgatcctg aaacaggcgg gactgcatac     180
aaccagaagt ttaaaggccg ggcgactatg accgcagaca catcaactag caccgcctat     240
atggagctga gctccctgag gagcgaagat accgccgtgt actattgtgc tgattacgac     300
tatgatgggt tcgcttactg ggggcaggga accctggtga cagtctctag t              351
```

<210> SEQ ID NO 78
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 78

```
caggtccagc tggtgcagtc aggagccgaa gtgaagaaac ccggcgcatc cgtgaaggtc      60
tcttgcaaag ccagcgggta caccttcaca gactatgaga tgcactgggt ccgacaggca     120
ccaggacagg gactggagtg gatgggagct atcgatcctg aaacaggcgg gactgcatac     180
aaccagaagt ttaaaggccg ggtgactatg accgcagaca aatcaactag caccgcctat     240
atggagctga gctccctgag gagcgaagat accgccgtgt actattgtgc tgattacgac     300
tatgatgggt tcgcttactg ggggcaggga accctggtga cagtctctag t              351
```

<210> SEQ ID NO 79
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 79

```
atggaatggt catgggtctt tctgttcttt ctgtccgtca caaccggggt ccactct         57
```

<210> SEQ ID NO 80
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 80

```
caggtgcagc tggtgcagtc tgggagcgag ctgaagaaac ccggggcatc agtgaaggtc      60
agctgcaaag cctccggata caccttcaca gactatgaga tgcactgggt gcggcaggca     120
ccaggacagg gactggagtg gatgggcgct atcgatcctg aaactggcgg gaccgcatac     180
aaccagaagt ttaaagggag attcgtgttt agtctggaca catctgtcag tactgcctat     240
ctgcagatta gctccctgaa ggccgaagat accgctgtct actattgtgc tgactacgat     300
tacgacggct tcgcctattg ggggcaggga acactggtca ctgtctcttc t              351
```

<210> SEQ ID NO 81
<211> LENGTH: 57
<212> TYPE: DNA

<213> ORGANISM: Artificial Sequence
<220> FEATURE:
<223> OTHER INFORMATION: Synthetic polynucleotide

<400> SEQUENCE: 81

```
atggaatggt cttgggtctt tctgttcttt ctgtctgtca caaccggggt ccactct        57
```

<210> SEQ ID NO 82
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 82

```
caggtccagc tggtccagag tggggctgaa gtgaagaaac ccggcagctc cgtgaaggtc       60
agttgcaaag cctccgggta caccttcaca gactatgaga tgcactgggt gaggcaggca      120
ccaggacagg gactggagtg gatgggagct atcgatcctg aaaccggcgg gacagcctac      180
gctcagaagt ttcagggccg ggcgactatt accgctgaca aatccacatc tactgcatat      240
atggagctgc gtagtctgcg gagcgaagat acagcagtct actattgtgc cgattacgac      300
tatgatgggt tcgcctactg ggggcaggga actctggtga ccgtctcaag c               351
```

<210> SEQ ID NO 83
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 83

```
caggtccagc tggtccagag tggggctgaa gtgaagaaac ccggcagctc cgtgaaggtc       60
agttgcaaag cctccgggta caccttcaca gactatgaga tgcactgggt gaggcaggca      120
ccaggacagg gactggagtg gatgggagct atcgatcctg aaaccggcgg gacagcctac      180
gctcagaagt ttcagggccg ggtgactatt accgctgaca aatccacatc tactgcatat      240
atggagctgc gtagtctgcg gagcgaagat acagcagtct actattgtgc cgattacgac      300
tatgatgggt tcgcctactg ggggcaggga actctggtga ccgtctcaag c               351
```

<210> SEQ ID NO 84
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 84

```
atggaatggt cttgggtctt tctgttcttt ctgagcgtga ctaccggagt gcatagc        57
```

<210> SEQ ID NO 85
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 85

```
Met Ser Val Pro Thr Gln Val Leu Gly Leu Leu Leu Leu Trp Leu Thr
1               5                   10                  15

Asp Ala Arg Cys
            20
```

<210> SEQ ID NO 86
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 86

```
gatattgtga tgacccagtc tcctctgtcc ctgccagtga caccaggaga gcctgcctct    60
atcagttgca ggagctccca gtctctggtc cacagtaacg gcaatactta cctgcattgg   120
tatctgcaga agccagggca gagcccccag ctgctgatct ccaaagtgtc aaaccggttc   180
agcggagtcc ctgacagatt ttcaggcagc gggtccggaa ccgatttcac actgaagatt   240
tcccgggtgg aggctgaaga cgtgggcgtc tactttgtt ctcagaatac ccacgtgccc    300
cctctgactt ttggcggggg aaccaaggtc gagatcaag                          339
```

<210> SEQ ID NO 87
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 87

```
gatattgtga tgacccagtc tcctctgtcc ctgtcaatca caccaggaga gcaggcctct    60
atcagttgca ggagctccca gtctctggtc cacagtaacg gcaatactta cctgcattgg   120
tatctgcaga agccagggca gagcccccag ctgctgatct ccaaagtgtc aaaccggttc   180
agcggagtcc ctgacagatt ttcaggcagc gggtccggaa ccgatttcac actgaagatt   240
tcccgggtgg aggctgaaga cgtgggcgtc tactttgtt ctcagaatac ccacgtgccc    300
cctctgactt ttggcggggg aaccaaggtc gagatcaag                          339
```

<210> SEQ ID NO 88
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 88

```
atgtccgtgc ctactcaggt gctggggctg ctgctgctgt ggctgaccga tgcccgctgc    60
```

<210> SEQ ID NO 89
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 89

```
gatgtcgtga tgacccagtc tcctctgagc ctgccagtga caccaggaga gcctgcctct    60
atcagttgca ggagctccca gtcactggtc cacagcaacg gcaatactta cctgcattgg   120
tatctgcaga agccagggca gtcccccccag ctgctgatct ctaaagtgag taaccggttc   180
tctggagtcc ctgacagatt ttcaggcagc gggtccggaa ccgatttcac actgaagatt   240
agtcgggtgg aggctgaaga cgtgggcgtc tacttctgtt ctcagaatac ccacgtgccc    300
cctctgactt ttggcggggg aaccaaggtc gagatcaag                          339
```

<210> SEQ ID NO 90
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 90
atgtccgtgc ctactcaggt gctggggctg ctgctgctgt ggctgaccga tgcccgatgt    60

<210> SEQ ID NO 91
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 91
gatgtcgtga tgacccagtc tcctctgagc ctgccagtga caccaggaga gcctgcctct    60
atcagttgca ggagctccca gtcactggtc cacagcaacg gaatactta cctgcattgg   120 tatctgcaga agccagggca gtcccccag ctgctgatct ctaaagtgag taaccggttc   180
tctggagtcc ctgacagatt ttcaggcagc gggtccggaa ccgatttcac actgaagatt   240
agtcgggtgg aggctgaaga cgtgggcgtc tacttctgtt ctcagaatac ccacgtgccc   300
cctctgactt ttggcggggg aaccaaggtc gagatcaag                          339

<210> SEQ ID NO 92
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 92
atgagcgtgc ctacccaggt gctgggactg ctgctgctgt ggctgactga tgcccgatgt    60

<210> SEQ ID NO 93
<211> LENGTH: 172
<212> TYPE: PRT
<213> ORGANISM: Mus musculus

<400> SEQUENCE: 93

Met Ser Ser Lys Arg Ala Lys Thr Lys Thr Thr Lys Lys Arg Pro Gln
1               5                   10                  15

Arg Ala Thr Ser Asn Val Phe Ala Met Phe Asp Gln Ser Gln Ile Gln
            20                  25                  30

Glu Phe Lys Glu Ala Phe Asn Met Ile Asp Gln Asn Arg Asp Gly Phe
        35                  40                  45

Ile Asp Lys Glu Asp Leu His Asp Met Leu Ala Ser Met Gly Lys Asn
    50                  55                  60

Pro Thr Asp Glu Tyr Leu Asp Ala Met Met Asn Glu Ala Pro Gly Pro
65                  70                  75                  80

Ile Asn Phe Thr Met Phe Leu Thr Met Phe Gly Glu Lys Leu Asn Gly
                85                  90                  95

Thr Asp Pro Glu Asp Val Ile Arg Asn Ala Phe Ala Cys Phe Asp Glu
            100                 105                 110

Glu Ala Ile Gly Thr Ile Gln Glu Asp Tyr Leu Arg Glu Leu Leu Thr
        115                 120                 125

Thr Met Gly Asp Arg Phe Thr Asp Glu Glu Val Asp Glu Leu Tyr Arg

```
                130                 135                 140
Glu Ala Pro Ile Asp Lys Lys Gly Asn Phe Asn Tyr Ile Glu Phe Thr
145                 150                 155                 160

Arg Ile Leu Lys His Gly Ala Lys Asp Lys Asp
                165                 170

<210> SEQ ID NO 94
<211> LENGTH: 172
<212> TYPE: PRT
<213> ORGANISM: Mus musculus

<400> SEQUENCE: 94

Met Ser Ser Lys Lys Ala Lys Thr Lys Thr Lys Lys Arg Pro Gln
1               5                   10                  15

Arg Ala Thr Ser Asn Val Phe Ala Met Phe Asp Gln Ser Gln Ile Gln
                20                  25                  30

Glu Phe Lys Glu Ala Phe Asn Met Ile Asp Gln Asn Arg Asp Gly Phe
            35                  40                  45

Ile Asp Lys Glu Asp Leu His Asp Met Leu Ala Ser Leu Gly Lys Asn
        50                  55                  60

Pro Thr Asp Ala Tyr Leu Asp Ala Met Met Asn Glu Ala Pro Gly Pro
65                  70                  75                  80

Ile Asn Phe Thr Met Phe Leu Thr Met Phe Gly Glu Lys Leu Asn Gly
                85                  90                  95

Thr Asp Pro Glu Asp Val Ile Arg Asn Ala Phe Ala Cys Phe Asp Glu
            100                 105                 110

Glu Ala Thr Gly Thr Ile Gln Glu Asp Tyr Leu Arg Glu Leu Leu Thr
        115                 120                 125

Thr Met Gly Asp Arg Phe Thr Asp Glu Glu Val Asp Glu Leu Tyr Arg
    130                 135                 140

Glu Ala Pro Ile Asp Lys Lys Gly Asn Phe Asn Tyr Ile Glu Phe Thr
145                 150                 155                 160

Arg Ile Leu Lys His Gly Ala Lys Asp Lys Asp
                165                 170

<210> SEQ ID NO 95
<211> LENGTH: 171
<212> TYPE: PRT
<213> ORGANISM: Homo sapiens

<400> SEQUENCE: 95

Met Ser Ser Lys Arg Thr Lys Thr Lys Thr Lys Lys Arg Pro Gln Arg
1               5                   10                  15

Ala Thr Ser Asn Val Phe Ala Met Phe Asp Gln Ser Gln Ile Gln Glu
                20                  25                  30

Phe Lys Glu Ala Phe Asn Met Ile Asp Gln Asn Arg Asp Gly Phe Ile
            35                  40                  45

Asp Lys Glu Asp Leu His Asp Met Leu Ala Ser Leu Gly Lys Asn Pro
        50                  55                  60

Thr Asp Glu Tyr Leu Asp Ala Met Met Asn Glu Ala Pro Gly Pro Ile
65                  70                  75                  80

Asn Phe Thr Met Phe Leu Thr Met Phe Gly Glu Lys Leu Asn Gly Thr
                85                  90                  95

Asp Pro Glu Asp Val Ile Arg Asn Ala Phe Ala Cys Phe Asp Glu Glu
            100                 105                 110

Ala Thr Gly Thr Ile Gln Glu Asp Tyr Leu Arg Glu Leu Leu Thr Thr
```

Met Gly Asp Arg Phe Thr Asp Glu Glu Val Asp Glu Leu Tyr Arg Glu
    130                 135                 140
Ala Pro Ile Asp Lys Lys Gly Asn Phe Asn Tyr Ile Glu Phe Thr Arg
145                 150                 155                 160
Ile Leu Lys His Gly Ala Lys Asp Lys Asp
                165                 170

<210> SEQ ID NO 96
<211> LENGTH: 172
<212> TYPE: PRT
<213> ORGANISM: Homo sapiens

<400> SEQUENCE: 96

Met Ser Ser Lys Lys Ala Lys Thr Lys Thr Thr Lys Lys Arg Pro Gln
1               5                   10                  15
Arg Ala Thr Ser Asn Val Phe Ala Met Phe Asp Gln Ser Gln Ile Gln
                20                  25                  30
Glu Phe Lys Glu Ala Phe Asn Met Ile Asp Gln Asn Arg Asp Gly Phe
            35                  40                  45
Ile Asp Lys Glu Asp Leu His Asp Met Leu Ala Ser Leu Gly Lys Asn
    50                  55                  60
Pro Thr Asp Ala Tyr Leu Asp Ala Met Met Asn Glu Ala Pro Gly Pro
65                  70                  75                  80
Ile Asn Phe Thr Met Phe Leu Thr Met Phe Gly Glu Lys Leu Asn Gly
                85                  90                  95
Thr Asp Pro Glu Asp Val Ile Arg Asn Ala Phe Ala Cys Phe Asp Glu
            100                 105                 110
Glu Ala Thr Gly Thr Ile Gln Glu Asp Tyr Leu Arg Glu Leu Leu Thr
    115                 120                 125
Thr Met Gly Asp Arg Phe Thr Asp Glu Glu Val Asp Glu Leu Tyr Arg
130                 135                 140
Glu Ala Pro Ile Asp Lys Lys Gly Asn Phe Asn Tyr Ile Glu Phe Thr
145                 150                 155                 160
Arg Ile Leu Lys His Gly Ala Lys Asp Lys Asp
                165                 170

<210> SEQ ID NO 97
<211> LENGTH: 136
<212> TYPE: PRT
<213> ORGANISM: Homo sapiens

<400> SEQUENCE: 97

Gly Gln Tyr Asn Cys Pro Gly Gln Tyr Thr Phe Ser Met Pro Ser Asp
1               5                   10                  15
Ser His Val Ser Ser Cys Ser Glu Asp Trp Val Gly Tyr Gln Arg Lys
                20                  25                  30
Cys Tyr Phe Ile Ser Thr Val Lys Arg Ser Trp Thr Ser Ala Gln Asn
            35                  40                  45
Ala Cys Ser Glu His Gly Ala Thr Leu Ala Val Ile Asp Ser Glu Lys
    50                  55                  60
Asp Met Asn Phe Leu Lys Arg Tyr Ala Gly Arg Glu Glu His Trp Val
65                  70                  75                  80
Gly Leu Lys Lys Glu Pro Gly His Pro Trp Lys Trp Ser Asn Gly Lys
                85                  90                  95
Glu Phe Asn Asn Trp Phe Asn Val Thr Gly Ser Asp Lys Cys Val Phe

```
                100                 105                 110
Leu Lys Asn Thr Glu Val Ser Ser Met Glu Cys Glu Lys Asn Leu Tyr
        115                 120                 125

Trp Ile Cys Asn Lys Pro Tyr Lys
    130                 135
```

ANTI-MYL9 ANTIBODY

TECHNICAL FIELD

The present invention relates to an antibody that binds to myosin regulatory light chain polypeptide (Myl)9 or a Myl9 binding fragment thereof, as well as a pharmaceutical composition comprising said antibody or Myl9 binding fragment thereof.

BACKGROUND ART

CD69 is a type II transmembrane protein that belongs to the C-type lectin family. CD69 is broadly employed as an indicator of lymphocyte activation (Non-Patent Literature 1), and thus far has been reported to be involved in inflammatory diseases such as local inflammation, arthritis, and allergic airway symptoms (Non-Patent Literatures 2 and 3).

In recent years, it has been reported that CD69 interacts with myosin regulatory light chain polypeptide (Myl)9 which is one of the subunits configuring myosin, and with this, therapeutic strategies of inflammation diseases that target Myl9 have been brought under view (Patent Literature 1).

An immune checkpoint inhibitor is a group of recently developed anti-cancer drugs and it inhibits proteins expressed in cancer cells and lymphocytes (T cells) which put the brakes on immune system. The proteins are called immune checkpoints. Programmed cell death protein-1 (PD-1), programmed death-ligand 1 (PD-L1) and cytotoxic T-lymphocyte-associated antigen-4 (CTLA-4) and the like are known to act as immune checkpoints. Several immune checkpoint inhibitors have been approved as drugs and their therapeutic uses include malignant melanoma, non-small cell lung cancer, renal cell carcinoma, malignant lymphoma, multiple myeloma, head and neck cancer, and urothelial cancer. In addition, treatment of immune checkpoint inhibitors alone or in combination with other anti-cancer drug is effective against cancers such as colorectal cancer, breast cancer, hepatocellular carcinoma, gastric cancer, esophageal cancer, ovarian cancer, small cell lung cancer, mesothelioma, endometrial cancer according to clinical trial results.

CITATION LIST

Patent Literature

[Patent Literature 1] WO2014/192915

Non Patent Literature

[Non-Patent Literature 1] Testi, R. et al., Immunol. Today 15:479-483, 1994.
[Non-Patent Literature 2] Murata, K. et al.: CD69-null mice protected from arthritis induced with anti-type II collagen antibodies. Int. Immunol. 15:987-992, 2003
[Non-Patent Literature 3] Miki-Hosokawa, T. et al.: CD69 controls the pathogenesis of allergic airway inflammation. J. Immunol. 183; 8203-8215, 2009

SUMMARY OF INVENTION

Technical Problem

Antibodies and antigen binding fragments may become desirable therapeutic drugs due to the binding specificity they possess. Antibodies and antigen binding fragments may be employed to minimize potential side effects by targeting only particular cells or tissues. There is a need to identify an antibody useful for targeting Myl9, as well as a humanized antibody that is used as a pharmaceutical.

Accordingly, the object of the present invention is to provide an anti-Myl9 antibody or a Myl9 binding fragment thereof that binds to Myl9 and can inhibit the interaction between Myl9 and CD69 in humans, as well as a pharmaceutical composition comprising the same.

Solution to Problem

As a result of extensive investigation to solve the above problems, the present inventors succeeded in obtaining a mouse anti-mouse/human Myl9 monoclonal antibody that binds to human and mouse Myl9 and may inhibit interaction with CD69. Consequently, the present inventors obtained a humanized or chimeric antibody comprising the complementarity determining region (CDR, (may sometimes be referred to as "hypervariable region")) sequence of said mouse anti-mouse/human Myl9 monoclonal antibody in the variable region of heavy and light chains by identifying the CDR of said mouse anti-mouse/human Myl9 monoclonal antibody.

In other words, the present invention encompasses the following characteristics.

[1] An anti-myosin regulatory light chain polypeptide (Myl)9 antibody or a Myl9 binding fragment thereof comprising:
  (a) a heavy chain CDR1 consisting of a peptide represented by the amino acid sequence set forth in SEQ ID NO. 28;
  (b) a heavy chain CDR2 consisting of a peptide represented by the amino acid sequence set forth in SEQ ID NO. 30;
  (c) a heavy chain CDR3 consisting of a peptide represented by the amino acid sequence set forth in SEQ ID NO. 32;
  (d) a light chain CDR1 consisting of a peptide represented by the amino acid sequence set forth in SEQ ID NO. 33;
  (e) a light chain CDR2 consisting of a peptide represented by the amino acid sequence set forth in SEQ ID NO. 34; and
  (f) a light chain CDR3 consisting of a peptide represented by the amino acid sequence set forth in SEQ ID NO. 35.
[2] The anti-Myl9 antibody or Myl9 binding fragment thereof according to [1], wherein said antibody is a humanized or chimeric antibody.
[3] The anti-Myl9 antibody or Myl9 binding fragment thereof according to [1] or [2], wherein said Myl9 is human Myl9.
[4] The anti-Myl9 antibody or Myl9 binding fragment thereof according to any of [1]-[3] that inhibits the interaction between Myl9 and CD69, wherein
  said antibody comprises a heavy chain and a light chain,
  the variable region of said heavy chain comprises a peptide represented by the amino acid sequence set forth in SEQ ID NOs. 55, 56, 57, 58, 59, 60, 61, 62, 63, or 64, and
  the variable region of said light chain comprises a peptide represented by the amino acid sequence set forth in SEQ ID NOs. 65, 66, 67, or 68.
[5] The anti-Myl9 antibody or Myl9 binding fragment thereof according to any of [1]-[4], wherein said antibody is selected from the group consisting of the following antibodies:
  (1) an antibody comprising a heavy chain variable region comprising a peptide represented by the amino acid sequence set forth in SEQ ID NO. 64 and a light chain variable region comprising a peptide represented by the amino acid sequence set forth in SEQ ID NO. 66;

(2) an antibody comprising a heavy chain variable region comprising a peptide represented by the amino acid sequence set forth in SEQ ID NO. 63 and a light chain variable region comprising a peptide represented by the amino acid sequence set forth in SEQ ID NO. 66;

(3) an antibody comprising a heavy chain variable region comprising a peptide represented by the amino acid sequence set forth in SEQ ID NO. 56 and a light chain variable region comprising a peptide represented by the amino acid sequence set forth in SEQ ID NO. 66;

(4) an antibody comprising a heavy chain variable region comprising a peptide represented by the amino acid sequence set forth in SEQ ID NO. 57 and a light chain variable region comprising a peptide represented by the amino acid sequence set forth in SEQ ID NO. 66;

(5) an antibody comprising a heavy chain variable region comprising a peptide represented by the amino acid sequence set forth in SEQ ID NO. 55 and a light chain variable region comprising a peptide represented by the amino acid sequence set forth in SEQ ID NO. 66;

(6) an antibody comprising a heavy chain variable region comprising a peptide represented by the amino acid sequence set forth in SEQ ID NO. 58 and a light chain variable region comprising a peptide represented by the amino acid sequence set forth in SEQ ID NO. 66;

(7) an antibody comprising a heavy chain variable region comprising a peptide represented by the amino acid sequence set forth in SEQ ID NO. 59 and a light chain variable region comprising a peptide represented by the amino acid sequence set forth in SEQ ID NO. 66;

(8) an antibody comprising a heavy chain variable region comprising a peptide represented by the amino acid sequence set forth in SEQ ID NO. 60 and a light chain variable region comprising a peptide represented by the amino acid sequence set forth in SEQ ID NO. 66;

(9) an antibody comprising a heavy chain variable region comprising a peptide presented by the amino acid sequence set forth in SEQ ID NO. 61 and a light chain variable region comprising a peptide represented by the amino acid sequence set forth in SEQ ID NO. 66;

(10) an antibody comprising a heavy chain variable region comprising a peptide represented by the amino acid sequence set forth in SEQ ID NO. 64 and a light chain variable region comprising a peptide represented by the amino acid sequence set forth in SEQ ID NO. 68;

(11) an antibody comprising a heavy chain variable region comprising a peptide represented by the amino acid sequence set forth in SEQ ID NO. 63 and a light chain variable region comprising a peptide represented by the amino acid sequence set forth in SEQ ID NO. 68;

(12) an antibody comprising a heavy chain variable region comprising a peptide represented by the amino acid sequence set forth in SEQ ID NO. 56 and a light chain variable region comprising a peptide represented by the amino acid sequence set forth in SEQ ID NO. 68;

(13) an antibody comprising a heavy chain variable region comprising a peptide represented by the amino acid sequence set forth in SEQ ID NO. 57 and a light chain variable region comprising a peptide represented by the amino acid sequence set forth in SEQ ID NO. 68;

(14) an antibody comprising a heavy chain variable region comprising a peptide represented by the amino acid sequence set forth in SEQ ID NO. 55 and a light chain variable region comprising a peptide represented by the amino acid sequence set forth in SEQ ID NO. 68;

(15) an antibody comprising a heavy chain variable region comprising a peptide represented by the amino acid sequence set forth in SEQ ID NO. 58 and a light chain variable region comprising a peptide represented by the amino acid sequence set forth in SEQ ID NO. 68;

(16) an antibody comprising a heavy chain variable region comprising a peptide represented by the amino acid sequence set forth in SEQ ID NO. 59 and a light chain variable region comprising a peptide represented by the amino acid sequence set forth in SEQ ID NO. 68;

(17) an antibody comprising a heavy chain variable region comprising a peptide represented by the amino acid sequence set forth in SEQ ID NO. 60 and a light chain variable region comprising a peptide represented by the amino acid sequence set forth in SEQ ID NO. 68;

(18) an antibody comprising a heavy chain variable region comprising a peptide represented by the amino acid sequence set forth in SEQ ID NO. 61 and a light chain variable region comprising a peptide represented by the amino acid sequence set forth in SEQ ID NO. 68;

(19) an antibody comprising a heavy chain variable region comprising a peptide represented by the amino acid sequence set forth in SEQ ID NO. 62 and a light chain variable region comprising a peptide represented by the amino acid sequence set forth in SEQ ID NO. 65;

(20) an antibody comprising a heavy chain variable region comprising a peptide represented by the amino acid sequence set forth in SEQ ID NO. 62 and a light chain variable region comprising a peptide represented by the amino acid sequence set forth in SEQ ID NO. 67;

(21) an antibody comprising a heavy chain variable region comprising a peptide represented by the amino acid sequence set forth in SEQ ID NO. 62 and a light chain variable region comprising a peptide represented by the amino acid sequence set forth in SEQ ID NO. 66; and

(22) an antibody comprising a heavy chain variable region comprising a peptide represented by the amino acid sequence set forth in SEQ ID NO. 62 and a light chain variable region comprising a peptide represented by the amino acid sequence set forth in SEQ ID NO. 68.

[6] The anti-Myl9 antibody or Myl9 binding fragment thereof according to any of [1]-[5] that comprises heavy and light chains, wherein the constant region of said heavy chain is IgG

[7] The anti-Myl9 antibody or Myl9 binding fragment thereof according to [6], wherein the constant region of said heavy chain is the constant region of human IgG2.

[8] The anti-Myl9 antibody or Myl9 binding fragment thereof according to [7], wherein said constant region of human IgG2 possesses mutations V234A and G237A.

[9] The anti-Myl9 antibody or Myl9 binding fragment thereof according to [7] or [8], wherein said constant region has the C-terminal lysine residue deletion.

[10] The anti-Myl9 antibody or Myl9 binding fragment thereof according to [6], wherein the constant region of said light chain comprises the constant region of human Igκ.

[11] The anti-Myl9 antibody or Myl9 binding fragment thereof according to any of [1]-[10], wherein said antibody or Myl9 binding fragment thereof inhibits the interaction between Myl12a or Myl12b and CD69.

[12] A pharmaceutical composition comprising the antibody or Myl9 binding fragment thereof according to any of [1]-[11], and a pharmaceutically acceptable carrier or additive.

[13] The pharmaceutical composition according to [12] for treating allergic airway inflammation or inflammatory bowel disease.
[14] The pharmaceutical composition according to [13], wherein the inflammatory bowel disease is ulcerative colitis or Crohn's disease.
[15] The pharmaceutical composition according to [12] for treating tumor, wherein the pharmaceutical composition is used in combination with an immune checkpoint inhibitor.
[16] The pharmaceutical composition according to [15], wherein the immune checkpoint inhibitor is a PD-1 inhibitor.
[17] The pharmaceutical composition according to [16], wherein the PD-1 inhibitor is an anti-PD-1 antibody or an anti-PD-L1 antibody.
[18] The pharmaceutical composition according to [16], wherein the PD-1 inhibitor is an anti-PD-1 antibody.
[19] The pharmaceutical composition according to any of [15]-[18], wherein the tumor is selected from the group consisting of colorectal cancer, malignant melanoma, non-small cell lung cancer, renal cell carcinoma, malignant lymphoma, multiple myeloma, head and neck cancer, urothelial cancer, breast cancer, hepatocellular carcinoma, gastric cancer, esophageal cancer, ovarian cancer, small cell lung cancer, mesothelioma and endometrial cancer.
[20] The pharmaceutical composition according to [19], wherein the tumor is colorectal cancer.

Furthermore, the present invention encompasses the following characteristics.

[1'] An anti-Myl9 antibody or Myl9 binding fragment thereof comprising a heavy chain variable region comprising a peptide represented by the amino acid sequence set forth in SEQ ID NO. 64 and a light chain variable region comprising a peptide represented by the amino acid sequence set forth in SEQ ID NO. 66.
[2'] An anti-Myl9 antibody or Myl9 binding fragment thereof comprising a heavy chain variable region comprising a peptide represented by the amino acid sequence set forth in SEQ ID NO. 63 and a light chain variable region comprising a peptide represented by the amino acid sequence set forth in SEQ ID NO. 66.
[3'] An anti-Myl9 antibody or Myl9 binding fragment thereof comprising a heavy chain variable region comprising a peptide represented by the amino acid sequence set forth in SEQ ID NO. 56 and a light chain variable region comprising a peptide represented by the amino acid sequence set forth in SEQ ID NO. 66.
[4'] An anti-Myl9 antibody or Myl9 binding fragment thereof comprising a heavy chain variable region comprising a peptide represented by the amino acid sequence set forth in SEQ ID NO. 57 and a light chain variable region comprising a peptide represented by the amino acid sequence set forth in SEQ ID NO. 66.
[5'] An anti-Myl9 antibody or Myl9 binding fragment thereof comprising a heavy chain variable region comprising a peptide represented by the amino acid sequence set forth in SEQ ID NO. 55 and a light chain variable region comprising a peptide represented by the amino acid sequence set forth in SEQ ID NO. 66.
[6'] An anti-Myl9 antibody or Myl9 binding fragment thereof comprising a heavy chain variable region comprising a peptide represented by the amino acid sequence set forth in SEQ ID NO. 58 and a light chain variable region comprising a peptide represented by the amino acid sequence set forth in SEQ ID NO. 66.
[7'] An anti-Myl9 antibody or Myl9 binding fragment thereof comprising a heavy chain variable region comprising a peptide represented by the amino acid sequence set forth in SEQ ID NO. 59 and a light chain variable region comprising a peptide represented by the amino acid sequence set forth in SEQ ID NO. 66.
[8'] An anti-Myl9 antibody or Myl9 binding fragment thereof comprising a heavy chain variable region comprising a peptide represented by the amino acid sequence set forth in SEQ ID NO. 60 and a light chain variable region comprising a peptide represented by the amino acid sequence set forth in SEQ ID NO. 66.
[9'] An anti-Myl9 antibody or Myl9 binding fragment thereof comprising a heavy chain variable region comprising a peptide represented by the amino acid sequence set forth in SEQ ID NO. 61 and a light chain variable region comprising a peptide represented by the amino acid sequence set forth in SEQ ID NO. 66.
[10'] An anti-Myl9 antibody or Myl9 binding fragment thereof comprising a heavy chain variable region comprising a peptide represented by the amino acid sequence set forth in SEQ ID NO. 64 and a light chain variable region comprising a peptide represented by the amino acid sequence set forth in SEQ ID NO. 68.
[11'] An anti-Myl9 antibody or Myl9 binding fragment thereof comprising a heavy chain variable region comprising a peptide represented by the amino acid sequence set forth in SEQ ID NO. 63 and a light chain variable region comprising a peptide represented by the amino acid sequence set forth in SEQ ID NO. 68.
[12'] An anti-Myl9 antibody or Myl9 binding fragment thereof comprising a heavy chain variable region comprising a peptide represented by the amino acid sequence set forth in SEQ ID NO. 56 and a light chain variable region comprising a peptide represented by the amino acid sequence set forth in SEQ ID NO. 68.
[13'] An anti-Myl9 antibody or Myl9 binding fragment thereof comprising a heavy chain variable region comprising a peptide represented by the amino acid sequence set forth in SEQ ID NO. 57 and a light chain variable region comprising a peptide represented by the amino acid sequence set forth in SEQ ID NO. 68.
[14'] An anti-Myl9 antibody or Myl9 binding fragment thereof comprising a heavy chain variable region comprising a peptide represented by the amino acid sequence set forth in SEQ ID NO. 55 and a light chain variable region comprising a peptide represented by the amino acid sequence set forth in SEQ ID NO. 68.
[15'] An anti-Myl9 antibody or Myl9 binding fragment thereof comprising a heavy chain variable region comprising a peptide represented by the amino acid sequence set forth in SEQ ID NO. 58 and a light chain variable region comprising a peptide represented by the amino acid sequence set forth in SEQ ID NO. 68.
[16'] An anti-Myl9 antibody or Myl9 binding fragment thereof comprising a heavy chain variable region comprising a peptide represented by the amino acid sequence set forth in SEQ ID NO. 59 and a light chain variable region comprising a peptide represented by the amino acid sequence set forth in SEQ ID NO. 68.
[17'] An anti-Myl9 antibody or Myl9 binding fragment thereof comprising a heavy chain variable region comprising a peptide represented by the amino acid sequence set forth in SEQ ID NO. 60 and a light chain variable region comprising a peptide represented by the amino acid sequence set forth in SEQ ID NO. 68.

[18'] An anti-Myl9 antibody or Myl9 binding fragment thereof comprising a heavy chain variable region comprising a peptide represented by the amino acid sequence set forth in SEQ ID NO. 61 and a light chain variable region comprising a peptide represented by the amino acid sequence set forth in SEQ ID NO. 68.

[19'] An anti-Myl9 antibody or Myl9 binding fragment thereof comprising a heavy chain variable region comprising a peptide represented by the amino acid sequence set forth in SEQ ID NO. 62 and a light chain variable region comprising a peptide represented by the amino acid sequence set forth in SEQ ID NO. 65.

[20'] An anti-Myl9 antibody or Myl9 binding fragment thereof comprising a heavy chain variable region comprising a peptide represented by the amino acid sequence set forth in SEQ ID NO. 62 and a light chain variable region comprising a peptide represented by the amino acid sequence set forth in SEQ ID NO. 67.

[21'] An anti-Myl9 antibody or Myl9 binding fragment thereof comprising a heavy chain variable region comprising a peptide represented by the amino acid sequence set forth in SEQ ID NO. 62 and a light chain variable region comprising a peptide represented by the amino acid sequence set forth in SEQ ID NO. 66.

[22'] An anti-Myl9 antibody or Myl9 binding fragment thereof comprising a heavy chain variable region comprising a peptide represented by the amino acid sequence set forth in SEQ ID NO. 62 and a light chain variable region comprising a peptide represented by the amino acid sequence set forth in SEQ ID NO. 68.

[23'] The anti-Myl9 antibody or Myl9 binding fragment thereof according to any of [1']-[22'] that inhibits the interaction between Myl9 and CD69.

[24'] The anti-Myl9 antibody or Myl9 binding fragment thereof according to any of [1']-[23'] that comprises heavy and light chains, wherein the constant region of said heavy chain is IgG.

[25'] The anti-Myl9 antibody or Myl9 binding fragment thereof according to [24'], wherein the constant region of said heavy chain is the constant region of human IgG2.

[26'] The anti-Myl9 antibody or Myl9 binding fragment thereof according to [25'], wherein said constant region of human IgG2 possesses mutations V234A and G237A.

[27'] The anti-Myl9 antibody or Myl9 binding fragment thereof according to [25'] or [26'], wherein said constant region has the C-terminal lysine residue deletion.

[28'] The anti-Myl9 antibody or Myl9 binding fragment thereof according to [24'], wherein the constant region of said light chain comprises the constant region of human Igκ.

[29'] The anti-Myl9 antibody or Myl9 binding fragment thereof according to any of [1'] to [28'], wherein said antibody or Myl9 binding fragment thereof inhibits the interaction between Myl12a or Myl12b and CD69.

[30'] A pharmaceutical composition comprising the antibody or Myl9 binding fragment thereof according to any of [1'] to [29'], and a pharmaceutically acceptable carrier or additive.

[31'] The pharmaceutical composition according to [30'] for treating allergic airway inflammation or inflammatory bowel disease.

[32'] The pharmaceutical composition according to [31'], wherein the inflammatory bowel disease is ulcerative colitis or Crohn's disease.

[33']. The pharmaceutical composition according to [30'] for treating tumor, wherein the pharmaceutical composition is used in combination with an immune checkpoint inhibitor.

[34'] The pharmaceutical composition according to [33'], wherein the immune checkpoint inhibitor is a PD-1 inhibitor.

[35'] The pharmaceutical composition according to [34'], wherein the PD-1 inhibitor is an anti-PD-1 antibody or an anti-PD-L1 antibody.

[36'] The pharmaceutical composition according to [34'], wherein the PD-1 inhibitor is an anti-PD-1 antibody.

[37'] The pharmaceutical composition according to any of [33']-[36'], wherein the tumor is selected from the group consisting of colorectal cancer, malignant melanoma, non-small cell lung cancer, renal cell carcinoma, malignant lymphoma, multiple myeloma, head and neck cancer, urothelial cancer, breast cancer, hepatocellular carcinoma, gastric cancer, esophageal cancer, ovarian cancer, small cell lung cancer, mesothelioma and endometrial cancer.

[38] The pharmaceutical composition according to [37'] wherein the tumor is colorectal cancer.

An invention of any combination of one or multiple aspects of the present invention listed above is also encompassed in the scope of the present invention.

Advantageous Effects of Invention

According to the present invention, an anti-Myl9 antibody or a Myl9 binding fragment thereof that binds to Myl9 and may inhibit the interaction between Myl9 and CD69, as well as a pharmaceutical composition comprising the same are provided.

BRIEF DESCRIPTION OF DRAWINGS

Figures 1A, 1B:
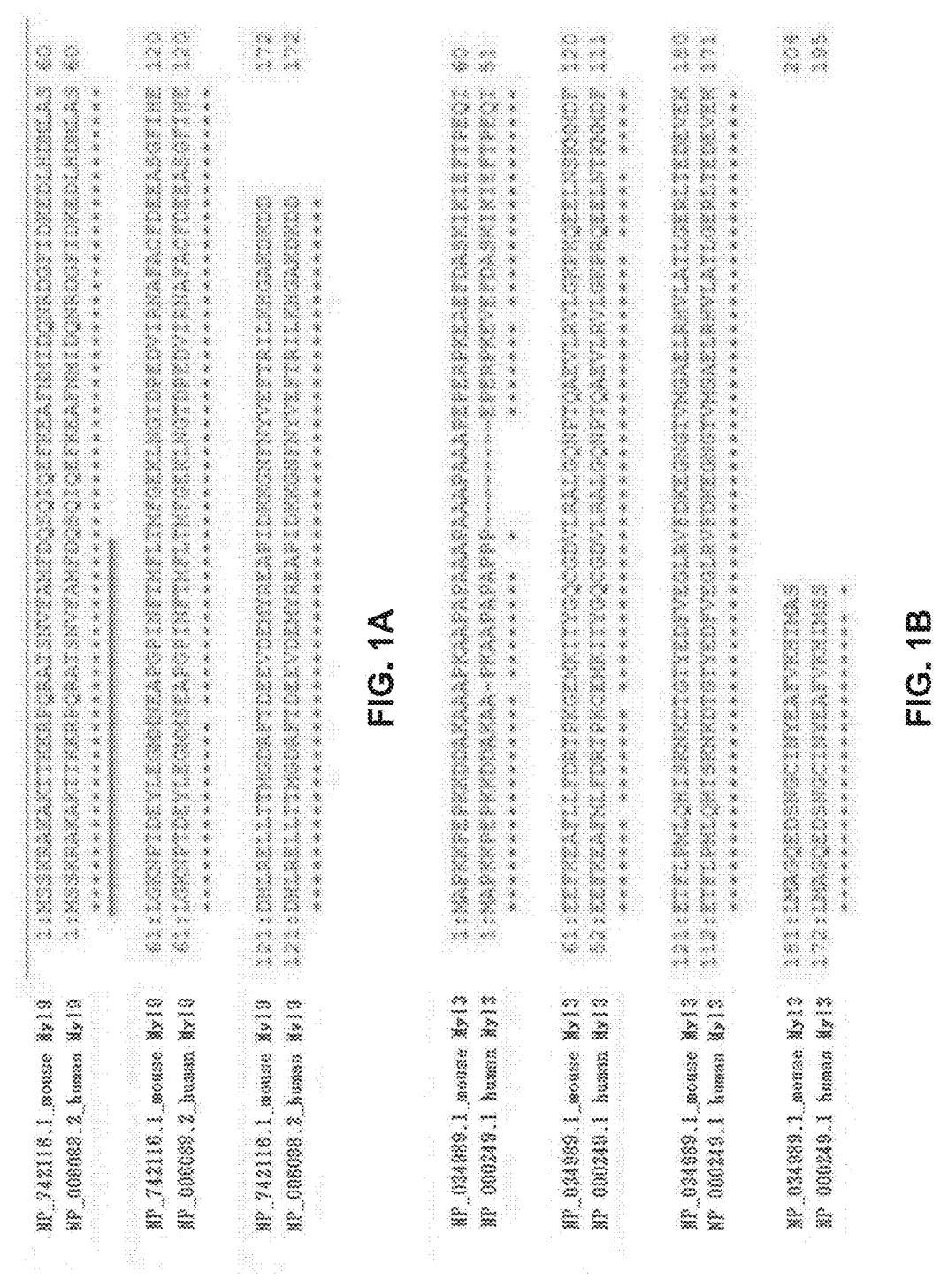

FIGS. 1A-1B show each of the comparison of amino acid sequences between mouse Myl9 and human Myl9 (FIG. 1A) and the comparison of amino acid sequences between mouse Myl3 and human Myl3 (FIG. 1B). *: conserved amino acid; -: gap; underline: amino acid sequence of a peptide used for immunization for mice to prepare Antibody A. In FIG. 1A, NP_742116.1 is shown as SEQ ID NO:1 and NP_006088.2 is shown as SEQ ID NO:2. In FIG. 1B, NP_034989.1 is shown as SEQ ID NO:5 and NP_000249.1 is shown as SEQ ID NO:6.

In FIG. 1C, NP_034989.1 is shown as SEQ ID NO:5 and NP_742116.1 is shown as SEQ ID NO:1. In FIG. 1D, NP_000249.1 is shown as SEQ ID NO:6 and NP_006088.2 is shown as SEQ ID NO:2.

FIG. 4A shows the results of hematoxylin/eosin staining (HE staining) and PAS staining after administration of anti-mouse/human Myl9 monoclonal antibody (Antibody A) to mice with induced airway inflammation. FIG. 4B shows the number of infiltrating cells seen in the bronchoalveolar lavage fluid and infiltrating cell types after administration of anti-mouse/human Myl9 monoclonal antibody (Antibody A) to mice with induced airway inflammation. FIG. 4C shows the amount of cytokine produced after administration of anti-mouse/human Myl9 monoclonal antibody (Antibody A) to mice with induced airway inflammation.

FIGS. 7A-7B show each of the comparison of amino acid sequences between mouse Myl9, mouse Myl12a and mouse Myl12b (FIG. 7A) and the comparison of amino acid sequences between human Myl9, human Myl12a and human Myl12b (FIG. 7B). *: conserved amino acid; -: gap; underline: amino acid sequence of a peptide used for immunization for mice to prepare Antibody A. In FIG. 7A, NP_742116.1 is shown as SEQ ID NO:1, NP_080340.2 is shown as SEQ ID NO:93, and NP_075891.1 is shown as SEQ ID NO:94. In FIG. 7B, NP_006088.2 is shown as SEQ ID NO:2, NP_001289976.1 is shown as SEQ ID NO:95, and NP_001138416.1 is shown as SEQ ID NO:96.

DESCRIPTION OF EMBODIMENTS

Figure 1C:
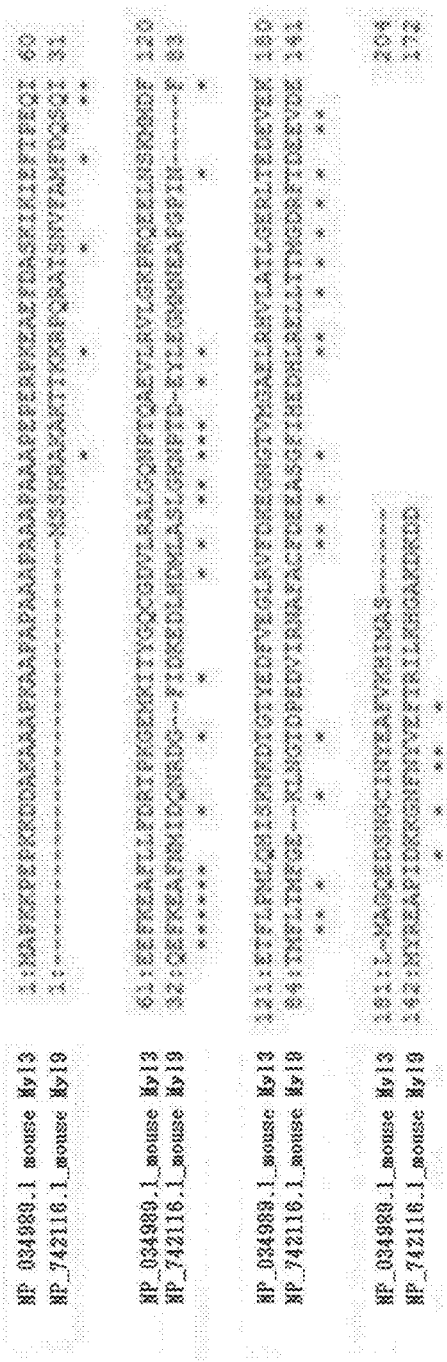
FIGS. 1C-1D show each of the comparison of amino acid sequences between mouse Myl3 and mouse Myl9 (FIG. 1C) and the comparison of amino acid sequences between human Myl3 and human Myl9 (FIG. 1D). *: conserved amino acid; -: gap.

The present invention relates to an anti-Myl9 antibody that binds to myosin regulatory light chain polypeptide (hereinbelow described as Myl)9.

The anti-Myl9 antibody used in the present invention is an antibody that can recognize and bind to Myl9, and as described below, said antibody may be an intact antibody. Alternatively, the anti-Myl9 antibody used in the present invention may be a recombinant antibody (such as a chimeric antibody, a humanized antibody, or a human antibody) or a chemically synthesized antibody, as well as an antigen binding fragment thereof, as long as it possesses the binding affinity to Myl9. Myl9 herein can be understood to refer to Myl9 derived from human or mouse. The amino acid sequence of Myl9 derived from human or mouse can be obtained from public databases where gene and amino acid sequence information are registered such as Genbank provided by U.S. National Center for Biotechnology Information, or the amino acid sequence can be determined from the sequence information of the Myl9 gene that is obtained by designing a primer based on the base sequence information of Myl9 of a closely related animal species and cloning from the RNA extracted from the desired animal species. For example, the amino acid sequence information of human and mouse Myl9 is registered in the database as Genbank Accession No. NP_006088.2 (SEQ ID NO. 2) and Genbank Accession No. NP_742116.1 (SEQ ID NO. 1), respectively.

In one aspect of the present invention, Myl9 comprises a peptide represented by the amino acid sequence set forth in SEQ ID NO. 1, or a peptide represented by an amino acid sequence having one or multiple amino acids substitution, addition, or deletion in said amino acid sequence. "Multiple" as used herein in reference to Myl9 is not limited as long as functional properties equivalent to those of a peptide represented by the original amino acid sequence thereof are retained, and is 2 to 20, for example 2 to 15, 2 to 10, 2 to 9, 2 to 8, 2 to 7, 2 to 6, or 2 to 5. In another aspect of the present invention, Myl9 comprises a peptide represented by an amino acid sequence that has at least 90%, for example 91%, 92%, 93%, 94%, or 95% homology with the amino acid sequence set forth in SEQ ID NO. 1.

As used herein, the "homology" of the amino acid sequence means a homology calculated by Pairwise Alignment using CLUSTALW algorithm under the following parameter setting:
K-tuple (word) size: 1
Window size: 5
Gap Penalty: 3
Number of Top Diagonals: 5
Scoring Method: PERCENT In one aspect of the present invention, Myl9 comprises a peptide represented by the amino acid sequence set forth in SEQ ID NO. 2, or a peptide represented by an amino acid sequence having one or multiple amino acids substitution, addition, or deletion in said amino acid sequence. "Multiple" as used herein in reference to Myl9 is not limited as long as functional properties equivalent to those of a peptide represented by the original amino acid sequence thereof are retained, and is 2 to 20, for example 2 to 15, 2 to 10, 2 to 9, 2 to 8, 2 to 7, 2 to 6, or 2 to 5. In another aspect of the present invention, Myl9 comprises a peptide represented by an amino acid sequence that has at least 90%, for example 91%, 92%, 93%, 94%, or 95% homology with the amino acid sequence set forth in SEQ ID NO. 2.

In one aspect of the present invention, Myl9 comprises a peptide represented by the amino acid sequence set forth in SEQ ID NO. 3, or a peptide represented by an amino acid sequence having one or multiple amino acids substitution, addition, or deletion in said amino acid sequence. "Multiple" as used herein in reference to Myl9 is not limited as long as functional properties equivalent to those of a peptide represented by the original amino acid sequence thereof are retained, and is 2 to 20, for example 2 to 15, 2 to 10, 2 to 9, 2 to 8, 2 to 7, 2 to 6, or 2 to 5. In another aspect of the present invention, Myl9 comprises a peptide represented by an amino acid sequence that has at least 90%, for example 91%, 92%, 93%, 94%, or 95% homology with the amino acid sequence set forth in SEQ ID NO. 3.

In one aspect of the present invention, the amino acid sequences of mouse Myl9 and mouse Myl12a, and mouse Myl9 and mouse Myl12b have 94.2% and 93.6% homology, respectively, and mouse Myl12a and mouse Myl12b have 97.7% homology. The amino acid sequences of human Myl9 and human Myl12a, and human Myl9 and human Myl12b have 91.8% and 93.0% homology, respectively, and human Myl12a and human Myl12b have 96.5% homology. For this reason, an antibody that recognizes Myl9 sometimes recognizes Myl12a. Moreover, an antibody that recognizes Myl9 sometimes recognizes Myl12b. Thus, in one embodiment of the present invention, the anti-Myl9 antibody or Myl9 binding fragment thereof of the present invention can also recognize Myl12a and/or Myl12b.

In one aspect of the present invention, the anti-Myl9 antibody or Myl9 binding fragment thereof of the present invention is an antibody that inhibits the binding between Myl9 and the extracellular region of CD69. For example, the anti-Myl9 antibody or Myl9 binding fragment thereof of the present invention may be an antibody or an antigen binding fragment that inhibits the binding between any portion of CD69 extracellular region and Myl9 that comprises a peptide represented by the amino acid sequence set forth in SEQ ID NO. 4 or a peptide represented by an amino acid sequence having one or multiple amino acids substitution, addition, or deletion in said amino acid sequence. "Multiple" as used herein in reference to the extracellular region of CD69 is, but is not limited to, 2 to 15, for example 2 to 14, 2 to 13, 2 to 12, 2 to 11, 2 to 10, 2 to 9, 2 to 8, 2 to 7, 2 to 6, or 2 to 5. In another aspect of the present invention, the anti-Myl9 antibody or Myl9 binding fragment thereof of the present invention may be an antibody or an antigen binding fragment that inhibits the binding between any portion of CD69 extracellular region that comprises a peptide represented by an amino acid sequence that has at least 90%, for example 91%, 92%, 93%, 94%, or 95% homology with the amino acid sequence set forth in SEQ ID NO. 4 and Myl9.

In another aspect of the present invention, the anti-Myl9 antibody or Myl9 binding fragment thereof of the present invention is an antibody that inhibits the binding between Myl12a and/or Myl12b and the extracellular region of CD69. For example, the anti-Myl9 antibody or Myl9 binding fragment thereof of the present invention may be an antibody or an antigen binding fragment that inhibits the binding between any portion of CD69 extracellular region that comprises a peptide represented by the amino acid sequence set forth in SEQ ID NO. 97 or a peptide represented by an amino acid sequence having one or multiple amino acids substitution, addition, or deletion in said amino acid sequence and Myl12a and/or Myl12b. In another aspect of the present invention, the anti-Myl9 antibody or Myl9 binding fragment thereof of the present invention may be an antibody or an antigen binding fragment that inhibits the binding between any portion of CD69 extracellular region that comprises a peptide represented by an amino acid sequence that has at least 90%, for example 91%, 92%, 93%, 94%, or 95% homology with the amino acid sequence set forth in SEQ ID NO. 97 and Myl12a and/or Myl12b.

In one aspect of the present invention, the anti-Myl9 antibody or Myl9 binding fragment thereof can bind to Myl9 of a mammal (e.g. rodents such as mouse, rat, or rabbit, monkey, cow, horse, goat, human, and the like) to inhibit the interaction between Myl9 and CD69, and preferably can bind to human Myl9 to inhibit the interaction between human Myl9 and human CD69. "Inhibits the interaction between Myl9 and CD69" herein means disappearance or lowering of the interaction between Myl9 and CD69. The interaction between Myl9 and CD69 can be evaluated by measuring the change in CD69 function that is caused as a result of Myl9 and CD69 acting under coexistence (e.g. expression or enhancement of CD69 function, or physiological function resulting from change in CD69 function due to the action of Myl9) or measuring the migration of CD4T cells that have expressed CD69 to bone marrow.

In another aspect of the present invention, the anti-Myl9 antibody or Myl9 binding fragment thereof can also bind to Myl12a and/or Myl12b of a mammal (e.g. rodents such as mouse, rat, or rabbit, monkey, cow, horse, goat, human, and the like) to inhibit the interaction between Myl12a and/or Myl12b and CD69, and preferably can also bind to human Myl12a and/or human Myl12b to inhibit the interaction between human Myl12a and/or human Myal12b and human CD69. "Inhibits the interaction between Myl12a and/or Myl12b and CD69" herein means disappearance or lowering of the interaction between Myl12a and/or Myl12b and CD69. The interaction between Myl12a and/or Myl12b and CD69 can be evaluated by measuring the change in CD69 function that is caused as a result of Myl12a and/or Myl12b and CD69 acting under coexistence (e.g. expression or enhancement of CD69 function, or physiological function resulting from change in CD69 function due to the action of Myl12a and/or Myl12b) or measuring the migration of CD4T cells that have expressed CD69 to bone marrow.

The method employed for measuring the antigen binding property (such as binding affinity and cross-species reactivity) of the antibody or an antigen binding fragment thereof may be a method well-known in the field to those skilled in the art. For example, binding affinity may be measured with, but is not limited to, Biacore® biosensor, KinExA biosensor, scintillation proximity assay, ELISA, ORIGEN immunoassay (IGEN Inc.), flow cytometry, fluorescence quenching, fluorescence transition, yeast display, or immunostaining and the like. The neutralizing activity of the antibody or an antigen binding fragment thereof against the binding between Myl9 and CD69 may be measured with, but is not limited to, Biacore® biosensor, ELISA, or flow cytometry and the like.

The anti-Myl9 antibody or Myl9 binding fragment thereof of the present invention may preferably be any of a monoclonal antibody, a polyclonal antibody, or a Myl9 binding fragment thereof that binds to Myl9 or other peptide molecules having the amino acid sequence of the binding region of Myl9 against said antibody.

A monoclonal antibody herein may mean an antibody that is obtained from a population of substantially uniform antibodies. In other words, individual antibodies contained in said population are identical except for a slight amount of naturally existing mutants that may be present. A monoclonal antibody is directed against a single antigen site. Further, in contrast to a typical polyclonal antibody that targets different antigens or different epitopes, each monoclonal antibody targets a single epitope of an antigen. The modifier "monoclonal" indicates the property of an antibody that is obtained from a substantially uniform antibody population, and is not to be understood as being limited to requiring production of the antibody by a particular method.

The anti-Myl9 antibody or Myl9 binding fragment thereof of the present invention herein may be of any class such as IgG, IgA, or IgM (or a subclass thereof), and is not limited to a particular class. Immunoglobulins are classified into different classes depending on the antibody amino acid sequence of the constant region of the heavy chain (sometimes referred to as the H chain). There are five major immunoglobulin classes: IgA, IgD, IgE, IgG and IgM, some of which may be further subdivided into subclasses (isotypes) such as $IgG_1$, $IgG_2$, $IgG_3$, $IgG_4$, $IgA_1$, and $IgA_2$. The constant region of the heavy chain corresponding to the different classes of immunoglobulin are referred to as $\alpha$, $\delta$, $\varepsilon$, $\gamma$, and $\mu$, respectively. Moreover, the types of light chain (sometimes referred to as the L chain) of an antibody include $\lambda$ and $\kappa$ chains.

In one aspect, the anti-Myl9 antibody or Myl9 binding fragment thereof of the present invention may be an IgG antibody, for example an $IgG_1$ antibody or an $IgG_2$ antibody and the like. Moreover, the anti-Myl9 antibody or Myl9 binding fragment thereof of the present invention may be in the form of a monomer, a dimer, or a multimer.

A Myl9 binding fragment herein is a functional and structural fragment of an anti-Myl9 antibody, and is not particularly limited as long as it possesses the binding ability to Myl9. Examples of such a Myl9 binding fragment can include, but are not limited to, Fab, Fab', $F(ab')_2$, Fv, single-chain (scFv), variants thereof, a fusion protein or a fusion peptide comprising an antibody portion, other modified structures of an immunoglobulin molecule comprising the Myl9 recognition site, and the like.

The Myl9 binding fragment of an anti-Myl9 antibody can be obtained via proteolytic digestion of a complete antibody by e.g. a protease such as papain or pepsin, or may be directly produced by a recombinant host cell (e.g. a eukaryote such as an yeast cell, a plant cell, an insect cell, or a mammalian cell, or a prokaryote such as *E. coli*). For example, an $F(ab')_2$ fragment may be formed by directly collecting Fab'-SH fragments from *E. coli* and subjecting them to chemical binding. $F(ab')_2$ may also be formed by using a leucine zipper GCN4 which promotes the assembly of $F(ab')_2$ molecules. Moreover, an automatic synthesizer can be used when a scFv is produced by a chemical synthesis technology. When a scFv is produced by a genetic recombination technology, an appropriate plasmid comprising a polynucleotide encoding the scFv can be introduced into an appropriate host cell (e.g. a eukaryote such as an yeast cell, a plant cell, an insect cell, or a mammalian cell, or a prokaryote such as *E. coli*). The polynucleotide encoding the scFv of interest may be produced by a well-known operation such as polynucleotide ligation. The scFv produced as a result may be isolated using a standard protein purification technology well-known in the art.

A variable region of an antibody herein means the variable region of an antibody light chain, the variable region of an antibody heavy chain, or both. Moreover, a constant region of an antibody herein means the constant region of an antibody light chain, the constant region of an antibody heavy chain, or both. The variable region of heavy and light chains each consists of four framework regions (FR) connected by three CDRs also known as hypervariable regions. The CDRs in each chain are retained in vicinity by FRs, and together with CDRs in the other chain contribute to the formation of the antigen binding site of the antibody. The technology for determining the CDR can include, but is not limited to, e.g. (1) an approach based on cross-species sequence variability (such as Kabat et al, Sequences of Proteins of Immunological Interest, 5th ed., 1991, National Institutes of Health, Bethesda Md.); and (2) an approach based on the crystal structure research of antigen-antibody complexes (Al-lazikani et al., 1997 J. Molec. Biol. 273:927-948). These or other approaches may be employed in combination.

The anti-Myl9 antibody or Myl9 binding fragment thereof of the present invention is a recombinant antibody (such as a chimeric antibody, a humanized antibody, or a human antibody) or a chemically synthesized antibody, a non-human mammal (e.g. rodents such as mouse, rat, or rabbit, monkey, cow, horse, goat, and the like) antibody, or a Myl9 binding fragment thereof. The anti-Myl9 antibody or Myl9 binding fragment thereof of the present invention is a humanized or chimeric antibody, preferably a humanized antibody. A chimeric antibody is e.g. an antibody wherein the variable region of a non-human (such as mouse or rat) antibody is introduced into the constant region of a human antibody, and for example refers to an antibody where the variable region is derived from a non-human antibody and the constant region is derived from a human antibody. A humanized antibody is e.g. an antibody wherein the hypervariable region of a non-human antibody is introduced into a human antibody, and for example refers to an antibody where the CDR is derived from a non-human antibody and the remaining antibody regions are derived from a human antibody. Note that in the present invention, the boundary between a chimeric antibody and a humanized antibody does not necessarily need to be clear, and an antibody may be in a state that may be called a chimeric antibody or a humanized antibody. An aspect of a preferred humanized antibody herein is an antibody wherein the CDR is derived from a rodent antibody and the remaining antibody regions are derived from a human antibody, particularly preferably an antibody where the CDR is derived from a mouse antibody and the remaining antibody regions are derived from a human antibody. Humanization can also be carried out by introducing the CDR sequence derived from an antibody of e.g. a rodent into the corresponding site of a human antibody with a CDR grafting method (see Jones et al., Nature 321:522-525(1986); Riechmann et al., Nature 332:323-327 (1988); and Verhoeyen et al., Science 239:1534-1536(1988); Kontermann and Dubel, Antibody Engineering, Springer Lab Manual (2001) and Tsurushita et al., Methods 36:69-83(2005)). In some cases, a humanized antibody may also be a humanized antibody where several amino acid residues in the are substituted by amino acid residues derived from a similar site in a non-human antibody.

It may be important in order to decrease antigenicity that the use of human variable regions is selected for both light and heavy chains in the production of a humanized antibody. The amino acid sequence of the variable region of rodents such as mouse, rat, or rabbit antibody is screened against the entire library of known human FR sequences. Next, the amino acid sequence of a human antibody that is the closest to the sequence of the rodent antibody is accepted as the human FR of the humanized antibody. For example, O'Brien and Jones, Antibody Engineering (Springer Lab Manual), 567-590 can be used as reference. In another method, a particular framework derived from a sequence common to all human antibodies in a particular subgroup of the light or heavy chain is employed. The same framework may be employed for several different humanized antibodies. For example, Carter et al., Proc. Natl. Acad. Set USA 89:4285-4289(1992) and Presta et al., J. Immunol. 151:2623-2632 (1993) can be used as reference.

Further, it is desirable that the humanized antibody in general retains the high binding affinity against antigens and other preferred biological natures. In order to achieve this objective, according to one method, the humanized antibody is prepared by a step of analyzing the parent sequence and various conceptual humanized products employing a three dimensional model of the parent sequence and the humanized sequence. In general, a three dimensional immunoglobulin model is available for use and is known to those skilled in the art. A computer program that illustrates and displays a potential three dimensional conformation of a selected candidate immunoglobulin sequence is available for use. By investigating these illustrated three dimensional conformations, analysis of amino acid residues that influence the ability of the candidate immunoglobulin to bind to its antigen is possible. By this method, FR residues can be designed such that desirable antibody property such as retention of the binding affinity against a single or multiple target antigen(s) (such as Myl9 or a fragment thereof) is achieved.

An antibody in which the chimeric or humanized antibody exemplified above is appropriately altered (e.g. modification of the antibody, or partial substitution, addition, or deletion of the amino acid sequence of the antibody) while retaining the function of said antibody (or in order to add or improve the function of said antibody) is also encompassed in the antibody of the present invention. Specifically, an antibody where lysine (Lys) located at the carboxy terminal (C-terminal) of the heavy chain is deleted by an artificial method such as genetic modification in order to reduce the ununiformity of antibodies produced by antibody-producing cells is also encompassed in the scope of the present invention. Examples of other partial substitution can include, but are not limited to, an antibody where the amino acid residue at position 234 in the heavy chain is mutated from valine (V) to alanine (A), an antibody where the amino acid residue at position 237 in the heavy chain is mutated from glycine (G) to alanine (A), as well as a combination thereof and the like. Note that said mutations are described herein as V234A and G237A, respectively.

The anti-Myl9 antibody or Myl9 binding fragment thereof of the present invention may be modified as desired. The modification of the anti-Myl9 antibody or Myl9 binding fragment thereof of the present invention may be a modification that changes (a) the three dimensional structure of the amino acid sequence at the modified region such as sheet or helix conformation; (b) the charge or hydrophobicity state of the molecule at the target site; or (c) the effect of modification on the maintenance of side chain volume, or alternatively a modification where these changes are not plainly observed can be implemented.

The modification of the anti-Myl9 antibody or Myl9 binding fragment thereof of the present invention can be achieved by e.g. substitution, deletion, addition, and the like of the configuring amino acid residues.

An amino acid herein is employed in its broadest meaning, and includes not only natural amino acids such as serine (Ser), asparagine (Asn), valine (Val), leucine (Leu), isoleucine alanine (Ala), tyrosine (Tyr), glycine (Gly), lysine (Lys), arginine (Arg), histidine (His), aspartic acid (Asp), glutamic acid (Glu), glutamine (Gin), threonine (Thr), cysteine (Cys), methionine (Met), phenylalanine (Phe), tryptophan (Trp), and proline (Pro), but also non-natural amino acids such as amino acid variants and derivatives. Those skilled in the art shall recognize that in light of this broad definition, examples of amino acids herein can include L-amino acids; D-amino acids; chemically modified amino acids such as amino acid variants and derivatives; amino acids that are not materials configuring proteins in vivo such as norleucine, β-alanine, and ornithine; and chemically synthesized compounds having properties of amino acids well-known to those skilled in the art. Examples of a non-natural amino acid can include α-methylamino acids (such as α-methylalanine), D-amino acids (such as D-aspartic acid and D-glutamic acid), histidine-like amino acids (such as 2-amino-histidine, β-hydroxy-histidine, homohistidine, α-fluoromethyl-histidine, and α-methyl-histidine), amino acids having excess methylene in the side chain (homoamino acids), and amino acids where the carboxylate functional group amino acid in the side chain is substituted with a sulfonate group (such as cysteic acid).

Naturally-occurring amino acid residues may be e.g. classified into the following groups based on general side chain properties:
(1) Hydrophobic: Met, Ala, Val, Leu, and Ile;
(2) Neutral hydrophilic: Cys, Ser, and Thr;
(3) Acidic: Asp and Glu;
(4) Basic: Asn, Gin, His, Lys, and Arg;
(5) Residues that influence chain orientation: Gly and Pro; and
(6) Aromatic: Trp, Tyr, and Phe.

A nonconservative substitution of the amino acid sequence configuring an antibody or an antigen binding fragment thereof may be performed by exchanging an amino acid that belongs to one of these groups with an amino acid that belongs to another group. A more conservative substitution may be performed by exchanging an amino acid that belongs to one of these groups with another amino acid that belongs to the same group. Similarly, deletion or substitution of the amino acid sequence may be appropriately performed.

A modification of the amino acid configuring the antibody or an antigen binding fragment thereof may be e.g. a post-translational modification such as glycosylation by a sugar, acetylation, or phosphorylation. The antibody may be glycosylated at a conserved position in its constant region. Glycosylation of an antibody is ordinarily either N-linked or O-linked. N-linked means linking of a sugar moiety to the side chain of an asparagine residue. Tripeptide sequences asparagine-X-serine, asparagine-X-threonine, and asparagine-X-cysteine (wherein X is any amino acid other than proline) are recognition sequences for enzymatically adding a sugar moiety to the asparagine side chain. A potential glycosylation site is present when any of these tripeptide sequences is present in the antibody or an antigen binding fragment thereof. O-linked glycosylation may be the linking of either N-acetylgalactosamine, galactose, or xylose to a hydroxy amino acid (such as serine or threonine), and in some instances may be the linking to 5-hydroxy praline or 5-hydroxy lysine. The glycosylation condition (e.g. when glycosylation is performed with a biological means, the type of host cell or cell medium, pH, and the like) can be appropriately selected by those skilled in the art according to the purpose.

The anti-Myl9 antibody or Myl9 binding fragment thereof of the present invention may be further modified based on technical common sense well-known to those skilled in the art by other modification methods alone or in combination.

The anti-Myl9 antibody or Myl9 binding fragment thereof of the present invention may be produced by a method well-known to those skilled in the art. For example, the antibody may be produced with a hybridoma that produces the Myl9 antibody or Myl9 binding fragment thereof of the present invention, or the antibody may be produced by integrating the gene encoding the anti-Myl9 antibody or Myl9 binding fragment thereof of the present invention into an expression vector and introducing said expression vector into E. coli cells, monkey COS cells, Chinese hamster ovary (CHO) cells, and the like. The gene encoding the anti-Myl9 antibody or Myl9 binding fragment thereof of the present invention preferably possesses a DNA encoding a signal sequence, and more preferably possesses a DNA encoding a signal sequence at the 5' terminal of the DNA encoding the heavy chain variable region and the DNA encoding the light chain variable region. A signal sequence is amino acid residues that are present at the N-terminal of a protein which is necessary for a secretory protein or an integral membrane protein to pass through the lipid bilayer after it is synthesized on the ribosome. A signal sequence herein is not particularly limited as long as it is a sequence possessing this function. A signal sequence that may be contained in the anti-Myl9 antibody or Myl9 binding fragment thereof of the present invention can include signal sequences derived from human, mouse, rat, rabbit, donkey, goat, horse, avian, dog, cat, yeast, and the like. One specific aspect of the signal sequence can include a peptide comprising the amino acid sequence represented by SEQ ID NO. 12 as the signal sequence related to the heavy chain and a peptide comprising the amino acid sequence represented by SEQ ID NO. 14 as the signal sequence related to the light chain. Moreover, substitution, addition, or deletion of one or multiple (such as 2, 3, 4, or 5) amino acids may be present in the amino acid sequence represented by SEQ ID NO. 12 or the amino acid sequence represented by SEQ ID NO. 14 as long as it is functionally equivalent.

The anti-Myl9 antibody or Myl9 binding fragment thereof of the present invention may be those that are isolated or purified according to methods well-known to those skilled in the art. Here, "isolated." or "purified" means that it is artificially isolated or purified from the natural state. When a molecule or a composition is naturally occurring, it means that it is "isolated" or "purified" when it has changed or is removed from an environment it originally exists, or both. Examples of an isolation or purification method can include, but are not limited to, electrophoresis, molecular biological, immunological, or chromatographic means and the like, specifically, ion exchange chromatography, hydrophobic chromatography, or reverse phase HPLC chromatography, or isoelectric focusing and the like.

An "immune checkpoint inhibitor" herein means an inhibitor against an immune checkpoint molecule that participates in an immune checkpoint mechanism, a system to suppress T cell activation, and includes a PD-1 inhibitor and a CTLA-4 inhibitor. The term "immune checkpoint molecule" encompasses both receptors and ligands that function as immune checkpoints.

The term "used in combination with an immune checkpoint inhibitor" herein means that a pharmaceutical composition comprising the anti-Myl9 antibody or Myl9 binding fragment thereof of the present invention and a pharmaceutically acceptable carrier or additive is administered to a patient with tumor with an immune checkpoint inhibitor around the same time as part of a therapeutic regimen. The pharmaceutical composition and the immune checkpoint inhibitor may be administered to the patient simultaneously, separately, continuously, or at time intervals with an effective amount of each when administered in combination. The therapeutic regimen may include another anti-cancer agent. The pharmaceutical composition and the immune checkpoint inhibitor may be administered to the patient in separate administration cycles. If the pharmaceutical composition and the immune checkpoint inhibitor are administered simultaneously, a single combination preparation comprising these may be administered.

A "PD-1 inhibitor" herein means a substance that directly or indirectly acts on PD-1 to inhibit T cell suppression action of PD-1. The PD-1 inhibitor includes a low-molecular compound, a peptide and an anti-PD-1 antibody that binds to PD-1 to inhibit its T cell suppression action as well as a low-molecular compound, a peptide and an anti-PD-L1 antibody that binds to PD-L1 and inhibit its PD-1 binding activity to inhibit T cell suppression action of PD-1. The anti-PD-1 antibody is not limited to, but includes pembrolizumab, nivolumab and MEDI0680 (AMP-514). The anti-PD-L1 antibody is not limited to, but includes atezolizumab, durvalumab and avelumab.

A "CTLA-4 inhibitor" herein means a substance that acts on CTLA-4 to inhibit T cell suppression action of CTLA-4. The CTLA-4 inhibitor includes a low-molecular compound, a peptide and an anti-CTLA-4 antibody that binds to CTLA-4 to inhibit its T cell suppression action. The anti-CTLA-4 antibody is not limited to, but includes ipilimumab and tremelimumab.

"Malignant lymphoma" herein means a group of blood malignant tumor that develops from lymphatic tissues. Malignant lymphoma includes Hodgkin's lymphoma and non-Hodgkin's lymphoma and the latter includes diffuse large B-cell lymphoma and the like.

"Head and neck cancer" herein means a general term of malignant tumor that develops in the region from the face to the neck and includes squamous cell cancer of the head and neck as part.

"Urothelial cancer" herein means epithelial malignant tumor that develop from urothelial cells and includes renal pelvic cancer, urinary tract cancer and bladder cancer as narrower terms.

"Breast cancer" herein means a carcinoma that develops in mammary tissues. Part of breast cancer is triple negative breast cancer that does not express estrogen receptors, progesterone receptors and human epidermal growth factor receptor 2 (HER-2).

In another preferred embodiment of the present invention, the anti-Myl9 antibody or Myl9 binding fragment thereof has the following CDR:

(a) a heavy chain CDR1 consisting of a peptide represented by the amino acid sequence set forth in SEQ ID NO. 28;

(b) a heavy chain CDR2 consisting of a peptide represented by the amino acid sequence set forth in SEQ ID NO. 30;

(c) a heavy chain CDR3 consisting of a peptide represented by the amino acid sequence set forth in SEQ ID NO. 32;

(d) a light chain CDR1 consisting of a peptide represented by the amino acid sequence set forth in SEQ ID NO. 33;

(e) a light chain CDR2 consisting of a peptide represented by the amino acid sequence set forth in SEQ ID NO. 34; and (f) a light chain CDR3 consisting of a peptide represented by the amino acid sequence set forth in SEQ ID NO. 35.

In another preferred embodiment of the present invention, the anti-Myl9 antibody or Myl9 binding fragment thereof comprises heavy and light chains, the variable region of said heavy chain comprises a peptide represented by the amino acid sequence set forth in SEQ ID NOs. 55, 56, 57, 58, 59, 60, 61, 62, 63, or 64, and the variable region of said light chain comprises a peptide represented by the amino acid sequence set forth in SEQ ID NOs. 65, 66, 67, or 68.

The amino acid sequence of the variable region of said heavy or light chain may comprise substitution, addition, or deletion of one or multiple amino acids in said sequence. "Multiple" as used herein is not limited as long as binding affinity against Myl9 is retained and the interaction between Myl9 and CD69 is inhibited, and is 2 to 15, more preferably 2 to 10, for example 9, 8, 7, 6, 5, 4, 3, or 2. Alternatively, the amino acid sequence of the variable region of said heavy or light chain comprises a peptide represented by an amino acid sequence that has at least 90%, for example 91%, 92%, 93%, 94%, or 95% homology with said sequence.

In another preferred embodiment of the present invention, the anti-Myl9 antibody or Myl9 binding fragment thereof is an antibody that comprises heavy chain and light chain variable regions consisting of the following combinations.

(1) an antibody comprising a heavy chain variable region comprising a peptide represented by the amino acid sequence set forth in SEQ ID NO. 64 and a light chain variable region comprising a peptide represented by the amino acid sequence set forth in SEQ ID NO. 66;

(2) an antibody comprising a heavy chain variable region comprising a peptide represented by the amino acid sequence set forth in SEQ ID NO. 63 and a light chain variable region comprising a peptide represented by the amino acid sequence set forth in SEQ ID NO. 66;

(3) an antibody comprising a heavy chain variable region comprising a peptide represented by the amino acid sequence set forth in SEQ ID NO. 56 and a light chain variable region comprising a peptide represented by the amino acid sequence set forth in SEQ ID NO. 66;

(4) an antibody comprising a heavy chain variable region comprising a peptide represented by the amino acid sequence set forth in SEQ ID NO. 57 and a light chain variable region comprising a peptide represented by the amino acid sequence set forth in SEQ ID NO. 66;

(5) an antibody comprising a heavy chain variable region comprising a peptide represented by the amino acid sequence set forth in SEQ ID NO. 55 and a light chain variable region comprising a peptide represented by the amino acid sequence set forth in SEQ ID NO. 66;

(6) an antibody comprising a heavy chain variable region comprising a peptide represented by the amino acid sequence set forth in SEQ ID NO. 58 and a light chain variable region comprising a peptide represented by the amino acid sequence set forth in SEQ ID NO. 66;

(7) an antibody comprising a heavy chain variable region comprising a peptide represented by the amino acid sequence set forth in SEQ ID NO. 59 and a light chain variable region comprising a peptide represented by the amino acid sequence set forth in SEQ ID NO. 66;

(8) an antibody comprising a heavy chain variable region comprising a peptide represented by the amino acid sequence set forth in SEQ ID NO. 60 and a light chain variable region comprising a peptide represented by the amino acid sequence set forth in SEQ ID NO. 66;

(9) an antibody comprising a heavy chain variable region comprising a peptide represented by the amino acid sequence set forth in SEQ ID NO. 61 and a light chain variable region comprising a peptide represented by the amino acid sequence set forth in SEQ ID NO. 66;

(10) an antibody comprising a heavy chain variable region comprising a peptide represented by the amino acid sequence set forth in SEQ ID NO. 64 and a light chain variable region comprising a peptide represented by the amino acid sequence set forth in SEQ ID NO. 68;

(11) an antibody comprising a heavy chain variable region comprising a peptide represented by the amino acid sequence set forth in SEQ ID NO. 63 and a light chain variable region comprising a peptide represented by the amino acid sequence set forth in SEQ ID NO. 68;

(12) an antibody comprising a heavy chain variable region comprising a peptide represented by the amino acid sequence set forth in SEQ ID NO. 56 and a light chain variable region comprising a peptide represented by the amino acid sequence set forth in SEQ ID NO. 68;

(13) an antibody comprising a heavy chain variable region comprising a peptide represented by the amino acid sequence set forth in SEQ ID NO. 57 and a light chain variable region comprising a peptide represented by the amino acid sequence set forth in SEQ ID NO. 68;

(14) an antibody comprising a heavy chain variable region comprising a peptide represented by the amino acid sequence set forth in SEQ ID NO. 55 and a light chain variable region comprising a peptide represented by the amino acid sequence set forth in SEQ ID NO. 68;

(15) an antibody comprising a heavy chain variable region comprising a peptide represented by the amino acid sequence set forth in. SEQ ID NO. 58 and a light chain variable region comprising a peptide represented by the amino acid sequence set forth in SEQ ID NO. 68;

(16) an antibody comprising a heavy chain variable region comprising a peptide represented by the amino acid sequence set forth in SEQ ID NO. 59 and a light chain variable region comprising a peptide represented by the amino acid sequence set forth in SEQ ID NO. 68;

(17) an antibody comprising a heavy chain variable region comprising a peptide represented by the amino acid sequence set forth in SEQ ID NO. 60 and a light chain variable region comprising a peptide represented by the amino acid sequence set forth in SEQ ID NO. 68;

(18) an antibody comprising a heavy chain variable region comprising a peptide represented by the amino acid sequence set forth in SEQ ID NO. 61 and a light chain variable region comprising a peptide represented by the amino acid sequence set forth in SEQ ID NO. 68;

(19) an antibody comprising a heavy chain variable region comprising a peptide represented by the amino acid sequence set forth in SEQ ID NO. 62 and a light chain variable region comprising a peptide represented by the amino acid sequence set forth in SEQ ID NO. 65;

(20) an antibody comprising a heavy chain variable region comprising a peptide represented by the amino acid sequence set forth in SEQ ID NO. 62 and a light chain variable region comprising a peptide represented by the amino acid sequence set forth in SEQ ID NO. 67;

(21) an antibody comprising a heavy chain variable region comprising a peptide represented by the amino acid sequence set forth in SEQ ID NO. 62 and a light chain variable region comprising a peptide represented by the amino acid sequence set forth in SEQ ID NO. 66; and

(22) an antibody comprising a heavy chain variable region comprising a peptide presented by the amino acid sequence set forth in SEQ ID NO. 62 and a light chain variable region comprising a peptide represented by the amino acid sequence set forth in SEQ ID NO. 68.

In one aspect, the present invention relates to a pharmaceutical composition comprising the anti-Myl9 antibody or Myl9 binding fragment thereof of the present invention.

The pharmaceutical composition comprising the anti-Myl9 antibody or Myl9 binding fragment thereof of the present invention in an aqueous or dry preparation form may further comprise a pharmaceutically acceptable carrier, an excipient, and/or a stabilizer. Examples of an acceptable carrier, excipient, or stabilizer include saline; a buffer such as phosphoric acid, citric acid, or other organic acids; an antioxidant including ascorbic acid; a low molecular weight polypeptide; a protein (such as serum albumin, gelatin, or immunoglobulin); a hydrophilic polymer such as polyvinylpyrrolidone; an amino acid; monosaccharides, disaccharides, and other carbohydrates including glucose, mannose, or dextrins; a chelator such as EDTA; sugar alcohols such as mannitol or sorbitol; a counter ion that forms a salt such as sodium; or a nonionic surfactant such as TWEEN™, PLURONICS™, or PEG.

The pharmaceutical composition comprising the anti-Myl9 antibody or Myl9 binding fragment thereof of the present invention may be encapsulated e.g. in a microcapsule, in a colloidal drug delivery system (such as a liposome, an albumin microsphere, a microemulsion, a nanoparticle, or a nanocapsule), or in a macroemulsion. When sustained release administration of the antibody is desired in a preparation having release property suitable for any disease that requires administration of the antibody, microcapsulation of the antibody may be intended. Examples of a sustained release matrix include a polyester, a hydrogel (such as poly(2-hydroxyethyl-methacrylate) or poly(vinyl alcohol)), polylactic acids, a copolymer of L-glutamic acid and γ ethyl-L-glutamate, a nondegradable ethylene-vinyl acetate, a degradable lactic acid-glycolic acid copolymer such as LUPRON DEPOT™ (an injectable microsphere composed of lactic acid-glycolic acid copolymer and leuprolide acetate), and poly-D-(−)-3-hydroxy butyric acid.

As described above, the anti-Myl9 antibody or Myl9 binding fragment thereof of the present invention can inhibit the interaction between Myl9 and CD69. Accordingly, the pharmaceutical composition comprising the anti-Myl9 antibody or Myl9 binding fragment thereof of the present invention may be useful for treating a disease attributed to the interaction between Myl9 and CD69, e.g. allergic airway inflammation such as asthma, chronic allergic rhinitis, or some sinusitis, airway inflammation disease such as sinusitis not included in allergic airway inflammation, and inflammatory bowel disease such as ulcerative colitis, Crohn's disease, Behcet's disease, and eosinophilic gastrointestinal dysfunction. In other words, in another aspect, the present invention encompasses a method for treating airway inflammation disease or inflammatory bowel disease comprising a step of administering to a subject a therapeutically effective amount of the anti-Myl9 antibody or Myl9 binding fragment thereof of the present invention. Further, in another aspect, the present invention encompasses the use of the anti-Myl9 antibody or Myl9 binding fragment thereof of the present invention for manufacturing a therapeutic drug for airway inflammation disease or inflammatory bowel disease. In another aspect, the present invention encompasses the anti-Myl9 antibody or Myl9 binding fragment thereof for use in a method for treating airway inflammation disease or inflammatory bowel disease. Moreover, in another aspect, the present invention encompasses the anti-Myl9 antibody or Myl9 binding fragment thereof for manufacturing a pharmaceutical for treating airway inflammation disease or inflammatory bowel disease.

A pharmaceutical composition comprising the anti-Myl9 antibody or Myl9 binding fragment thereof of the present invention may be useful for treating tumor such as colorectal cancer, malignant melanoma, non-small cell lung cancer, renal cell carcinoma, malignant lymphoma, multiple myeloma, head and neck cancer, urothelial cancer, breast cancer, hepatocellular carcinoma, gastric cancer, esophageal cancer, ovarian cancer, small cell lung cancer, mesothelioma and endometrial cancer when it is in combination with an immune checkpoint inhibitor. In other words, in another aspect, the present invention encompasses a method for treating tumor comprising a step of administering to a subject a therapeutically effective amount of the anti-Myl9 antibody or Myl9 binding fragment thereof of the present invention wherein the anti-Myl9 antibody or Myl9 binding fragment thereof is administered to the subject in combination with the immune checkpoint inhibitor. Further, in another aspect, the present invention encompasses the use of the anti-Myl9 antibody or Myl9 binding fragment thereof of the present invention for manufacturing a therapeutic drug for tumor to be used in combination with the immune checkpoint inhibitor. In another aspect, the present invention encompasses the anti-Myl9 antibody or Myl9 binding fragment thereof for use in a method for treating tumor to be administered in combination with the immune checkpoint inhibitor. Moreover, in another aspect, the present invention encompasses the anti-Myl9 antibody or Myl9 binding fragment thereof for manufacturing a pharmaceutical for treating tumor to be used in combination with the immune checkpoint inhibitor.

When the pharmaceutical composition comprising the anti-Myl9 antibody or Myl9 binding fragment thereof of the present invention is used in combination with the immune checkpoint inhibitor for treating tumor, the anti-Myl9 antibody or Myl9 binding fragment thereof is preferably an antibody or a binding fragment thereof that also inhibits the interaction between Myl12a and/or Myl12b and CD69.

The anti-Myl9 antibody or Myl9 binding fragment thereof of the present invention can be employed in a therapeutic method alone or in combination with other agents or com-positions (in the method of treating tumor, the anti-Myl9 antibody or Myl9 binding fragment thereof of the present invention is administered in combination with the immune checkpoint inhibitor). For example, the anti-Myl9 antibody or Myl9 binding fragment thereof of the present invention may be administered at the same time or different times with another agent. Such a combination therapy comprises combined administration (two or more agents are contained in the same or separate preparation) and separate administration (e.g. at the same time or sequentially). When two or more agents are administered separately, the administration of the anti-Myl9 antibody or Myl9 binding fragment thereof of the present invention may be before or after the accompanying therapeutic method.

The subject to which the pharmaceutical composition comprising the anti-Myl9 antibody or Myl9 binding fragment thereof of the present invention is administered is not limited, and the present invention is employed for a human or a non-human mammal (rodents such as mouse, rat, or rabbit, monkey, cow, horse, goat, and the like).

The administration method of the pharmaceutical composition comprising the anti-Myl9 antibody or Myl9 binding fragment thereof of the present invention to a subject (such as administration route, dosage, frequency of administration per day, and administration timing) is not limited, and can be appropriately determined by those skilled in the art (such as a physician) according to the health state of the subject, the extent of disease, the type of agent used in combination, and the like.

As long as it is not technically contradicting, any one or more of any and all aspects described herein can be appropriately combined to carry out the present invention. Further, as long as it is not technically contradicting, it shall be preferred that any and all preferred or advantageous aspects described herein is appropriately combined to carry out the present invention.

All disclosures of the literatures cited herein should be deemed to be clearly incorporated herein by reference, and those skilled in the art can incorporate the disclosed content related to these literatures as part of the present specification according to the context herein without departing from the scope of the present invention.

The literatures cited herein are provided solely for the purpose of disclosing the related technology preceding the filing date of the present application, and are not to be construed as an admission by the present inventors that the present invention does not hold the right to precede said disclosures due to prior inventions or for any other reason. All description of these literatures are based on the information available to the present applicants, and do not in any way configure the acknowledgement that these descriptions are correct.

The terms used herein are employed for describing particular embodiments, and do not intend to limit the invention.

Unless the context clearly indicates to be understood otherwise, the term "comprise" as used herein intends the presence of the described items (such as components, steps, elements, or numbers), and does not exclude the presence of other items (such as components, steps, elements, and numbers). The term "consist of" encompasses aspects described by the terms "consist of" and/or "consist essentially of."

The term "neutralizing activity" as used herein means the activity to inhibit the binding between Myl9 and CD69, and/or the activity to lower signal transduction, molecular expression response or functionality change of the cell that is induced inside the human body due to the interaction between Myl9 and CD69.

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and should not be construed as having idealized or excessively formal meanings.

Terms such as first and second are employed to represent various elements, and it should be recognized that these elements are not to be limited by these terms themselves. These terms are employed solely for the purpose of discriminating one element from the other, and it is for example possible to describe a first element as a second element, and similarly, to describe a second element as a first element without departing from the scope of the present invention.

The numeric values employed herein for indicating component content or numeric value range and the like, unless explicitly indicated, are to be understood as being modified by the term "about." For example, unless explicitly indicated, "4° C." is recognized as meaning "about 4° C.," and those skilled in the art can naturally and reasonably recognize the extent thereof according to technical common sense and the context of the present specification.

Unless clearly indicated to mean otherwise in context, when used in the specification and claims herein, it should be recognized that each aspect represented in singular form may also be a plural form as long as it is not technically contradicting, and vice versa.

The present invention will now be described in further detail with reference to Examples. However, the present invention can be embodied by various aspects, and shall not be construed as being limited to the Examples described herein. Those skilled in the art of related technical fields can implement the present invention with various modifications, additions, deletions, substitution, and the like without altering the scope of the present invention.

EXAMPLES

Example 1: Production of Anti-Mouse/Human Myl9 Monoclonal Antibody

Production of Mouse Anti-Mouse/Human Myl9 Monoclonal Antibody

In order to produce a monoclonal antibody against mouse Myl9 (Genbank Accession No. NP_742116.1, SEQ ID NO. 1) and human Myl9 (Genbank Accession No. NP_006088.2, SEQ ID NO. 2), a peptide having cysteine (Cys) added to the C-terminal of the N-terminal sequence common to mouse Myl9 and human Myl9 (positions 1-27) (hereinbelow referred to as mouse/human Myl9 peptide) (SEQ ID NO. 3) and a protein having keyhole limpet hemocyanin (KLH) fused thereto (hereinbelow referred to as "mouse/human Myl9 peptide-KLH") were prepared by the following steps. Comparison of mouse Myl9 and human Myl9 sequences is shown in FIG. 1-1A.

First, mouse/human Myl9 peptide (SEQ ID NO. 3) was synthesized by consigning to TORAY Research Center, Inc., and mouse/human Myl9 peptide-KLH was produced with Imject Maleimide-Activated mcKLH Spin Kit (Thermo Fisher Scientific).

Ten micrograms of mouse/human Myl9 peptide-KLH was mixed with the same amount of GERBU adjuvant (GERBU Biotechnik GmbH), and subcutaneously injected into C57BL/6J mice footpad. Then, mouse/human Myl9 peptide-KLH was similarly administered on Days 3, 7, and 10. GERBU adjuvant (GERBU Biotechnik GmbH) was used on Days 3 and 10. Mice were sacrificed on Day 13, and peripheral lymph nodes were collected to prepare lymph node cells. In the presence of GenomeONE-CF (Ishihara Sangyo Kaisha, Ltd.), the lymph node cells prepared and P3U1 myeloma cells (endowed from Professor Jun Shimizu, Kyoto University) were fused at a proportion of 5:1. Said fused cells were cultured in a 96-well plastic plate. After 7 days of incubation (5% $CO_2$, 37° C.), the culture supernatant was collected.

With the culture supernatant obtained, wells having reactivity against mouse/human Myl9 peptide, as well as inhibitory activity against binding between mouse CD69 extracellular region protein and mouse Myl9 were picked up.

Reactivity against mouse/human Myl9 peptide was evaluated with a protein having bovine serum albumin (BSA) fused to mouse/human Myl9 peptide (SEQ ID NO. 3) (hereinbelow mouse/human Myl9 peptide-BSA) by ELISA. Mouse/human Myl9 peptide (SEQ ID NO. 3) was synthesized by consigning to TORAY Research Center, Inc., and mouse/human Myl9 peptide-BSA was produced with Imject Maleimide-Activated BSA Spin Kit (Thermo Fisher Scientific).

A plasmid encoding mouse CD69 extracellular region protein (positions 62-199) (SEQ ID NO. 4) having a Flag tag added to the N-terminal (hereinbelow 3× Flag-mouse CD69 EC) was endowed from Chiba University, and this was transfected into Expi293F cells (Invitrogen/LifeTechnologies) with ExpiFectamine 293 Transfection Kit (Thermo Fisher Scientific/Gibco). After 4 days of incubation (8% CO2, 37° C.), the culture supernatant was collected. From the collected culture supernatant, 3× Flag-mouse CD69 EC was purified with Anti-Flag M2 Affinity Gel (SIGMA). After purification, sugar chain cleaving treatment was performed with PNGase F (New England BioLabs).

For glutathione-S-transferase (GST)-His-mouse Myl9 (hereinbelow GST-His mouse Myl9), a plasmid endowed from Chiba University was expressed in *E. coli* BL21-Gold (DE3) pLys (Agilent Technologies) and purified with Glutathione Sepharose 4 Fast Flow (GE Healthcare).

ELISA employing mouse/human Myl9 peptide-BSA was carried out according to the following steps. Mouse/human Myl9 peptide-BSA was coated onto the wells of a 96-well plate (Num). After an overnight incubation at 4° C., the wells were blocked at room temperature for one hour with 1× Block Ace (DS Pharma Biomedical Co., Ltd.). After washing three times with 0.02% Tween 20/PBS, the culture supernatant of said fused cells was added to the wells. After incubation at room temperature for one hour and washing three times, horseradish peroxidase-labeled anti-mouse IgG antibody (Jackson ImmunoResearch Laboratories) was added, and this was incubated at room temperature for one hour. After washing 5 times, TMBZ (3,3',5,5'-tetramethylbenzidine) solution was added to the wells, and this was incubated for 5-20 minutes at room temperature. An equal amount of reaction quenching solution (2N $H_2SO_4$) was added to the wells, and absorbance at 450 nm was read with a microplate reader (PerkinElmer).

Evaluation of inhibitory activity against binding between mouse CD69 extracellular region protein and mouse Myl9 was carried out according to the following steps. GST-His-mouse Myl9 was coated onto the wells of a 96-well plate (Nunc). After an overnight incubation at 4° C., the wells were blocked at room temperature for one hour with 1× Block Ace (DS Pharma Biomedical Co., Ltd.). After washing three times with 0.02% Tween 20/PBS, the culture supernatant of said fused cells was added to the wells. This was incubated at room temperature for one hour. 3× Flag-mouse CD69 EC subjected to sugar chain cleaving treatment was added to the wells. After incubation at room temperature for one hour and washing three times, horseradish peroxidase-labeled anti-Flag antibody (SIGMA) was added, and this was incubated at room temperature for one hour. After washing 5 times, TMBZ (3,3',5,5'-tetramethylbenzidine) solution was added to the wells, and this was incubated for 5-20 minutes at room temperature. An equal amount of reaction quenching solution (2N $H_2SO_4$) was added to the wells, and absorbance at 450 nm was read with a microplate reader (PerkinElmer).

Hybridomas were cloned from wells picked up via the above steps by limiting dilution method to ultimately obtain a hybridoma clone that expresses mouse anti-mouse/human Myl9 antibody which has reaction activity against mouse/human Myl9 peptide as well as inhibitory activity against binding between mouse CD69 extracellular region protein and mouse Myl9.

The hybridoma clone obtained was cultured, and anti-mouse/human Myl9 antibody ("Antibody A" (sometimes described as "mAb A")) was purified from the culture supernatant with Protein A (GE Healthcare). Antibody A isotype was determined with monoclonal antibody Isotyping Kit (Serotec) to be IgG2c, κ.

Analysis of Binding Ability of Antibody A Against Mouse/Human Myl9 Protein

The binding ability of Antibody A against mouse and human Myl9 was evaluated by ELISA. Following the steps below, proteins having a histidine tag bound to the C-terminal of each of mouse Myl3 (Genbank Accession No. NP_034989.1, SEQ ID NO. 5), mouse Myl9, human Myl3 (Genbank Accession No. NP_000249.1, SEQ ID NO. 6), and human Myl9 (hereinbelow respectively referred to as mouse Myl3-His, mouse Myl9-His, human Myl3-His, and human Myl9-His) were produced. The comparison of amino acid sequences between mouse Myl3 and human Myl3 (FIG. 1-1B), mouse Myl3 and mouse Myl9 (FIG. 1-2C), as well as human Myl3 and human Myl9 (FIG. 1-2D) are shown.

Genes encoding mouse Myl3 and mouse Myl9 proteins were endowed from Chiba University. Genes encoding human Myl3 and human Myl9 proteins were amplified from human heart cDNA by PCR. These genes were inserted into the BglII/BamHI site of a pET42b vector (Merck) having the gene encoding the cleaving sequence of PreScission Protease (GE Healthcare) inserted therein. The vector produced was transformed into *E. coli* strain BL21-Gold (DE3) pLys (Agilent Technologies) to allow expression of mouse Myl3-His, mouse Myl9-His, human Myl3-His, and human Myl9-His with a GST tag attached. The expressed proteins were purified by Glutathione Sepharose 4 Fast Flow (GE Healthcare), the GST tag was cleaved with PreScission Protease, and mouse Myl3 His, mouse Myl9-His, human Myl3-His, and human Myl9-His were purified by TALON Superflow Metal Affinity Resin (CLONTECH).

The binding ability against mouse/human Myl9 was evaluated following the steps below by ELISA. Mouse Myl3-His, mouse Myl9-His, human Myl3-His, and human Myl9-His were coated onto the wells of a 96-well plate (Nunc). After an overnight incubation at 4° C., the wells were blocked at room temperature for one hour with 1× Block Ace (DS Pharma Biomedical Co., Ltd.). After washing three times with 0.02% Tween 20/PBS, ten serial dilutions by four folds of Antibody A were made from a concentration of 10 μg/mL and added to the wells. After incubation at room temperature for one hour and washing three times, horseradish peroxidase-labeled anti-mouse IgG antibody (Jackson ImmunoResearch Laboratories) was added, and this was incubated at mom temperature for one hour. After washing 5 times, TMBZ (3,3',5,5'-tetramethylbenzidine) solution was added to the wells, and this was incubated for 5-20 minutes at room temperature. An equal amount of reaction quenching solution (2N $H_2SO_4$) was added to the wells, and absorbance at 450 nm was read with a microplate reader (PerkinElmer).

Figure 2:
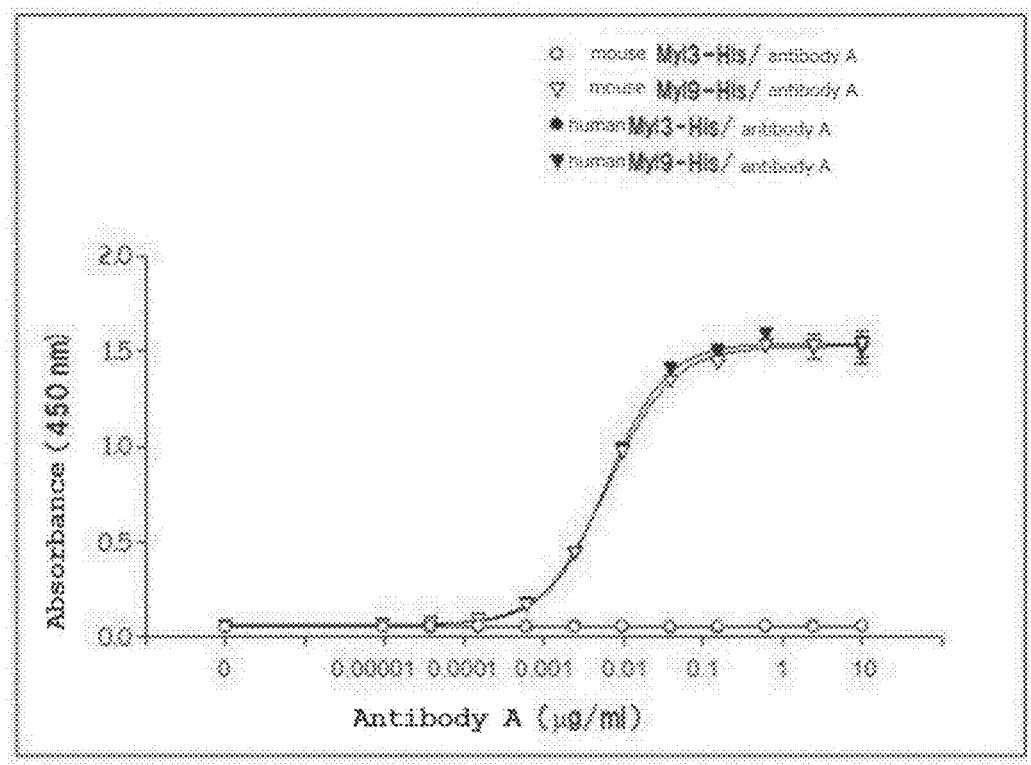
FIG. 2 is the result showing the binding ability of anti-mouse/human Myl9 monoclonal antibody (Antibody A) to mouse Myl9 and human Myl9 as well as to mouse Myl3 and human Myl3.

Antibody A showed concentration-dependent binding to mouse and human. Myl9, but did not bind to mouse and human Myl3 which have low homology with mouse and human Myl9 (FIG. 2).

Evaluation of Inhibitory Activity of Antibody A Against Binding Between Mouse CD69 Extracellular Region Protein and Mouse Myl9

Evaluation of inhibitory activity of Antibody A against binding between mouse CD69 extracellular region protein and mouse Myl9 was performed by competitive ELISA. First, mouse CD69 extracellular region protein and mouse Myl9 protein were produced.

Specifically, each of mouse Myl3 and Myl9 were cloned from the cDNA of bone marrow and cardiac muscle tissue and inserted into the multicloning site of pET42b vector (Merck). The expression vector produced was transformed into Rosetta Competent Cells (Merck), and clones possessing the expression vector were selected. Each of the pre-cultured clone culture mediums was added to 500 mL of LB solution comprising kanamycin, and this was cultured in a shaker at 37° C. IPTG (Nacalai) at a final concentration of 1 mM was added at OD600=0.4, and induced expression of mouse Myl3 and Myl9 proteins was performed for 3 hours at 37° C. After 3 hours, the cells were collected by centrifugation, lysed with a lysis buffer [Tris-HCl (pH 8.0) and 150 mM NaCl], and then homogenized with a sonicator while cooling on ice. The insoluble fraction was removed by centrifugation, this was passed through a 0.45 μm filter (Corning), and then purified with a column packed with Ni-NTA beads (QIAGEN). The beads were washed with a wash buffer [Tris-HCl (pH 8.0), 150 mM NaCl, and 10 mM Imidazole], and then the bound protein was eluted with an elution buffer [Tris-HCl (pH 8.0), 150 mM NaCl, and 500 mM Imidazole]. GST-His-mouse Myl3 and GST-His-mouse Myl9 proteins obtained were subjected to solution displacement to PBS with PD10 (GE Healthcare). Bradford solution (BIO-RAD) was employed for measuring the concentration of the purified protein.

Figure 3A:
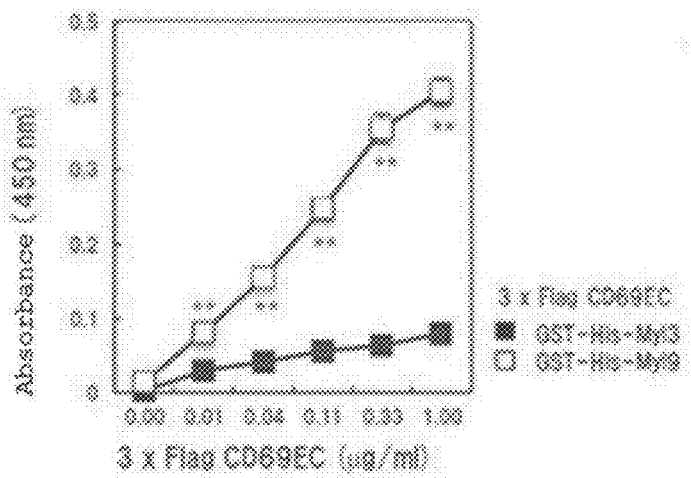
FIGS. 3A-3C show the concentration-dependent binding of mouse CD69 (FIG. 3A) with or (FIG. 3B) without a sugar chain to mouse Myl9, as well as that said binding was significantly inhibited by anti-mouse/human Myl9 monoclonal antibody (Antibody A) (FIG. 3C).
Figure 3B:
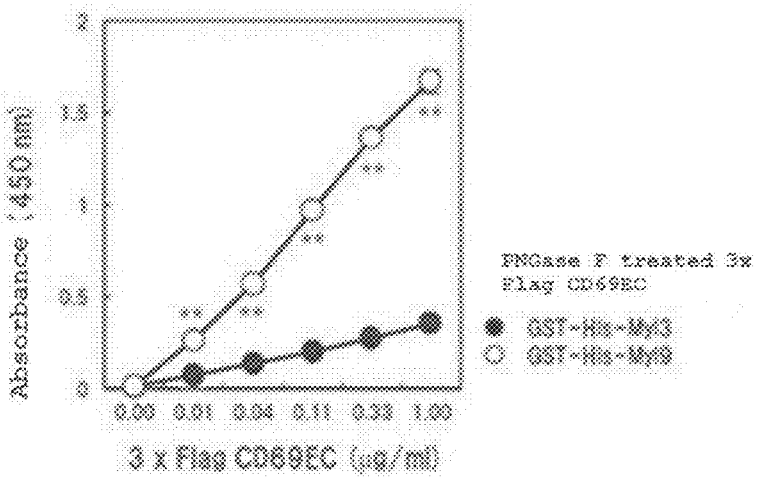

Next, ELISA was performed in order to analyze the presence or absence of association between mouse Myl9 and mouse CD69 (FIGS. 3A and 3B). Specifically, GST-His-mouse Myl3 protein and GST-His-mouse Myl9 protein were added at a concentration of 5 μg/mL, and this was incubated overnight at 4° C. to immobilize them on an ELISA plate. On the next day, Block Ace (Sumitomo Dainippon Pharma Co., Ltd.) was employed to allow blocking at mom temperature for one hour, and then this was washed three times with a wash buffer (50 mM HEPES (pH 6.5), 150 mM NaCl, and 0.02% Tween 20). Different concentration of 3× Flag mouse CD69 EC protein was added to each well, and this was reacted at room temperature for one and a half hours. In FIG. 3B, 3× Flag mouse CD69 EC protein in which the N-linked sugar chain was cleaved with PNGase F (NEB) was employed. The cleaving treatment of the N-linked sugar chain was performed by employing 1,000 U of PNGase F for 4 μg of 3× Flag mouse CD69 EC protein. After washing three times with the wash buffer, HRP-labeled anti-Flag (M2) antibody (Sigma) was added, this was reacted at room temperature for one hour, and then washed five times with the wash buffer. TMB solution (BIO-RAD) was used as the coloring substrate, and the reaction was quenched with 1N $H_2SO_4$. SpectraMAX Paradigm (Molecular Device) was employed to measure the value at 450 nm.

As shown in FIGS. 3A and 3B, concentration-dependent binding of mouse CD69 to mouse Myl9 was significantly detected.

Competitive ELISA was performed in order to evaluate the inhibitory activity of Antibody A against binding between mouse CD69 extracellular region protein and mouse Myl9. Specifically, GST protein (Abcam) and GST-His-mouse Myl9 protein were added to a glutathione-coated plate (Thermo) to immobilize them. Each well was blocked with Block Ace at room temperature for one hour, and then washed three times with the wash buffer (PBS and 0.02% Tween 20). Antibody A and anti-Myl9/12 polyclonal antibody were added at concentrations described in FIG. 3C, and this was reacted at room temperature for one hour. PNGase F-treated 3× Flag mouse CD69 EC protein was added, this was reacted overnight at 4° C., and washed three times with the wash buffer. HRP-labeled anti-Flag (M2) antibody (Sigma) was added, this was reacted at room temperature for one hour, and then washed five times with the wash buffer. TMB solution (BIO-RAD) was used as the coloring substrate, and the reaction was quenched with 1N $H_2SO_4$. SpectraMAX Paradigm (Molecular Device) was employed to measure the value at 450 nm.

Figure 3C:
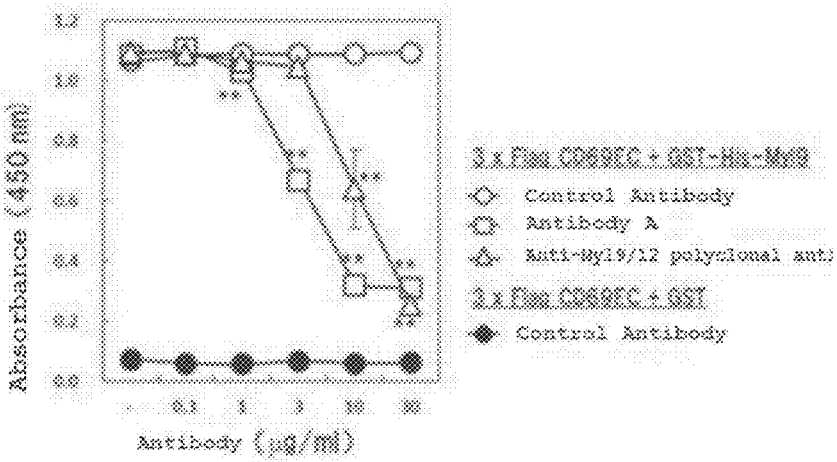
Figure 4A:
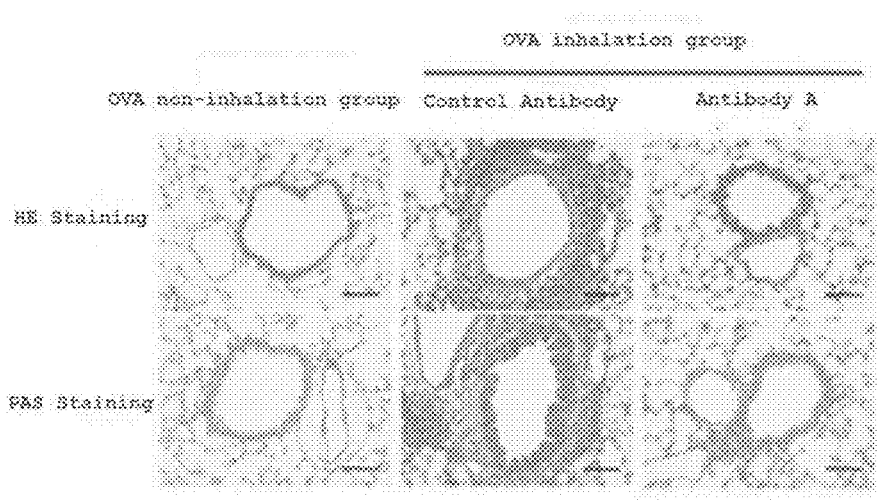
FIGS. 4A-4C show the suppression effect of administration of anti-mouse/human Myl9 monoclonal antibody (Antibody A) on cell infiltration around the bronchial tube that is induced at the time of airway inflammation.
Figure 4B:
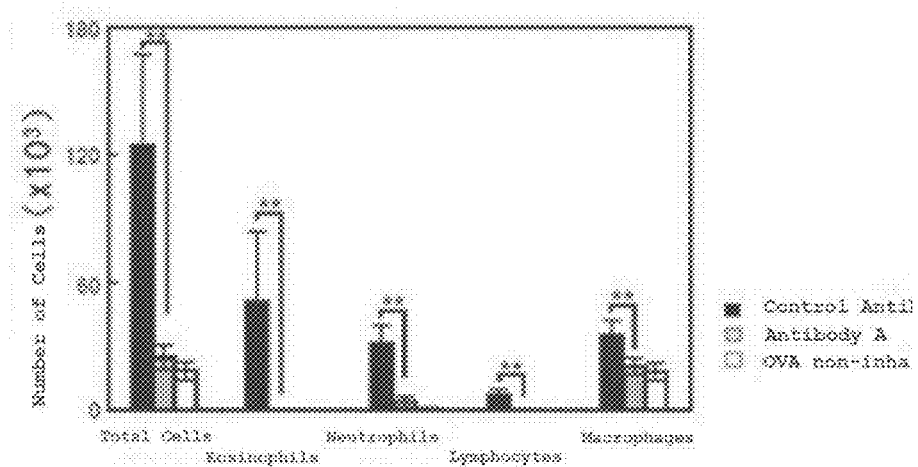
Figure 4C:
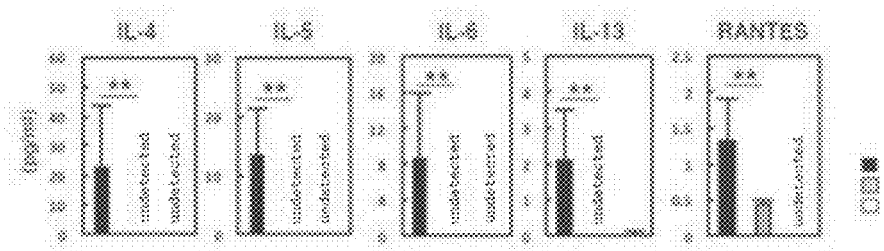
Figure 4D:
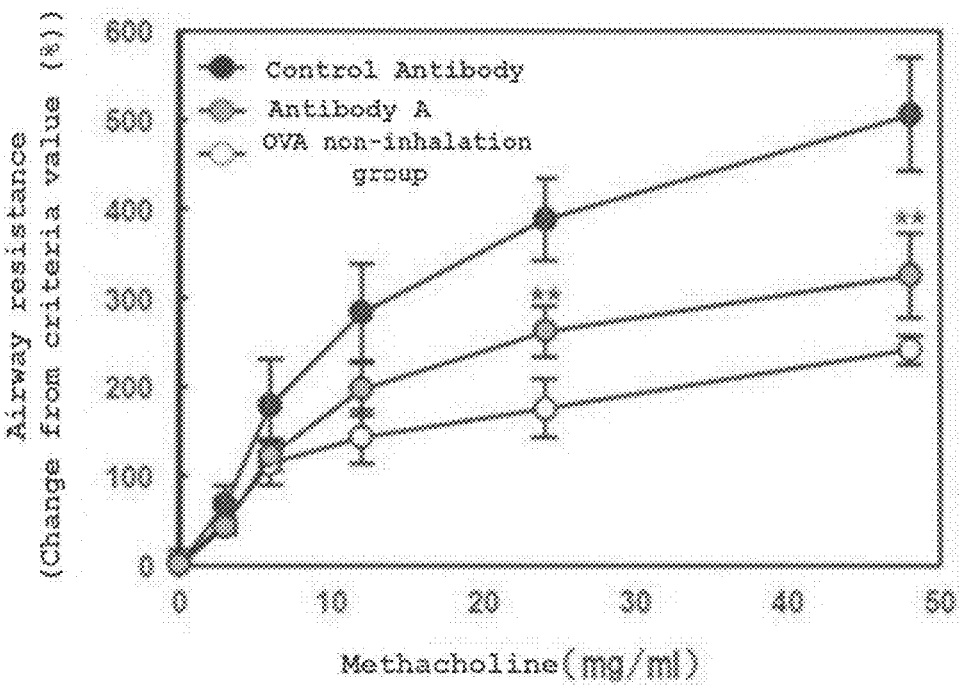
FIGS. 4D-4E show the comparison of methacholine-induced airway resistance on Day 17 after induction of airway inflammation between the Antibody A administration group (FIG. 4D), the anti-Myl9/12 polyclonal antibody administration group (FIG. 4E), and the control antibody administration groups (FIG. 4D, FIG. 4E).
Figure 4E:
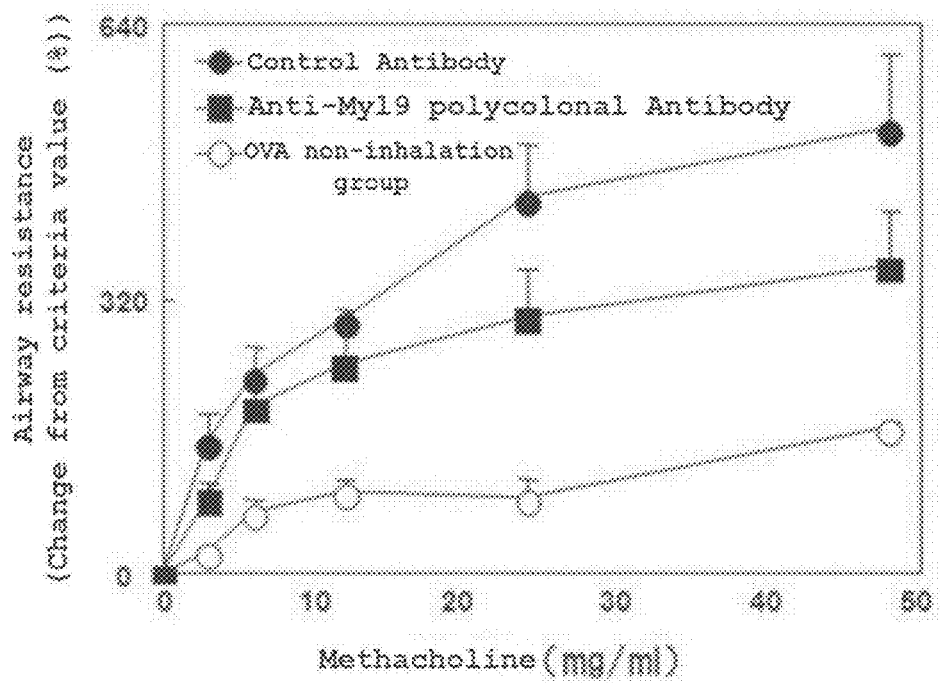

As shown in FIG. 3C, the binding between mouse CD69 and mouse Myl9 was concentration-dependently and significantly inhibited in the presence of Antibody A. This inhibitory activity tended to be higher than that of an anti-Myl9/12 polyclonal antibody.

Sequence Analysis of Antibody A

The DNA sequences encoding the signal sequence of heavy and light chains as well as the variable region of Antibody A were amplified by 5'-RACE (5'-rapid amplification of cDNA ends) method. Total RNA was prepared from said hybridoma with RNeasy Mini Kit (QIAGEN) and treated with DNase (QIAGEN, RNase free DNase set). Double-stranded cDNA was prepared from said total RNA with cDNA Synthesis Kit (TAKARA). The 5' adaptor obtained by annealing of oligoDNA ad29S (ACATCACTC-CGT) (SEQ ID NO. 7) and oligoDNA ad29AS (ACG-GAGTGATGTCCGTCGACGTATCTCTGCGTTGATACT-TCAGCGTAGCT) (SEQ ID NO. 8) was added to said cDNA. The cDNA obtained was amplified by 5' forward primer (5'-PCR4 primer, AGCTACGCTGAAGTAT-CAACGCAGAG) (SEQ ID NO. 9) and 3' reverse primer (GCCAGTGGATAGACTGATGG (SEQ ID NO. 10) was employed for amplifying mouse IgG heavy chain and GATGGATACAGTTGGTGCAGC (SEQ ID NO. 11) was employed for amplifying mouse Igκ light chain). The amplified cDNA was inserted into pCR2.1 vector (Invitrogen/LifeTechnologies). The gene sequence of Antibody A was analyzed with ABI3130XL (SEQ ID NOs. 12-19).

The full length sequences of heavy and light chains of Antibody A were obtained by the following steps. Total RNA was prepared from said hybridoma with RNeasy Mini Kit (QIAGEN) and treated with DNase (QIAGEN, RNase free DNase set). cDNA was prepared from said total RNA with cDNA Synthesis Kit (TAKARA). With the cDNA obtained as the template, gene sequences encoding the heavy and light chains of Antibody A were amplified by PCR with 5' forward primer (GCGAAGCTTGCCGCCAC-CATGGAATGGAGCTGGGTCTTTC (SEQ ID NO. 20) was used for amplifying the heavy chain and GCGAAGCT-TGCCGCCACCATGAAGTTGCCTGTTAGGCTG (SEQ ID NO. 21) was used for amplifying the light chain) and 3' reverse primer (GCGGAATTCATCATTTACCCAGAGAC-CGGGAGATGG (SEQ ID NO. 22) was used for amplifying the heavy chain and (GCGGAATTCACTAACACTCATTC-CTGTTGAAGCTCTTGAC (SEQ ID NO. 23) was used for amplifying the light chain), and each was cloned into pEE6.4 and pEE12.4 vectors (Lonza). The gene sequences were analyzed with ABI3130XL (SEQ ID NOs. 12-19 and 24-27).

For the CDR of Antibody A, the amino acid sequence of Antibody A was numbered according to the Kabat numbering system with Abysis software (licensed from UCL), and based on this numbering, the CDR was determined according to the Kabat definition or AbM definition method for CDR identification (SEQ ID NOs. 28-43).

Example 2: Evaluation of Drug Effect of Antibody A in OVA-Induced Mouse Airway Inflammation Model The effect of in vivo administration of purified mouse anti-mouse/human Myl9 antibody (Antibody A) on allergic airway inflammation was verified with an OVA-induced airway inflammation model.

First, the suppressive effect by administration of Antibody A against cell infiltration around the bronchial tube that is induced at the time of airway inflammation was investigated. Specifically, to wildtype BALB/c mice, 100 μg/mouse (SIGMA) of ovalbumin (OVA) was intraperitoneally administered with 4 mg/mouse of Alum (Thermo) for immunization. The day of first administration was set as Day 0, and the second administration was performed on Day 7. Airway inflammation was induced by subjecting the mice to nebulized inhalation of 1% OVA solution (10 mg/mL saline) for 30 minutes with an ultrasonic wave nebulizer (Omron) on Days 14 and 16 (OVA inhalation). A group without inhalation of OVA was prepared as the control group (No inhalation). Antibody A, or mouse IgG2a, κ antibody (BioLegend) for the control were intraperitoneally administered at 100 μg each on Days 13 and 15. On Day 18, mouse lung was resected, fixed with 10% formalin solution and then embedded in paraffin to produce tissue sections, and hematoxylin/eosin staining (H & E staining) and PAS (Periodic Acid-Schiff) staining were performed (FIG. 4-1A).

As shown in FIG. 4-1A, severe cell infiltration was seen around the bronchial tube in the control antibody administration group that inhaled OVA, but cell infiltration was significantly suppressed in the Antibody A administration group that inhaled OVA (FIG. 4-1A top). Moreover, production of mucus that stained positive for PAS was seen inside the bronchial tube in the control antibody administration group that inhaled OVA, but the production of mucus was also significantly suppressed in the Antibody A administration group that inhaled OVA (FIG. 4-1A bottom).

Subsequently, bronchoalveolar lavage was performed on Day 17 after induction of airway inflammation, and the number of infiltrating cells and infiltrating cell types seen in the bronchoalveolar lavage fluid (BALF) were compared between the Antibody A administration group and the control antibody administration group. Bronchoalveolar lavage was performed by intraperitoneally administering pentobarbital Na (70-90 mg/kg) to mice for anesthesia, and then incising the airway to insert a cannula (Becton Dickinson), and injecting saline (Otsuka Pharmaceutical) to the lung to collect the cells. The number of cells was counted for the collected cells (all cells). Moreover, these cells were suspended in fetal calf serum (FCS), and pasted on a slide glass with Cytospin 3 (Thermo Fisher Scientific). May-Gruenwald Giemsa (MERCK) reagent was employed for staining, and the cells were identified into eosinophils, neutrophils, lymphocytes, and macrophages according to morphological criteria.

As shown in FIG. 4-1B, the total number of infiltrating cells were significantly decreased, and the number of various cells of eosinophils, neutrophils, lymphocytes, and macrophages was also significantly decreased in the Antibody A administration group compared to the control antibody administration group.

Subsequently, various cytokines (IL-4, IL-5, IL-6, IL-13, and RANTES) contained in the collected bronchoalveolar lavage fluid were compared between the Antibody A administration group and the control antibody administration group. Cytometric Bead Array (BD Biosciences) was used for measurement.

Figure 1D:
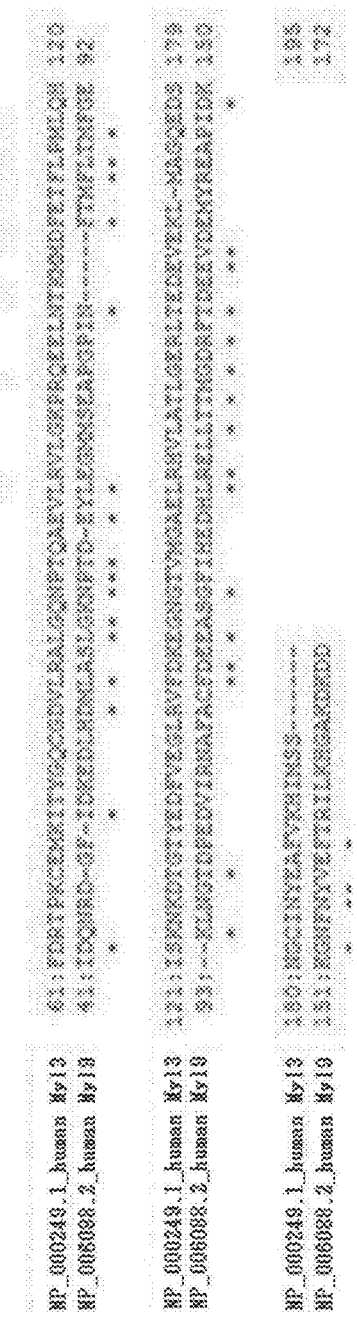

As shown in FIG. 4-1C, production of any of the cytokines (IL-4, IL-5, IL-6, IL-13, and RANTES) was reduced in the Antibody A administration group compared to the control antibody administration group.

Subsequently, methacholine-induced airway resistance on Day 17 after induction of airway inflammation was compared between the Antibody A administration group (FIG. 4-2D), the anti-Myl9/12 polyclonal antibody administration group (FIG. 4-2E), and the control antibody administration groups.

As shown in FIG. 4-2D, airway resistance was methacholine concentration-dependently elevated in the control antibody administration group, whereas the elevation was significantly suppressed in the Antibody A administration group. Moreover, as shown in FIG. 4-2E, in the anti-Myl9/12 polyclonal antibody administration group, although suppression of methacholine concentration-dependent elevation of airway resistance is seen, no significant difference was observed in the effect thereof. It was suggested that Antibody A has a more potent anti-airway inflammation effect than anti-Myl9/12 polyclonal antibody.

Example 3: Evaluation of Drug Effect of Antibody A in Mouse Colitis Model

Powrie et al., Int. Immunol., 5, 1461-1471, 1993 was referred for the production of CD4-positive CD45RB-strong positive (CD4+CD45RB$^{high}$) T lymphocyte transfer inflammatory bowel disease model. The spleen of female 8-10 weeks-old Balb/c mice (Charles River Laboratories Japan, Inc.) was resected, and ground with ground glass to separate the spleen cells. To the separated spleen cells a 5 mL of distilled water containing 155 mM ammonium chloride, 10 mM carbonic acid hydrogen potassium, and 80 μM EDTA-4Na was added per spleen, and this was left at room temperature for 5 minutes to lyse the erythrocytes. Twice the volume of PBS was added to the spleen cell solution, and this was centrifuged at 1500 rpm for 5 minutes, and the precipitate was collected. CD4 T lymphocytes were purified from the separated spleen cells by CD4 T cell isolation Kit (from Miltenyi). In order to separate CD4-positive CD45RB-strong positive T lymphocytes, the purified CD4 T lymphocytes were subjected to double staining with phycoerythrin (PE)-labeled anti-CD4 antibody (from eBioscience) and fluorescein isothiocyanate (FITC)-labeled anti- CD45RB antibody (from eBioscience). After double staining, CD4-positive CD45RB-strong positive cells were sorted with FACSAria (from Becton, Dickinson and Company) to collect the cells of interest. After washing the collected cells with PBS, they were suspended in PBS to a cell concentration of $2 \times 10^6$ cells/mL. To the peritoneal cavity of female 8 weeks-old SCID mice (CLEA Japan, Inc.), 250 μL each, i.e. $5 \times 10^5$ cells/mouse of CD4-positive CD45RB-strong positive cells prepared as above was transferred. To eight animals per group of SCID mice having CD4-positive CD45RB-strong positive cells transferred, 500 μg of the control antibody (mouse IgG) and 500 μg of Antibody A (antibody in PBS solution) were administered twice per week starting from Day 11 after cell transfer. Note that administration was from the tail vein. Moreover, as the negative control group, mouse CD4 T lymphocytes that were purified with CD4 T cell Isolation Kit (from Miltenyi) but not separated for CD45RB expression strength (whole CD4-positive cells) were transferred at $5 \times 10^5$ cells/mouse. Autopsy was performed 27 days after cell transfer to score and evaluate weight loss and nature of stool in the large intestine. The scoring for nature of stool employed in dextran sodium sulfate-induced colitis (Cooper et al., Lab. Invest., 69, 238-249, 1993) was used for scoring for the nature of stool.

Figure 5:
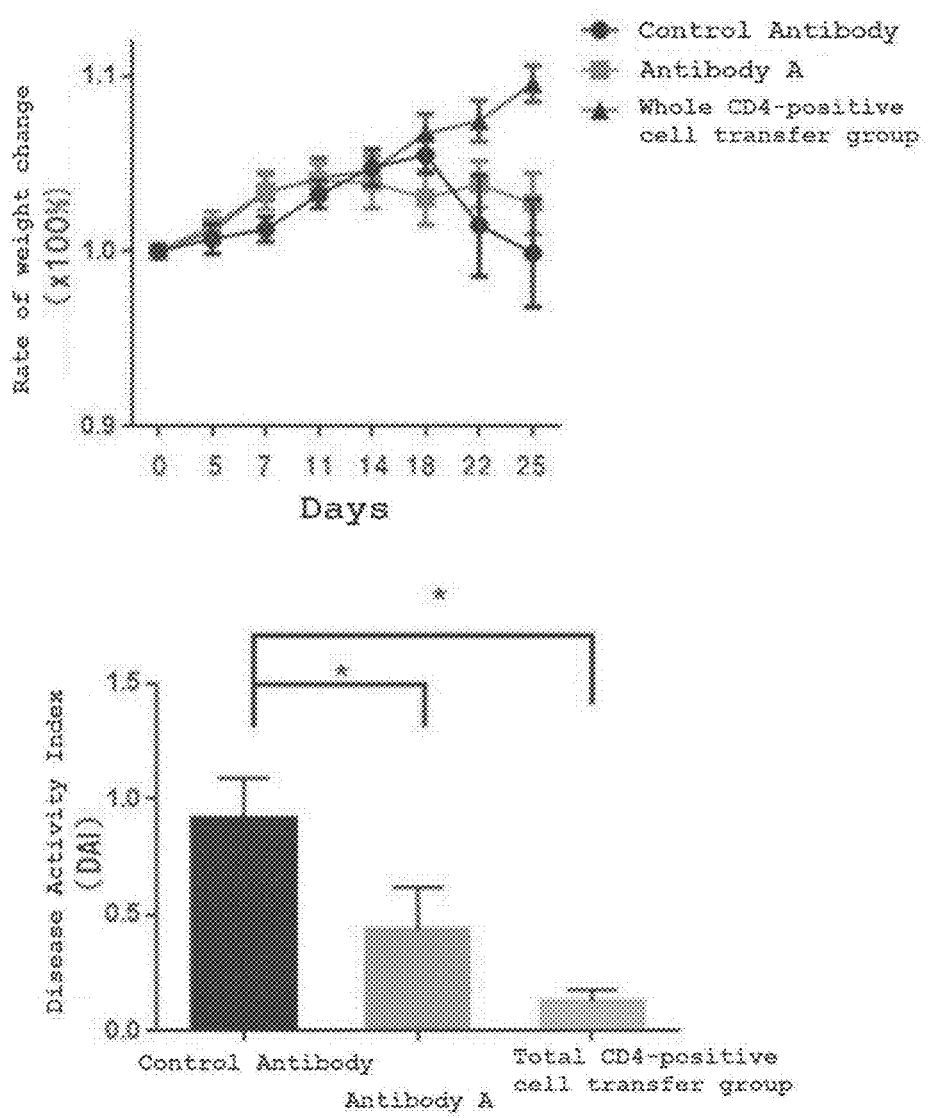
FIG. 5 shows the results of weight loss (top figure) and disease activity index (DAI) (bottom figure) due to anti-mouse/human Myl9 monoclonal antibody (Antibody A) in a CD4-positive CD45RB-strong positive (CD4+CD45RB$^{high}$) T lymphocyte transfer inflammatory bowel disease model.

There was significant reduction in disease activity index (DAI) in the Antibody A administration group compared to the control antibody administration group (FIG. 5).

Example 4: Production of Chimeric and Humanized Antibodies from Antibody A

Preparation of Chimeric Antibody and Humanized Antibody

First, an expression vector for a chimeric antibody was constructed. As the heavy chain, the gene sequence encoding the signal sequence of the heavy chain of Antibody A (SEQ ID NO. 16) and the gene sequence encoding the variable region (SEQ ID NO. 17) were inserted into an expression vector (pcDNA3.4) comprising the gene sequence (SEQ ID NO. 45) encoding the constant region of human IgG2 having mutations V234A and G237A and the C-terminal lysine residue deletion (SEQ ID NO. 44), and as the light chain, the gene sequence encoding the signal sequence of the light chain of Antibody A (SEQ ID NO. 18) and the gene sequence encoding the variable region (SEQ ID NO. 19) were inserted into an expression vector (pcDNA3.4) comprising the gene sequence (SEQ ID NO. 47) encoding the constant region of human Igκ (SEQ ID NO. 46), thereby constructing an expression vector for a chimeric antibody. In order to produce the chimeric antibody, using Expi293 expression system (Gibco/ThermoFisher), said expression vector was transfected into an Expi293F cell (Gibco/ThermoFisher). The supernatant was collected and purified with Protein A (GE Healthcare). Here, "V234A" represents a mutation where valine at position 234 is substituted to alanine and "G237A" represents a mutation where glycine at position 237 is substituted to alanine.

Subsequently, the variable region of the humanized antibody was designed. Based on the high homology to the framework region (FR) of Antibody A, the FR of a human antibody, IGKV2-28*01 (SEQ ID NO. 48) or IGKV2-24*01 (SEQ ID NO. 49) and JK4 (SEQ ID NO. 50) for the light chain, and IGHV1-69*02 (SEQ ID NO. 51), IGHV1-46*01 (SEQ ID NO. 52), or IGHV7-4-1*02 (SEQ ID NO. 53) and JH4 (SEQ ID NO. 54) for the heavy chain were selected as the FR of the humanized antibody. Then, a 3D structure prediction model of mouse Antibody A was employed to predict the amino acid in the FR that interacts with the amino acid of CDR, and grafted together with CDRs (SEQ ID NOs. 28-35). The constant region of human IgG2 possessing mutations V234A and G237A and having the C-terminal lysine residue deletion (SEQ ID NO. 44), and the constant region of human Igκ (SEQ ID NO. 46) were each employed as the constant regions of heavy and light chains. HK1-4 (SEQ ID NO. 55), HK1-5 (SEQ ID NO. 56), HK1-6 (SEQ ID NO. 57), HK1-A (SEQ ID NO. 58), HK2-5 (SEQ ID NO. 59), HK2-6 (SEQ ID NO. 60), HK2-9 (SEQ ID NO. 61), and HK3-2 (SEQ ID NO. 62) were designed as heavy chain variable regions of the humanized antibody to which CDR determined by the Kabat definition method (SEQ ID NOs. 28, 30, and 32) were grafted, HA1-4 (SEQ ID NO. 63) and HA1-6 (SEQ ID NO. 64) were designed as heavy chain variable regions of the humanized antibody to which CDR determined by the AbM definition method (SEQ ID NOs. 29, 31, 32) were grafted, HK1-4, HK1-5, HK1-6, HK1-A, HA1-4, and HA1-6 were designed as heavy chain variable regions of the humanized antibody that employ IGHV1-69*02 and JH4, HK2-5, HK2-6, and HK2-9 were designed as heavy chain variable regions of the humanized antibody that employ IGHV1-46*01 and JH4, HK3-2 was designed as the heavy chain variable regions of the humanized antibody that employs IGHV7-4-1*02 and JH4, L1-4 (SEQ ID NO. 65), L1-5 (SEQ ID NO. 66), and L1-A (SEQ ID NO. 67) were designed as light chain variable regions of the humanized antibody that employ IGKV2-28*01 and JK4, and L4-2 (SEQ ID NO. 68) was designed as light chain variable regions of the humanized antibody that employs IGKV2-24*01 and JK4.

The gene sequences encoding the amino acid sequences of HK1-4, HK1-5, and HK1-6 were produced by designing an amino acid sequence in which the heavy chain CDRs of Antibody A (SEQ ID NOs. 28, 30, and 32) were grafted into IGHV1-69*02 (SEQ ID NO. 51) and JH4 (SEQ ID NO. 54) and the signal sequence (SEQ ID NO. 69) was added at the N-terminal, converting the designed amino acid sequence into a gene sequence and synthesizing the gene sequence by GenScript USA Inc., and introducing mutations by PCR (HK1-4: SEQ ID NO. 70, HK1-5: SEQ ID NO. 71, HK1-6: SEQ ID NO. 72, signal sequence: SEQ ID NO. 73). The gene sequence encoding the amino acid sequence of HK1-A was converted from an amino acid sequence having the signal sequence (SEQ ID NO. 69) added at the N-terminal of HK1-A and synthesized by GenScript USA Inc. (HK1-A: SEQ ID NO. 74, signal sequence: SEQ ID NO. 75). The gene sequences encoding the amino acid sequences of HK2-5, HK2-6, and HK2-9 were produced by designing an amino acid sequence in which the heavy chain CDRs of Antibody A (SEQ ID NOs. 28, 30, and 32) were grafted into IGHV1-46*01 (SEQ ID NO. 52) and JH4 (SEQ ID NO. 54) and the signal sequence (SEQ ID NO. 69) was added at the N-terminal, converting the designed amino acid sequence into a gene sequence and synthesizing the gene sequence by GenScript USA Inc., and introducing mutations by PCR (HK2-5: SEQ ID NO. 76, HK2-6: SEQ ID NO. 77, HK2-9: SEQ ID NO. 78, signal sequence: SEQ ID NO. 79). The gene sequence encoding the amino acid sequence of HK3-2 was synthesized by converting an amino acid sequence having the signal sequence (SEQ ID NO. 69) added at the N-terminal of HK3-2 into a gene sequence by GenScript USA Inc. (HK3-2: SEQ ID NO. 80, signal sequence: SEQ ID NO. 81). The gene sequences encoding the amino acid sequences of HA1-4 and HA1-6 were produced by designing an amino acid sequence in which the heavy chain CDRs of Antibody A (SEQ ID NOs. 29, 31, and 32) into IGHV1-

69*02 (SEQ ID NO. 51) and JH4 (SEQ ID NO. 54) and the signal sequence (SEQ ID NO. 69) was added at the N-terminal, converting into a gene sequence and synthesizing the gene sequence by GenScript USA Inc., and introducing mutations by PCR (HA1-4: SEQ ID NO. 82, HA1-6: SEQ ID NO. 83, signal sequence: SEQ ID NO. 84). The gene sequences encoding the amino acid sequences of L1-4 and L1-5 were produced by designing an amino acid sequence in which the light chain CDRs of Antibody A (SEQ ID NOs. 33-35) into IGKV2-28*01 (SEQ ID NO. 48) and JK4 (SEQ ID NO. 50) and the signal sequence (SEQ ID NO. 85) was added at the N-terminal, converting into a gene sequence and synthesizing the gene sequence by GenScript USA Inc., and introducing mutations by PCR (L1-4: SEQ ID NO. 86, L1-5: SEQ ID NO. 87, signal sequence: SEQ ID NO. 88). The gene sequences encoding the amino acid sequences of L1-A and L4-2 were synthesized by converting amino acid sequences having the signal sequence (SEQ ID NO. 85) added at the N-terminal of L1-A and L4-2 into gene sequences by GenScript USA Inc. (L1-A: SEQ ID NO. 89, signal sequence of L1-A: SEQ ID NO. 90, L4-2: SEQ ID NO. 91, signal sequence of L4-2: SEQ ID NO. 92). The genes encoding these humanized heavy chain variable regions and signal sequences were inserted into an expression vector (pcDNA3.4) comprising a gene sequence (SEQ ID NO. 45) encoding the constant region of human IgG2 possessing mutations V234A and G237A and having the C-terminal lysine residue deletion (SEQ ID NO. 44). The genes encoding these humanized light chain variable regions and signal sequences were inserted into an expression vector (pcDNA3.4) comprising a gene sequence (SEQ ID NO. 47) encoding the constant region of human Igκ (SEQ ID NO. 46). Here, "V234A" represents a mutation where valine at position 234 is substituted to alanine and "G237A" represents a mutation where glycine at position 237 is substituted to alanine. In order to produce the antibody, using Expi293 expression system (Gibco/ThermoFisher), said expression vector was transfected into Expi293F cells (Gibco/ThermoFisher) in the combinations shown in Table 1. The supernatant was collected and purified with Protein A (GE Healthcare).

TABLE 1

| Humanized antibody No. | H chain Variable region | | | | L chain Variable region | | | |
|---|---|---|---|---|---|---|---|---|
| | Name | Amino acid sequence (SEQ ID NO.) | Nucleic acid sequence (SEQ ID NO.) | | Name | Amino acid sequence (SEQ ID NO.) | Nucleic acid sequence (SEQ ID NO.) | |
| 110 | HA1-6 | 64 | 83 | | L1-5 | 66 | 87 | |
| 111 | HA1-4 | 63 | 82 | | L1-5 | 66 | 87 | |
| 112 | HK1-5 | 56 | 71 | | L1-5 | 66 | 87 | |
| 113 | HK1-6 | 57 | 72 | | L1-5 | 66 | 87 | |
| 114 | HK1-4 | 55 | 70 | | L1-5 | 66 | 87 | |
| 115 | HK1-A | 58 | 74 | | L1-5 | 66 | 87 | |
| 116 | HK2-5 | 59 | 76 | | L1-5 | 66 | 87 | |
| 117 | HK2-6 | 60 | 77 | | L1-5 | 66 | 87 | |
| 118 | HK2-9 | 61 | 78 | | L1-5 | 66 | 87 | |
| 121 | HA1-6 | 64 | 83 | | L4-2 | 68 | 91 | |
| 122 | HA1-4 | 63 | 82 | | L4-2 | 68 | 91 | |
| 123 | HK1-5 | 56 | 71 | | L4-2 | 68 | 91 | |
| 124 | HK1-6 | 57 | 72 | | L4-2 | 68 | 91 | |
| 125 | HK1-4 | 55 | 70 | | L4-2 | 68 | 91 | |
| 126 | HK1-A | 58 | 74 | | L4-2 | 68 | 91 | |
| 127 | HK2-5 | 59 | 76 | | L4-2 | 68 | 91 | |
| 128 | HK2-6 | 60 | 77 | | L4-2 | 68 | 91 | |
| 129 | HK2-9 | 61 | 78 | | L4-2 | 68 | 91 | |
| 131 | HK3-2 | 62 | 80 | | L1-4 | 65 | 86 | |
| 132 | HK3-2 | 62 | 80 | | L1-A | 67 | 89 | |
| 133 | HK3-2 | 62 | 80 | | L1-5 | 66 | 87 | |
| 134 | HK3-2 | 62 | 80 | | L4-2 | 68 | 91 | |

Analysis of Binding Ability of Chimeric and Humanized Antibodies Prepared from Antibody A Against Human Myl9 Protein The binding ability of chimeric and humanized antibodies prepared from Antibody A against human Myl9 was evaluated by ELISA. Human Myl3-His and human Myl9-His proteins were prepared by methods described in Example 1.

The binding ability against human Myl9 was evaluated following the steps below by ELISA. Human Myl3-His and human Myl9-His were coated onto the wells of a 96-well plate (Nunc). After an overnight incubation at 4° C., the wells were blocked at room temperature for one hour with 1× Block Ace (DS Pharma Biomedical Co., Ltd.). After washing three times with 0.02% Tween 20/PBS, seven serial dilutions by six folds of the chimeric and humanized antibodies were made from a concentration of 10 μg/mL and added to the wells. After incubation at room temperature for one hour and washing three times, horseradish peroxidase-labeled anti-human IgG antibody (Jackson ImmunoResearch Laboratories) was added, and this was incubated at room temperature for one hour. After washing 5 times, TMBZ (3,3',5,5'-tetramethylbenzidine) solution was added to the wells, and this was incubated for 5-20 minutes at room temperature. An equal amount of reaction quenching solution (2N $H_2SO_4$) was added to the wells, and absorbance at 450 nm was read with a microplate reader (PerkinElmer).

Figure 6A:
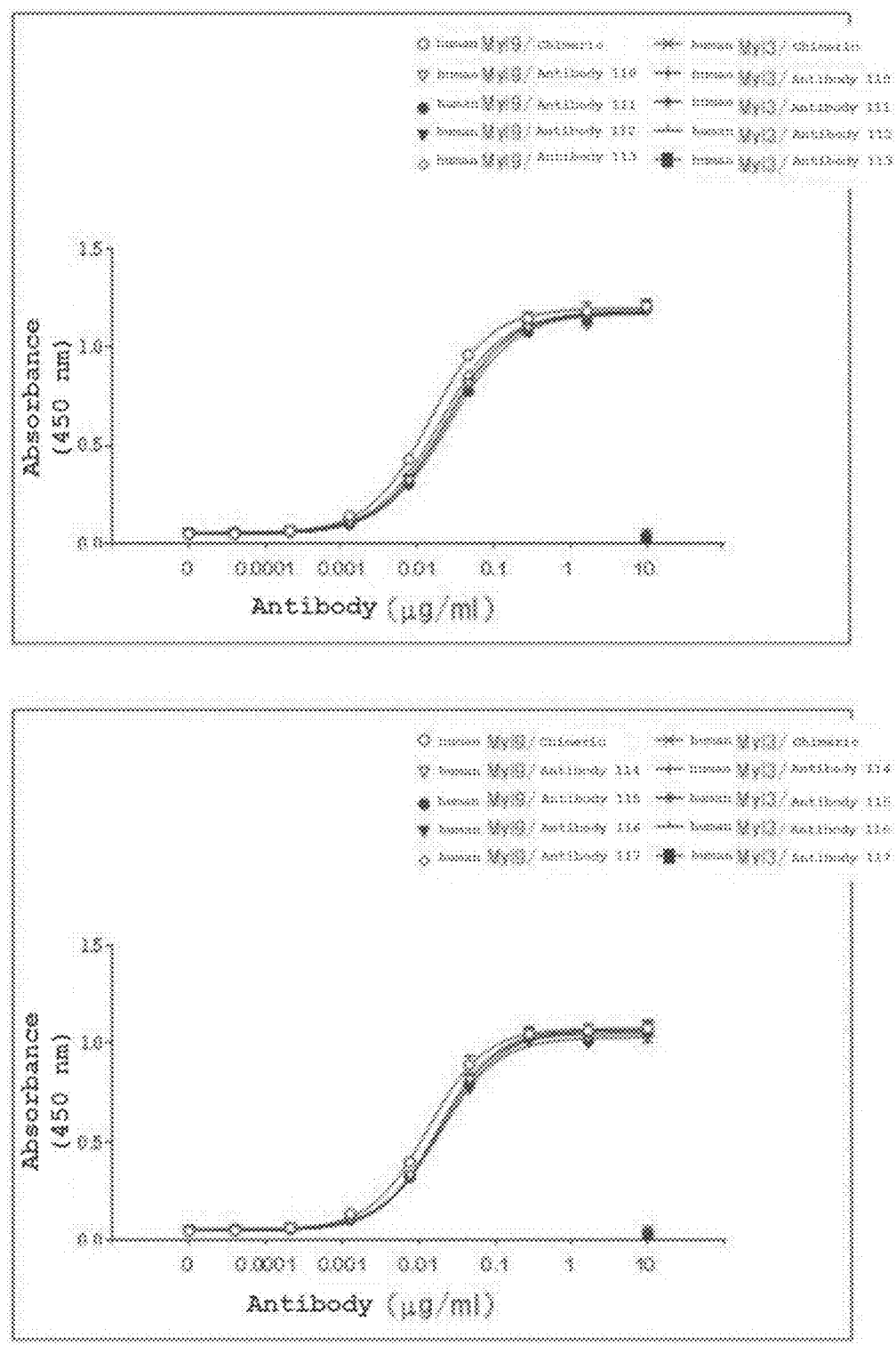
FIG. 6A shows ELISA results evaluating the binding ability of the chimeric and humanized antibodies prepared from Antibody A to human Myl9.
Figure 6B:
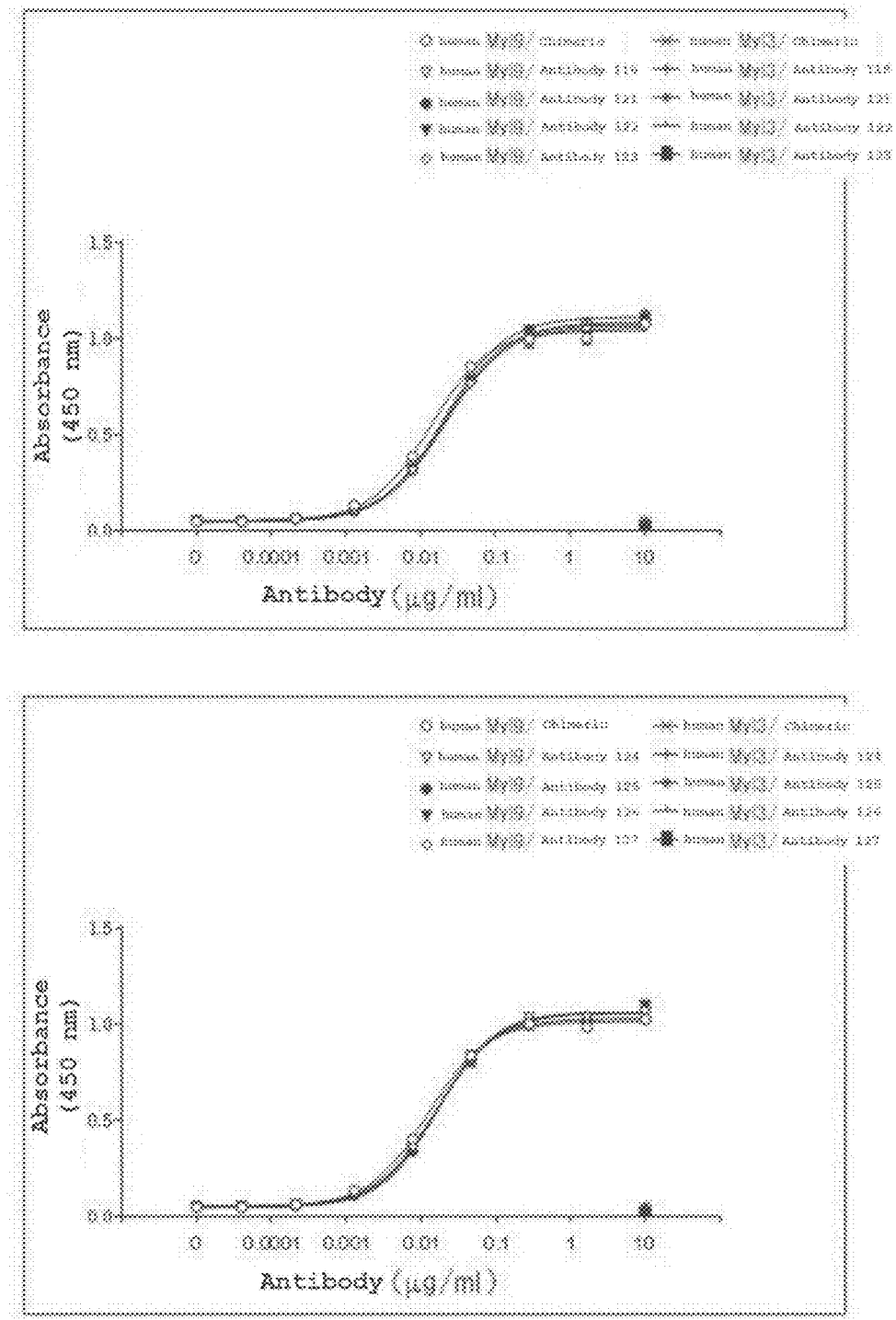
FIG. 6B shows ELISA results evaluating the binding ability of the chimeric and humanized antibodies prepared from Antibody A to human Myl9.
Figure 6C:
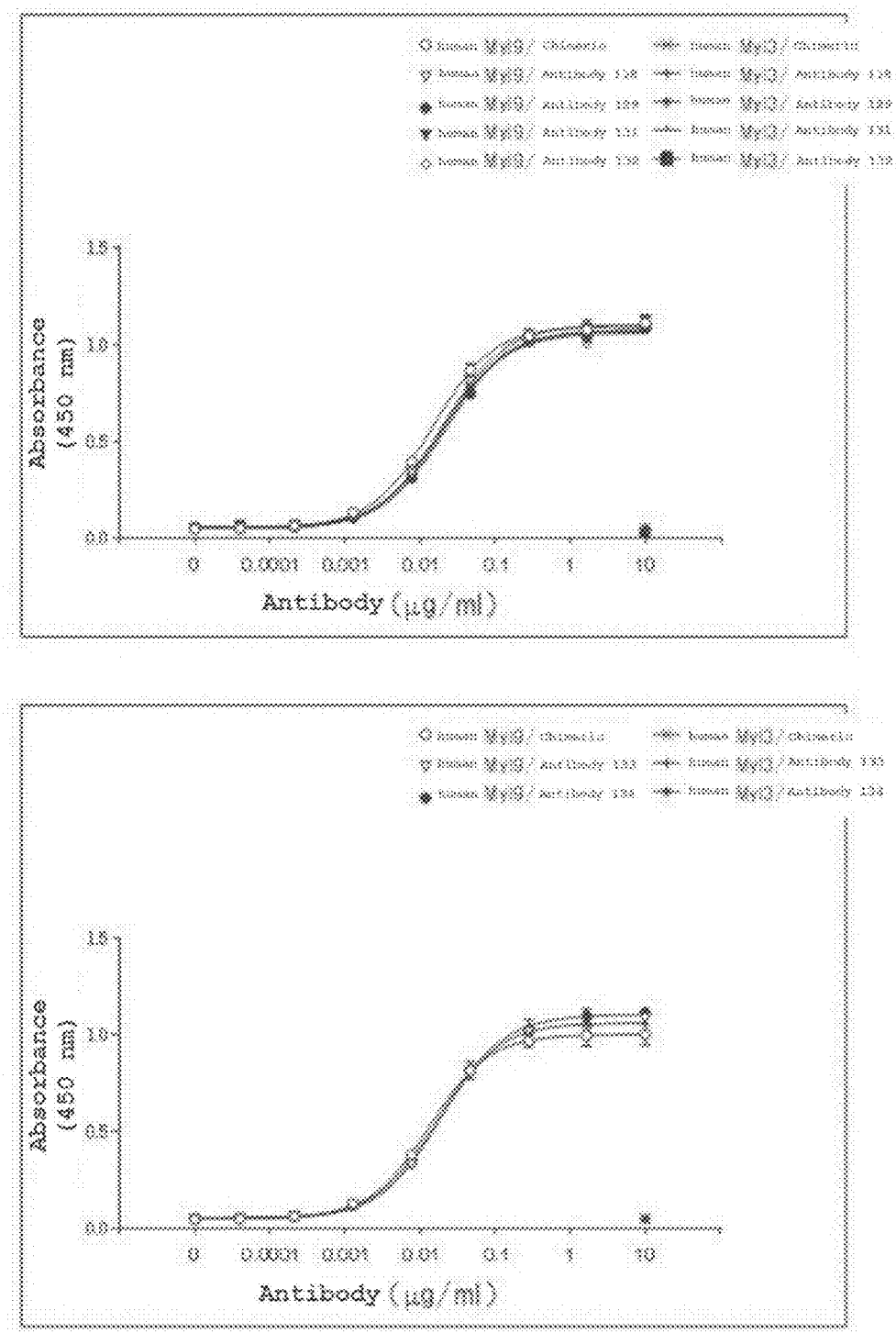
FIG. 6C shows ELISA results evaluating the binding ability of the chimeric and humanized antibodies prepared from Antibody A to human Myl9.

All humanized antibodies in Table 1 bound concentration-dependently to human Myl9 to the same extent as the chimeric antibody, and did not bind to human Myl3 (FIGS. 6-1 to 6-3).

Figures 7A, 7B:
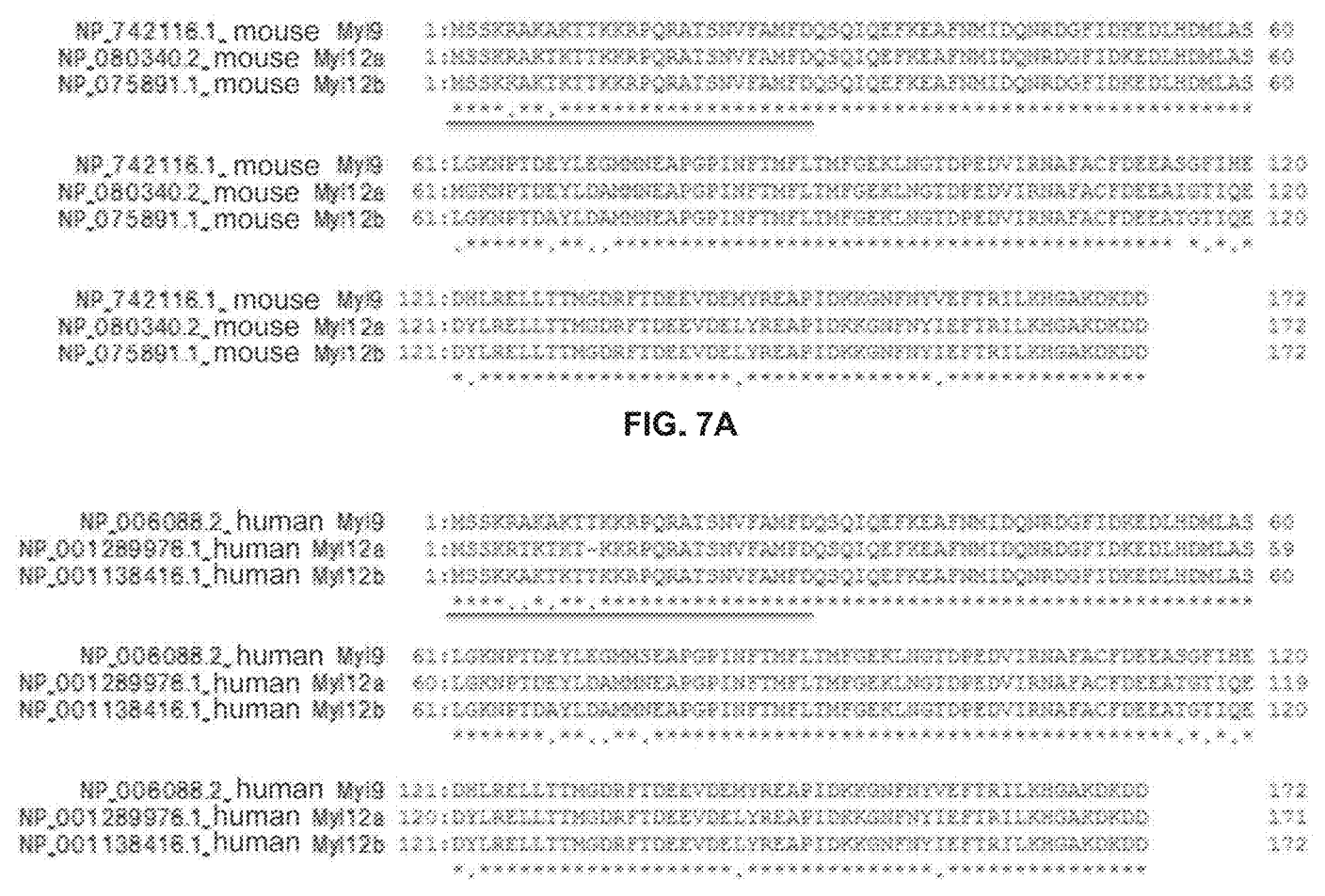

Example 5: Binding Ability of Antibody A and Chimeric and Humanized Antibody Thereof Against Mouse/Human Myl12a and 12b Proteins Preparation of Mouse/Human Myl12a and Myl12b Proteins Following the steps below, proteins having a histidine tag bound to the C-terminal of each of mouse Myl12a (Genbank Accession No. NP_080340.2, SEQ ID NO. 93), mouse Myl12b (Genbank Accession No. NP_075891.1, SEQ ID NO. 94), human Myl12a (Genbank Accession No. NP_001289976.1, SEQ ID NO. 95) and human Myl12b (Genbank Accession No. NP_001138416.1 SEQ ID NO. 96) (hereinbelow respectively referred to as mouse Myl12a-His, mouse Myl12b-His, human Myl12a-His, and human Myl12b-His) were produced. The comparison of amino acid sequences between mouse Myl9, Myl12a and Myl12b (FIG. 7A) as well as human Myl9, Myl12a and Myl12b (FIG. 7B) are shown.

Genes encoding mouse Myl12a and Myl12b proteins were endowed from Chiba University. Genes encoding human Myl12a and Myl12b proteins were amplified from human heart or small intestine cDNA by PCR. These genes were inserted into the BgIII/BamHI site of a pET42b vector (Merck) having the gene encoding the cleaving sequence of PreScission Protease (GE Healthcare) inserted therein. The vector produced was transformed into E. coli strain BL21-Gold (DE3) pLys (Agilent Technologies) to allow expression of mouse Myl12a-His, mouse Myl12b-His, human Myl12a-His, and human Myl12b-His with a GST tag attached. The expressed proteins were purified by Glutathione Sepharose 4 Fast Flow (GE Healthcare), the GST tag was cleaved with PreScission Protease, and mouse Myl12a-His, mouse Myl12b-His, human Myl12a-His, and human Myl12b-His were purified by TALON Superflow Metal Affinity Resin (CLONTECH).

To mouse Myl12a-His, mouse Myl12b-His, human Myl12a-His, human Myl12b-His, or mouse Myl3-His, mouse Myl9-His, human Myl3-His, human Myl9-His purified in Example 1 were added dithiothreitol (Wako) at the final concentration of 50 mM, and the incubation was performed at 4° C. for one hour to obtain monomers. The dialysis was performed with PBS after the incubation.

Analysis of Binding Ability of Antibody A against Mouse/Human Myl12a and Myl12b Proteins The binding ability of Antibody A against mouse/human Myl12a and Myl12b was evaluated following the steps below by ELISA. Mouse Myl3-His, mouse Myl9-His, mouse Myl12a-His, mouse Myl12b-His, human Myl3-His, human Myl9-His, human Myl12a-His, and human Myl12b-His were coated onto the wells of a 96-well plate (Nunc). After an overnight incubation at 4° C., the wells were blocked at room temperature for one hour with 1× Block Ace (DS Pharma Biomedical Co., Ltd.). After washing three times with 0.02% Tween 20/PBS, eleven serial dilutions by four folds of Antibody A were made from a concentration of 10 µg/mL and added to the wells. After incubation at room temperature for one hour and washing three times, horseradish peroxidase-labeled anti-mouse IgG antibody (Jackson ImmunoResearch Laboratories) was added, and this was incubated at room temperature for one hour. After washing 5 times, TMBZ (3,3',5,5'-tetramethylbenzidine) solution was added to the wells, and this was incubated for 5-20 minutes at room temperature. An equal amount of reaction quenching solution (2N $H_2SO_4$) was added to the wells, and absorbance at 450 nm was read with a microplate reader (Thermo Scientific).

Figure 8A:
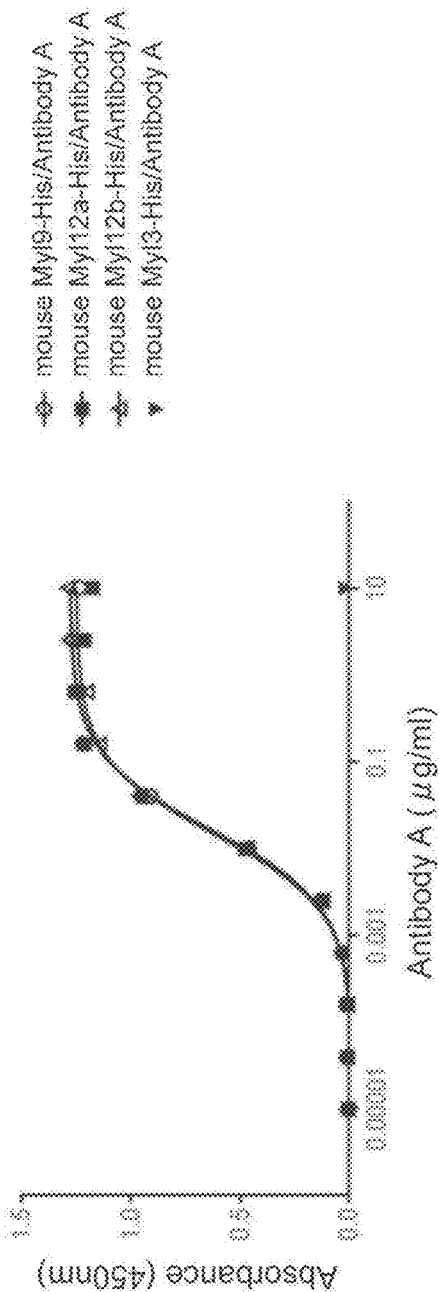
FIGS. 8A-8B show ELISA results evaluating the binding ability of Antibody A to mouse Myl9, mouse Myl12a and mouse Myl12b (FIG. 8A) as well as to human Myl9, human Myl12a and human Myl12b (FIG. 8B).
Figure 8B:
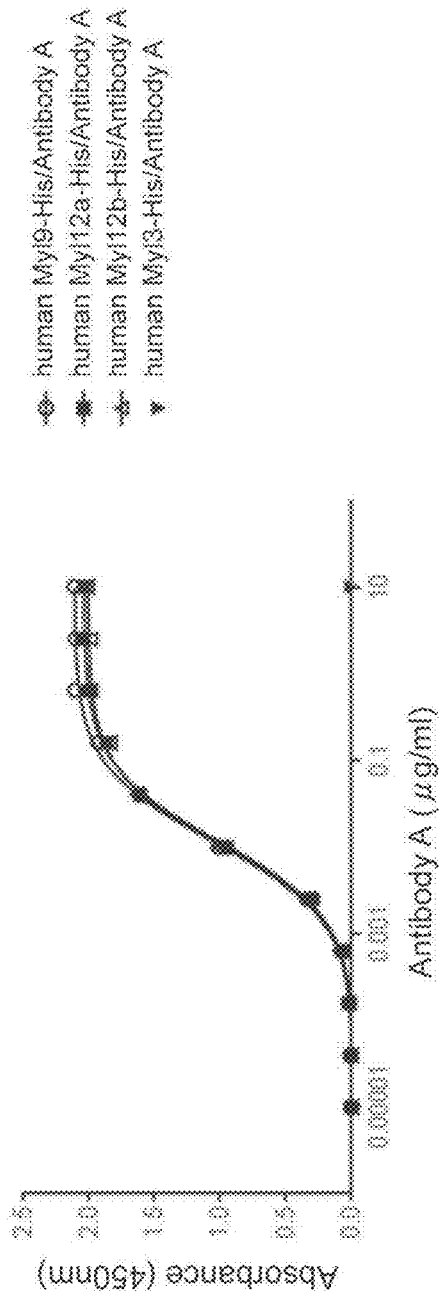

Antibody A showed concentration-dependent binding to Myl12a and Myl12b which have high homology with mouse and human Myl9, but did not bind to mouse and human Myl3 which has low homology with mouse and human Myl9 (FIGS. 8A and B).

Analysis of Binding Ability of Chimeric and Humanized Antibodies Prepared from Antibody A Against Human Myl12a and Myl12b Proteins The binding ability of chimeric and humanized antibodies prepared from Antibody A against human Myl12a and Myl12b was evaluated following the steps below by ELISA. Human Myl3-His, human Myl9-His, human Myl12a-His and human Myl12b-His were coated onto the wells of a 96-well plate (Nunc), respectively. After an overnight incubation at 4° C., the wells were blocked at room temperature for one hour with 1× Block Ace (DS Pharma Biomedical Co., Ltd.). After washing three times with 0.02% Tween 20/PBS, the chimeric and humanized antibodies were diluted at the concentration of 0.01, 0.1 and 1 µg/mL, respectively and added to the wells. After incubation at room temperature for one hour and washing three times, horseradish peroxidase-labeled anti-human IgG antibody (Jackson ImmunoResearch Laboratories) was added, and this was incubated at room temperature for one hour. After washing 5 times, TMBZ (3,3',5,5'-tetramethylbenzidine) solution was added to the wells, and this was incubated for 5-20 minutes at room temperature. An equal amount of reaction quenching solution (2N $H_2SO_4$) was added to the wells, and absorbance at 450 nm was read with a microplate reader (Thermo Scientific).

Figure 9A:
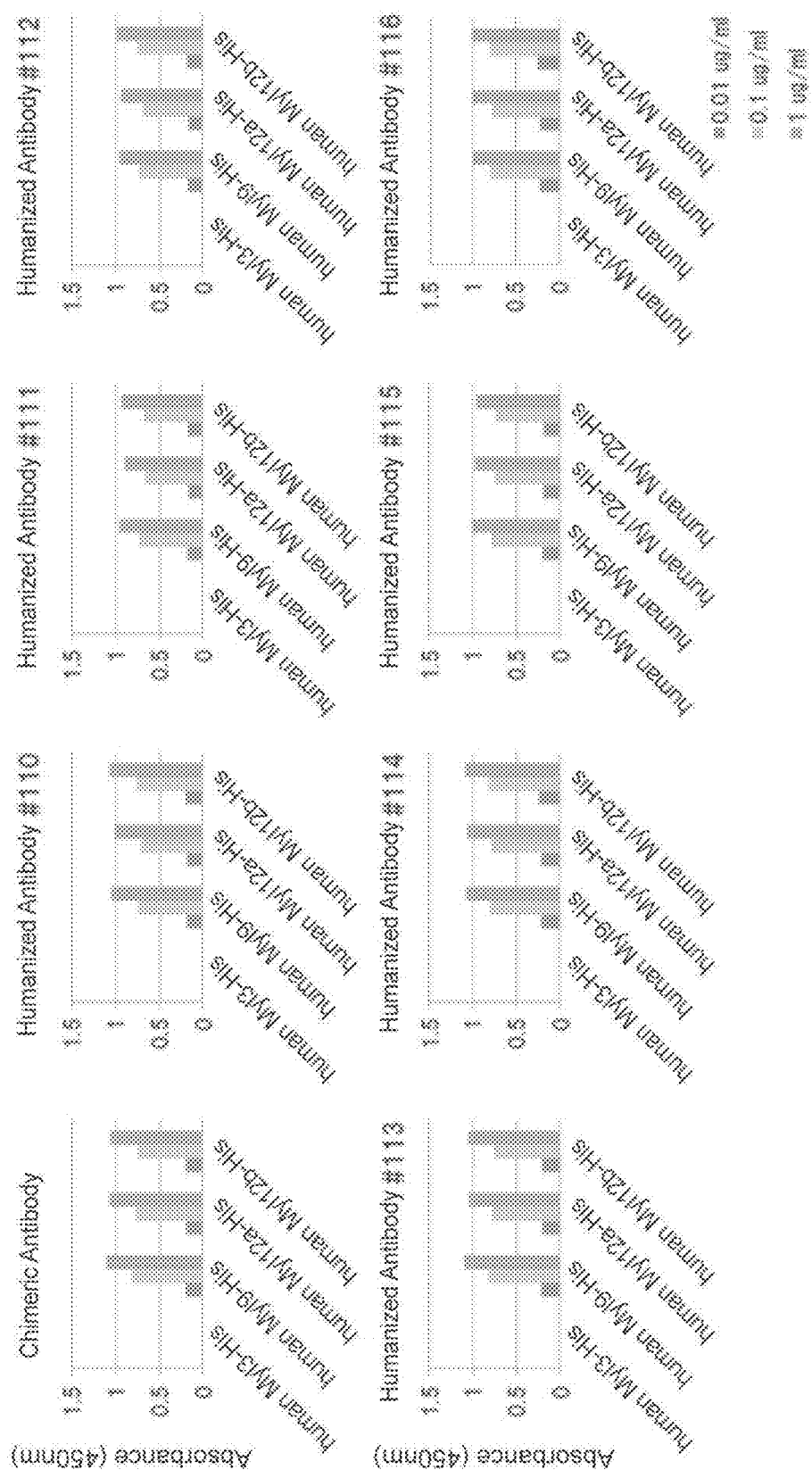
FIG. 9A shows ELISA results evaluating the binding ability of the chimeric and humanized antibodies prepared from Antibody A to human Myl12a and 12b.
Figure 9B:
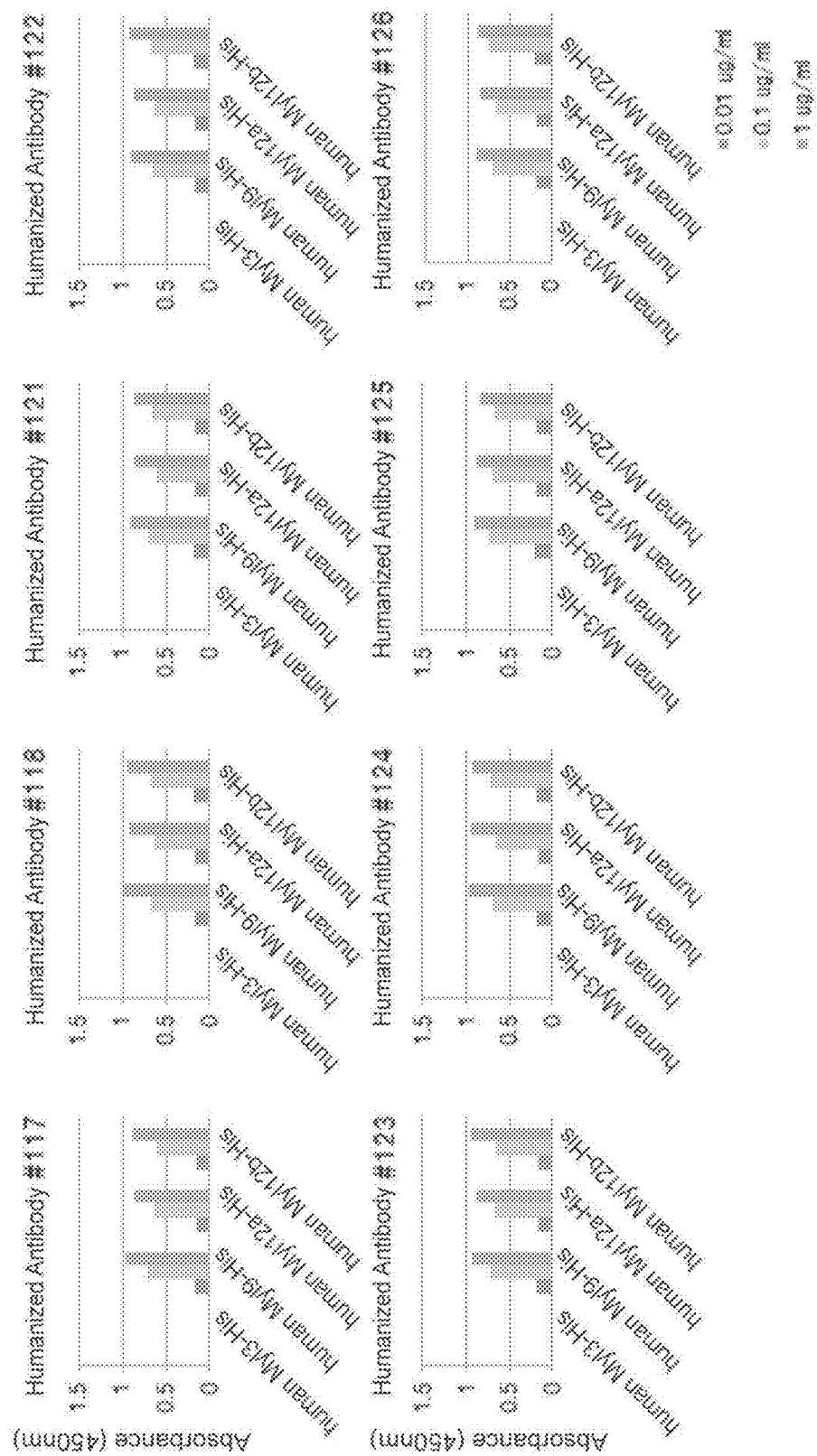
FIG. 9B shows ELISA results evaluating the binding ability of the humanized antibody prepared from Antibody A to human Myl12a and 12b.
Figure 9C:
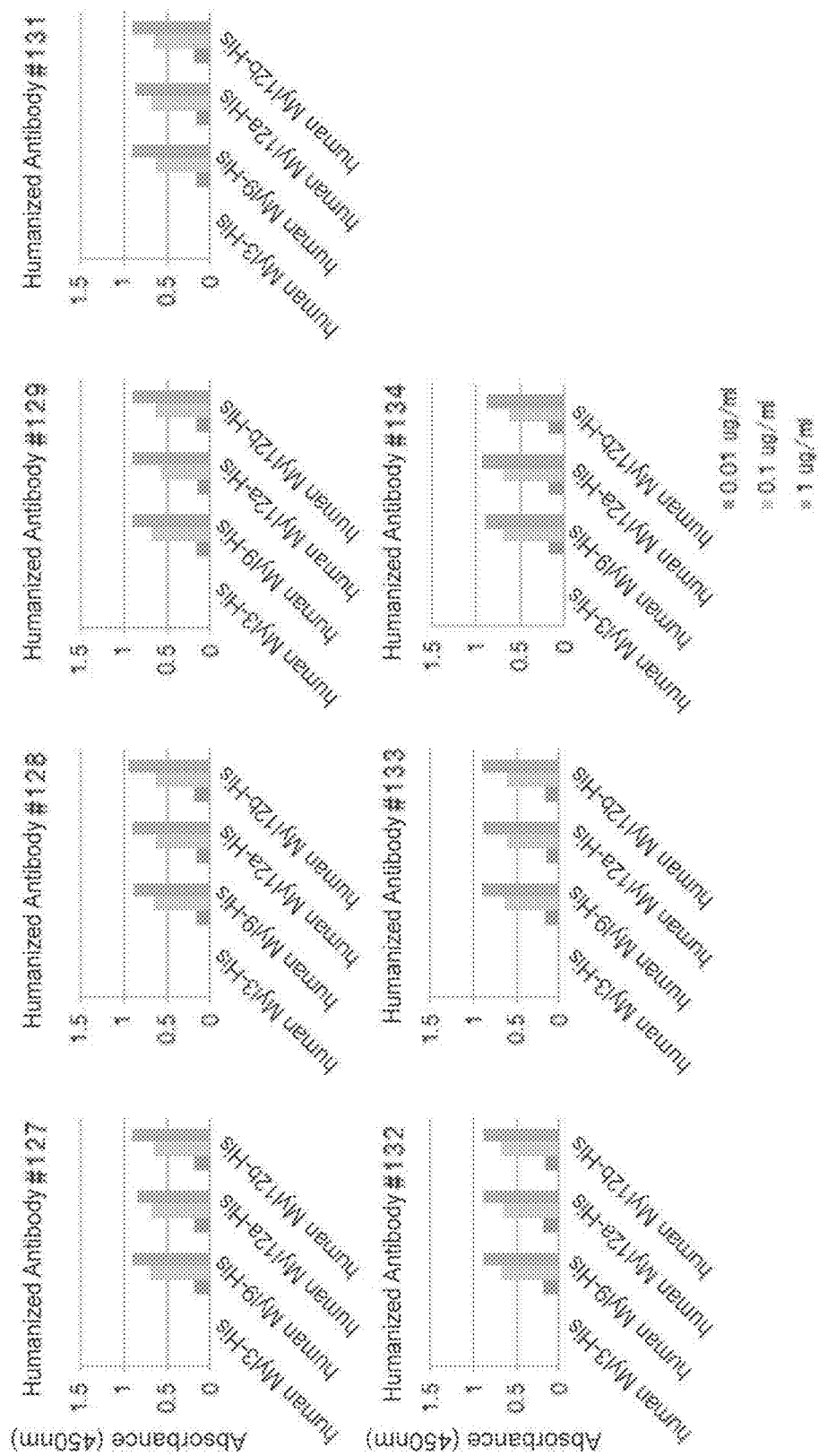
FIG. 9C shows ELISA results evaluating the binding ability of the humanized antibody prepared from Antibody A to human Myl12a and 12b.

The chimeric and humanized antibodies showed concentration-dependent binding to Myl12a and Myl12b which have high homology with human Myl9, but did not bind to human Myl3 which has low homology with human Myl9 (FIGS. 9-A to 9-C).

Figure 10:
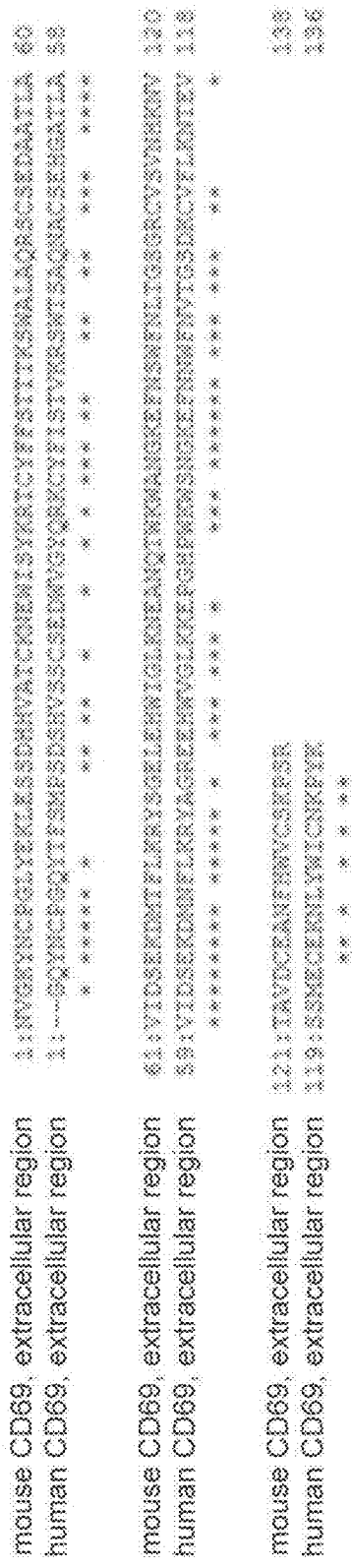
FIG. 10 shows the comparison of amino acid sequences of extracellular regions of human and mouse CD 69 (SEQ ID NO:97 and SEQ ID NO:4, respectively).

Example 6: Inhibitory Effect of Antibody A and Chimeric and Humanized Antibodies Thereof Against Binding Activity Between Human Myl9, Human Myl12a and Human Myl12b and Human CD69 Extracellular Region Protein Binding Between Human Myl9, Myl12a, and Myl12b Proteins and Human CD69 Extracellular Region Protein The binding of human Myl9, Myl12a, and Myl12b proteins and human CD69 extracellular region protein was evaluated by ELISA. A protein having a Flag tag added to the N-terminal of the extracellular region (positions 64-199, SEQ ID NO. 97) of human CD69 protein (hereinbelow 3× Flag-human CD69 EC protein) was produced following the steps below. The comparison of amino acid sequences between human and mouse CD69 protein, extracellular region (FIG. 10) are shown.

An expression plasmid comprising a gene encoding 3× Flag-human CD69 EC protein was endowed from Chiba University, and this was transfected into Expi293F cells (Invitrogen/LifeTechnologies) with ExpiFectamine 293 Transfection Kit (Thermo Fisher Scientific/Gibco). After 4 days of incubation (8% CO2, 37° C.), the culture supernatant was collected. From the collected culture supernatant, 3× Flag-human CD69 EC protein was purified with Anti-Flag M2 Affinity Gel (SIGMA). After purification, the dimerized protein was collected by using Superdex200 or Superdex75.

Evaluation of binding between human Myl9, Myl12a and Myl12b and human CD69 extracellular region protein was carried out by ELISA. Human Myl3-His, human Myl9-His, human Myl12a-His and human Myl12b-His prepared in Example 5 were coated onto the wells of a 96-well plate (Nunc), respectively. After an overnight incubation at 4° C., the wells were blocked at room temperature for one hour with 1× Block Ace (DS Pharma Biomedical Co., Ltd.). After washing three times with 0.02% Tween 20/PBS, six serial dilutions by three folds of 3× Flag-human CD69 EC protein were made from a concentration of 10 µg/mL by 50 mM NaOAc (pH 5.5)/150 mM NaCl/0.02% Tween 20 and added to the wells. After incubation at room temperature for one and half hour and washing three times with 50 mM NaOAc (pH 5.5)/150 mM NaCl/0.02% Tween 20, horseradish peroxidase-labeled anti-Flag (M2) antibody (SIGMA) was added, and this was incubated at room temperature for one hour. After washing 5 times, TMBZ (3,3',5,5'-tetramethylbenzidine) solution was added to the wells, and this was incubated for 5-20 minutes at room temperature. An equal amount of reaction quenching solution (2N $H_2SO_4$) was added to the wells, and absorbance at 450 nm was read with a microplate reader (Thermo Scientific).

Figure 11:
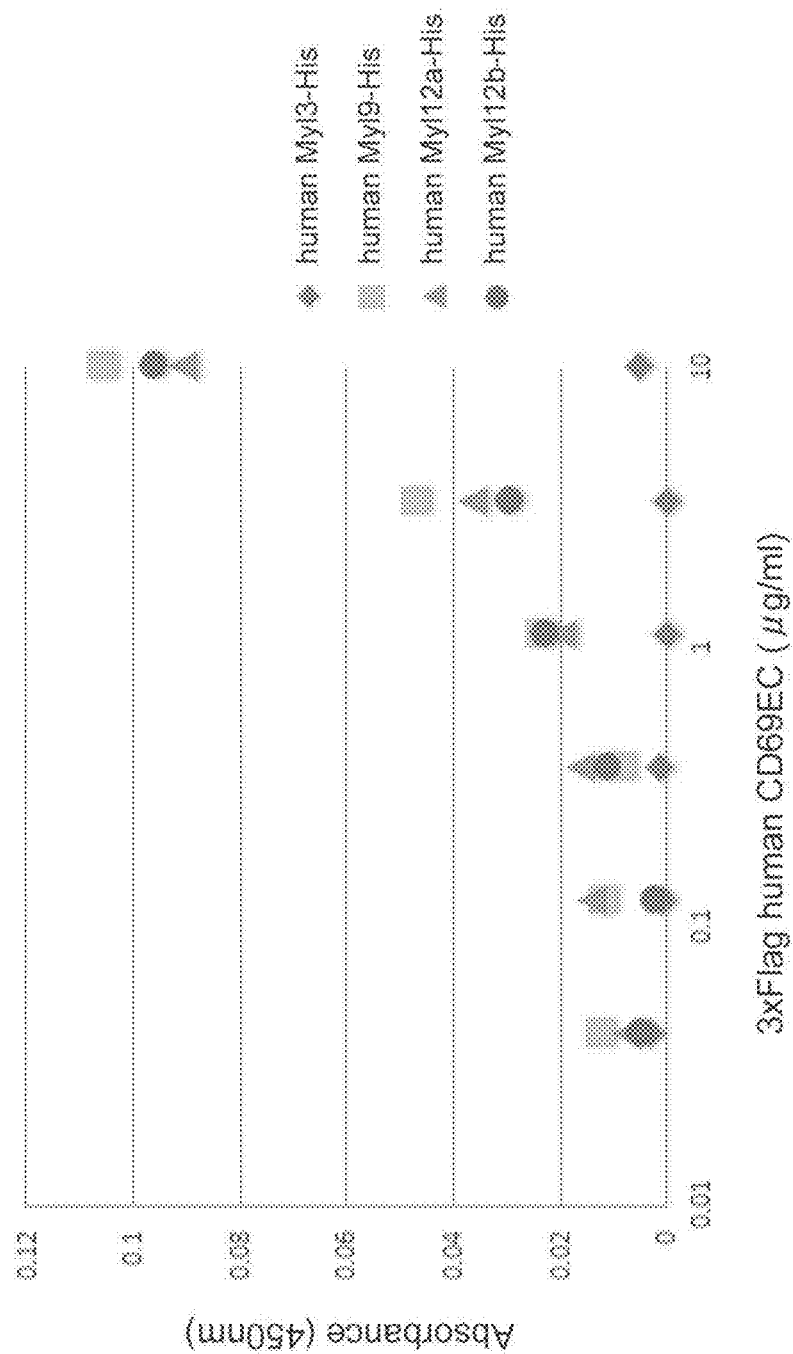
FIG. 11 shows concentration-dependent binding of the extracellular region of human CD69 to human Myl9 as well as Myl12a and 12b which have high homology with human Myl9.

The human CD69 extracellular region protein showed concentration-dependent binding to human Myl9, Myl12a and Myl12b which have high homology with human Myl9, but did not bind to human Myl3 which has low homology with human Myl9 (FIG. 11).

Evaluation of Inhibitory Activity of Antibody A Against Binding Activity of Human Myl9, Human Myl12a and Human Myl12b and Human CD69 Extracellular Region Protein Evaluation of inhibitory activity of Antibody A against binding between human Myl9, human Myl12a and human Myl12b and human CD69 extracellular region protein was carried out according to the following steps by ELISA. Human Myl9-His, human Myl12a-His and human Myl12b-His prepared in Example 5 were coated onto the wells of a 96-well plate (Nunc), respectively. After an overnight incubation at 4° C., the wells were blocked at room temperature for one hour with 1× Block Ace (DS Pharma Biomedical Co., Ltd.). After washing three times with 0.02% Tween 20/PBS, seven serial dilutions by three folds of Antibody A or control antibody (anti-dinitrophenol antibody, mouse IgG2c, κ) were made from a concentration of 30 μg/mL by 50 mM NaOAc (pH 5.5)/150 mM NaCl/0.02% Tween 20 and added to the wells. After incubation at room temperature for one hour and washing three times, 3× Flag-human CD69 EC protein were diluted to a concentration of 10 μg/mL by 50 mM NaOAc (pH 5.5)/150 mM NaCl/0.02% Tween 20 and added to the wells. After incubation at room temperature for one and half hour and washing three times with 50 mM NaOAc (pH 5.5)/150 mM NaCl/0.02% Tween 20, horseradish peroxidase-labeled anti-Flag (M2) antibody (SIGMA) was added, and this was incubated at room temperature for one hour. After washing 5 times, TMBZ (3,3',5,5'-tetramethylbenzidine) solution was added to the wells, and this was incubated for 5-20 minutes at room temperature. An equal amount of reaction quenching solution (2N $H_2SO_4$) was added to the wells, and absorbance at 450 nm was read with a microplate reader (Thermo Scientific).

Figure 12A:
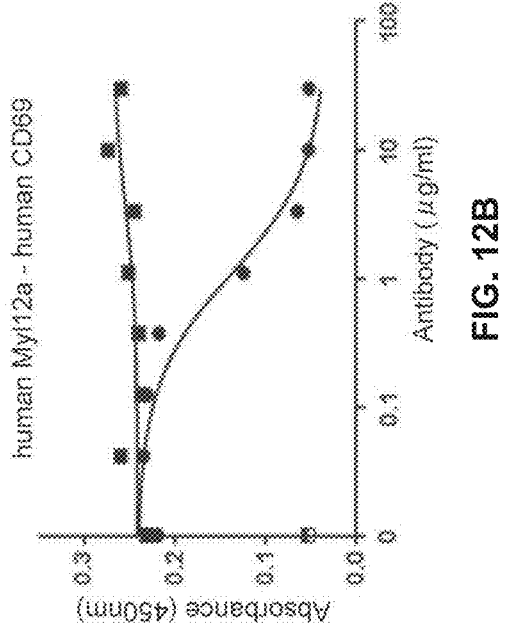
FIGS. 12A-12C show the results of concentration-dependent inhibition of Antibody A to the binding between the extracellular regions of human CD69 and human Myl9 (FIG. 12A), human Myl12a (FIG. 12B) or human Myl12b (FIG. 12C).
Figure 12B:
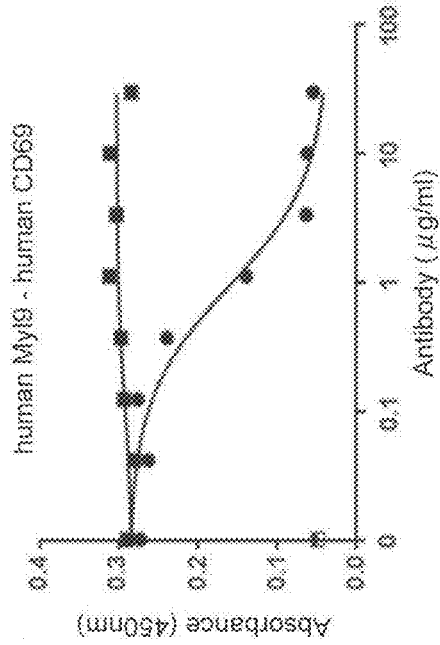
Figure 12C:
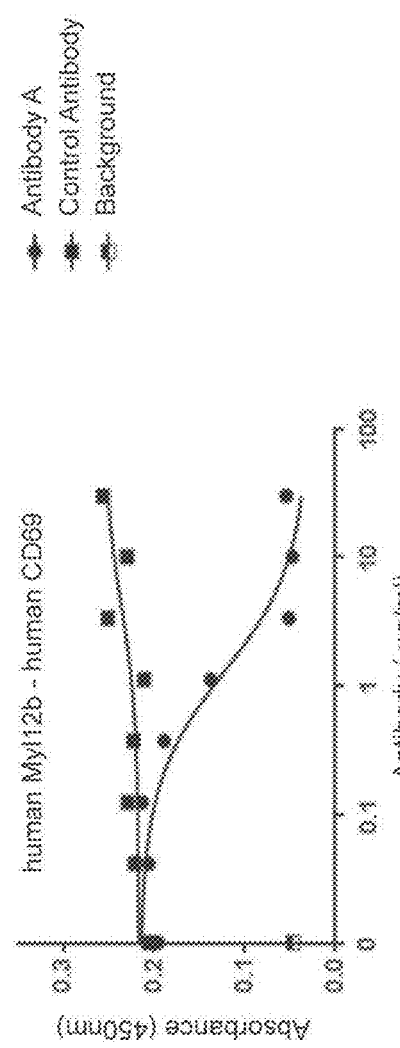
Figure 13A:
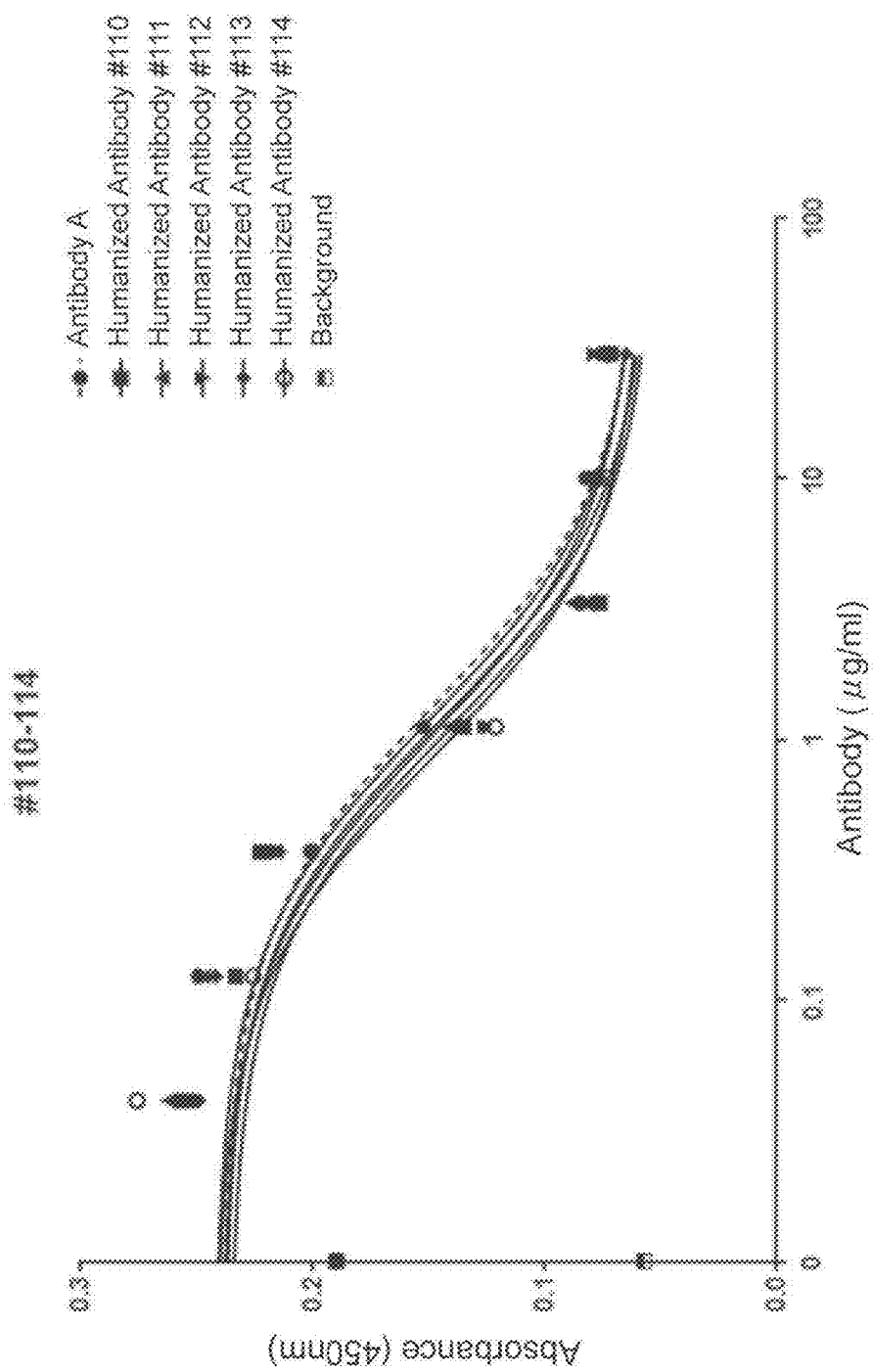
FIG. 13A shows the results of concentration-dependent inhibition of the chimeric and humanized antibodies prepared from Antibody A to the binding between human Myl9 and the extracellular region of human CD69.
Figure 13B:
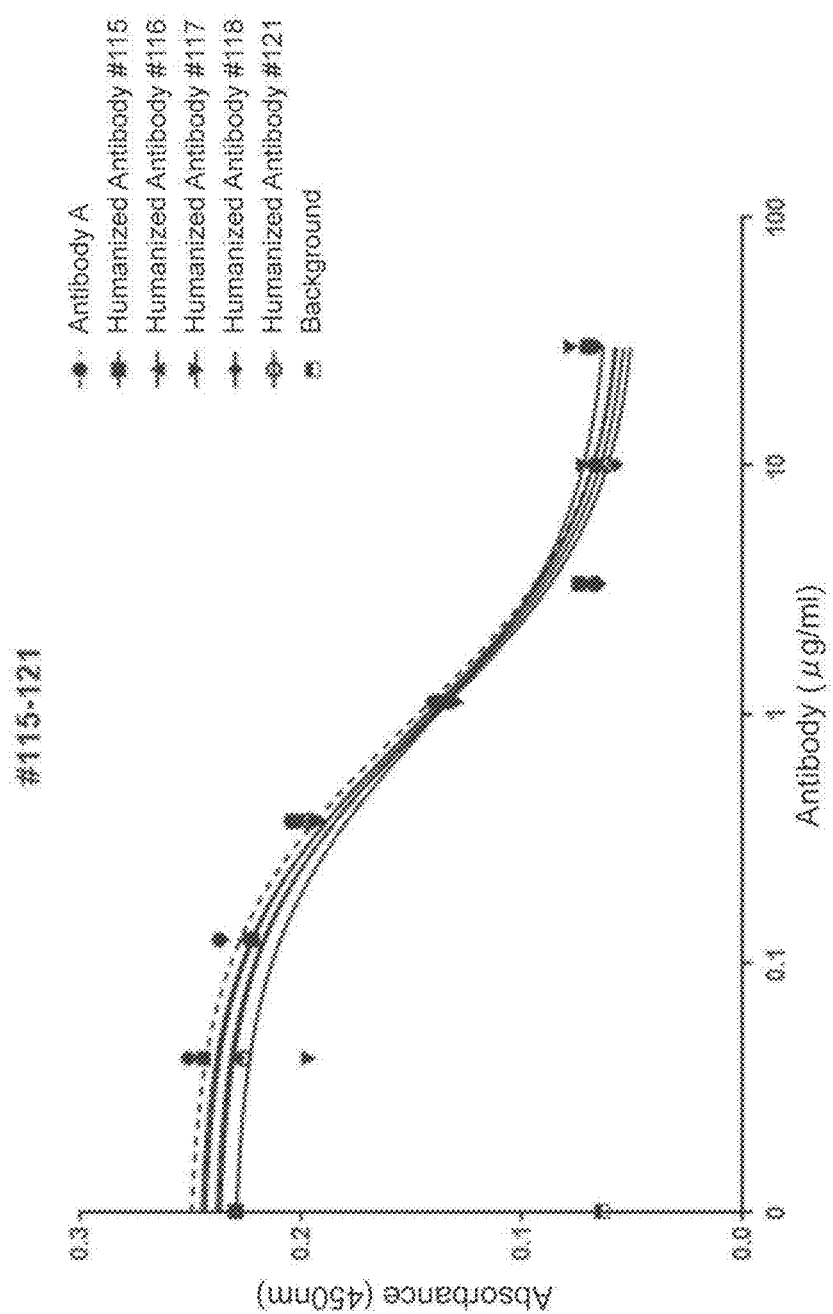
FIG. 13B is continued from FIG. 13A.
Figure 13C:
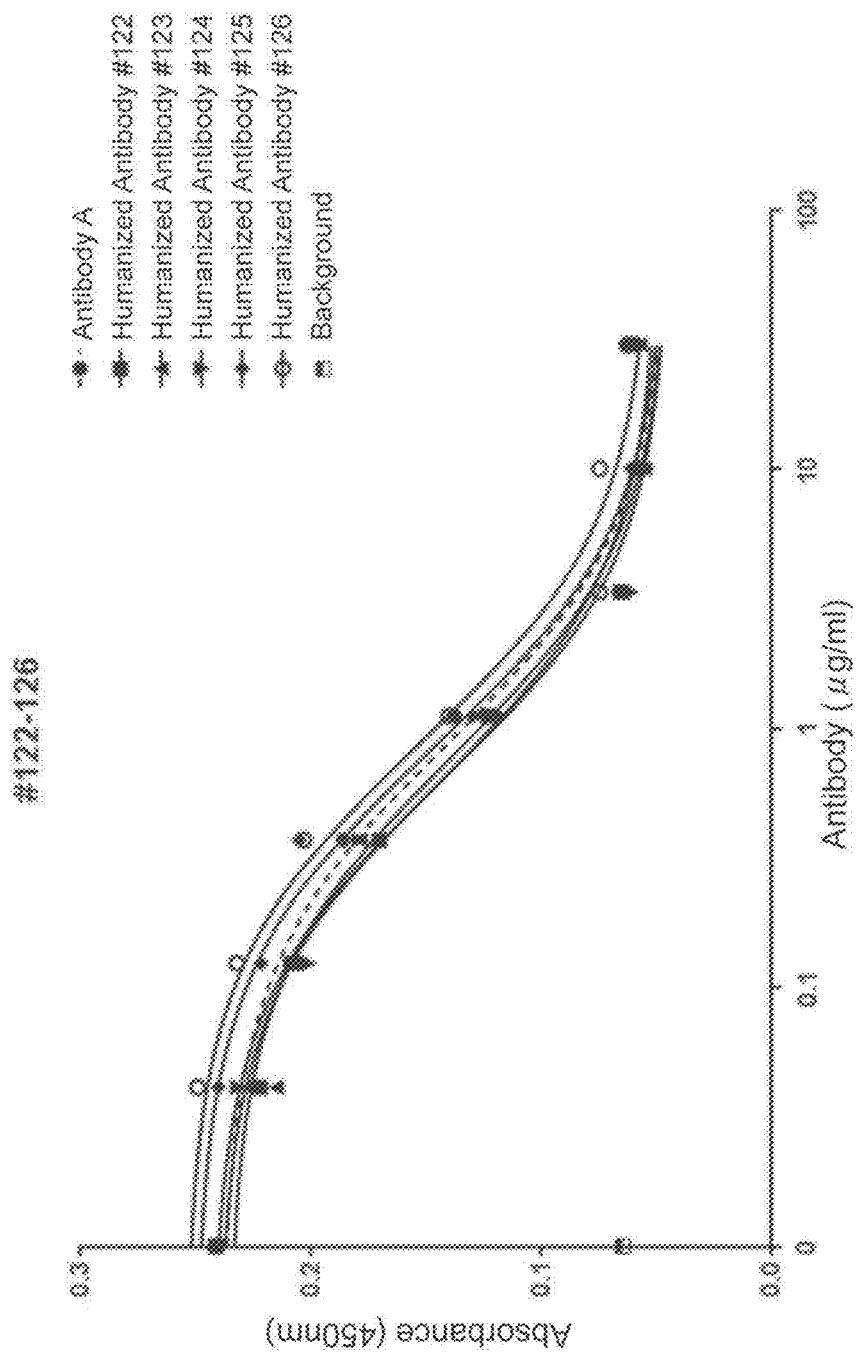
FIG. 13C is continued from FIG. 13B.
Figure 13D:
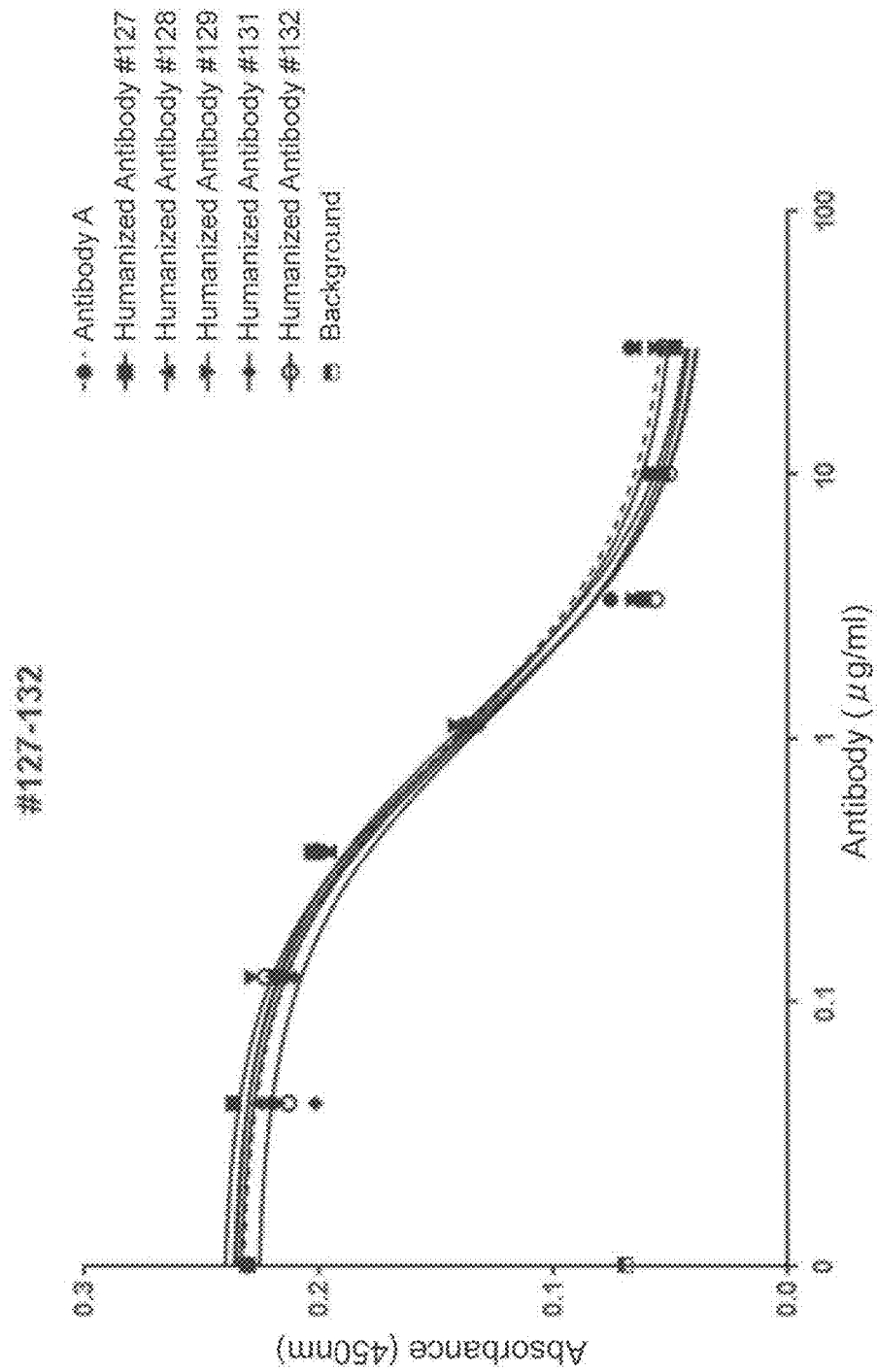
FIG. 13D is continued from FIG. 13C.
Figure 13E:
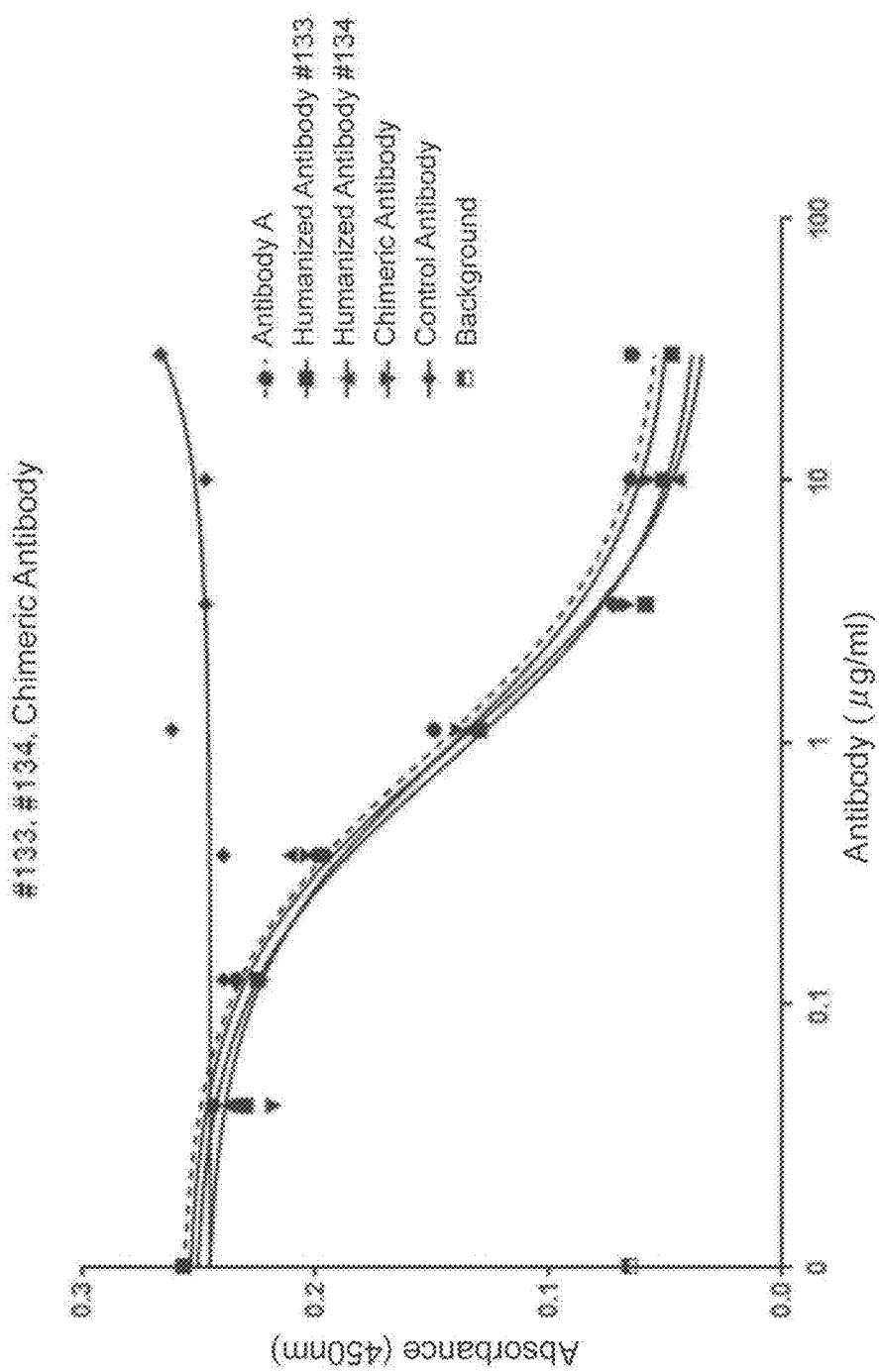
FIG. 13E is continued from FIG. 13D.
Figure 14A:
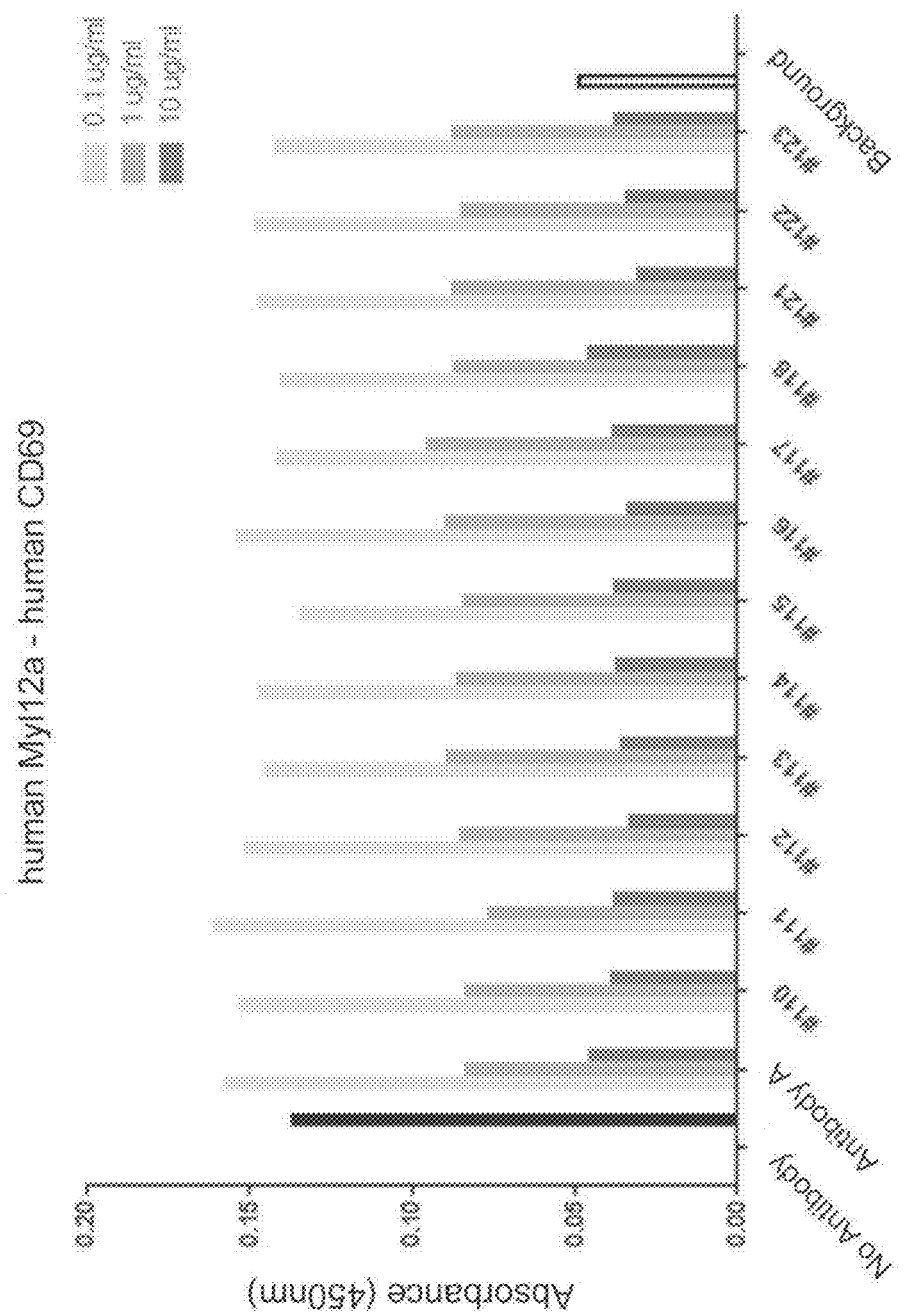
FIG. 14A shows the results of concentration-dependent inhibition of the chimeric and humanized antibodies prepared from Antibody A to the binding between human Myl12a or human Myl12b and the extracellular region of human CD69.
Figure 14B:
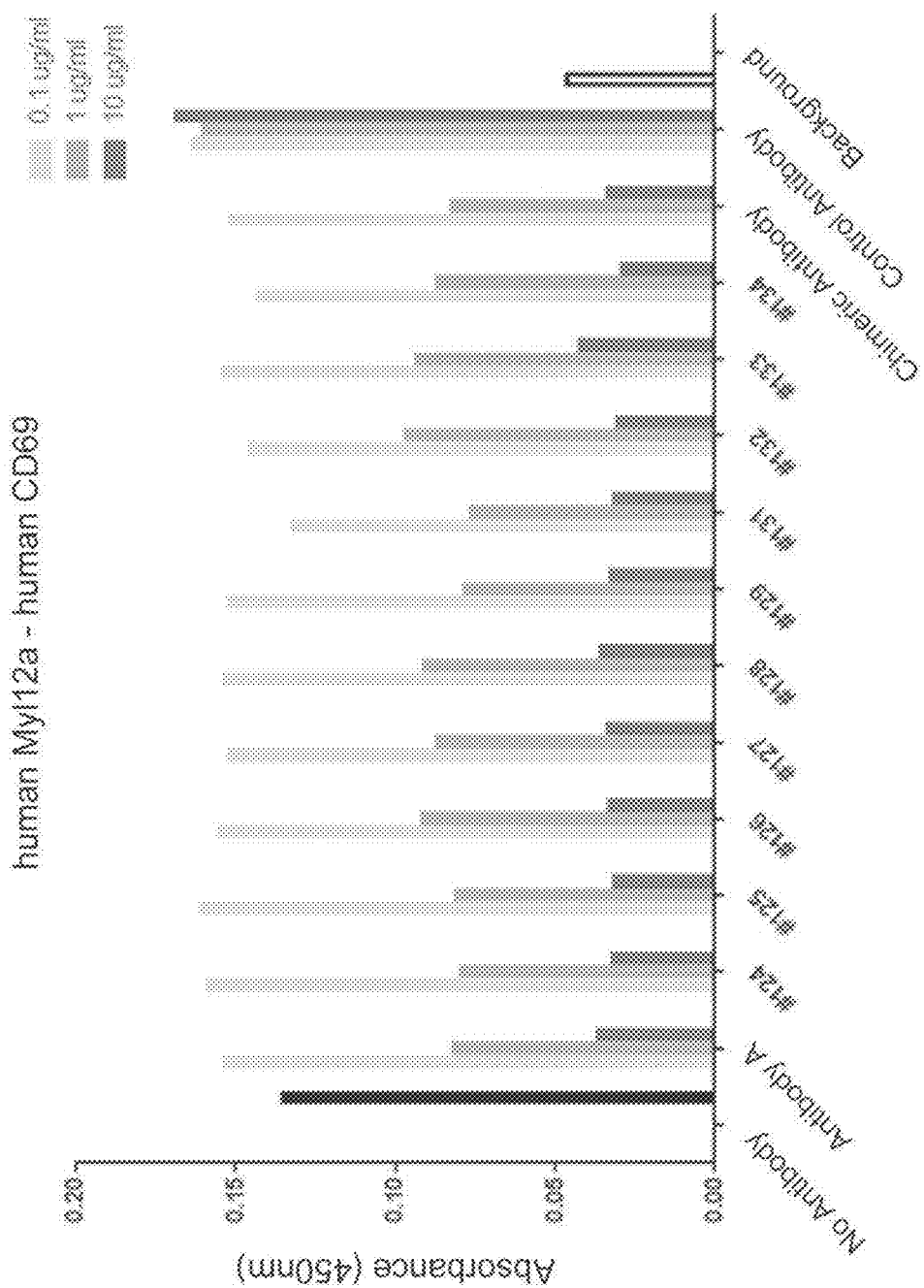
FIG. 14B is continued from FIG. 14A.
Figure 14C:
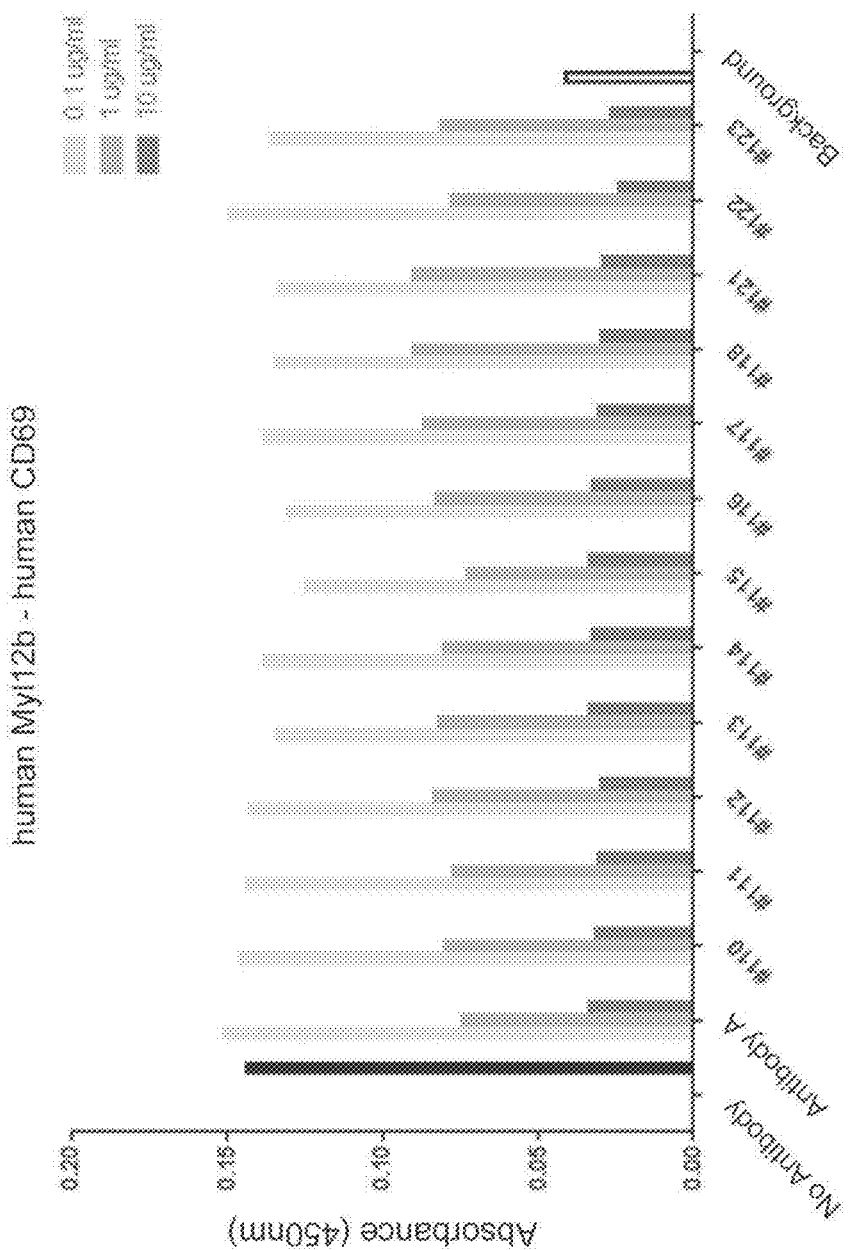
FIG. 14C is continued from FIG. 14B.
Figure 14D:
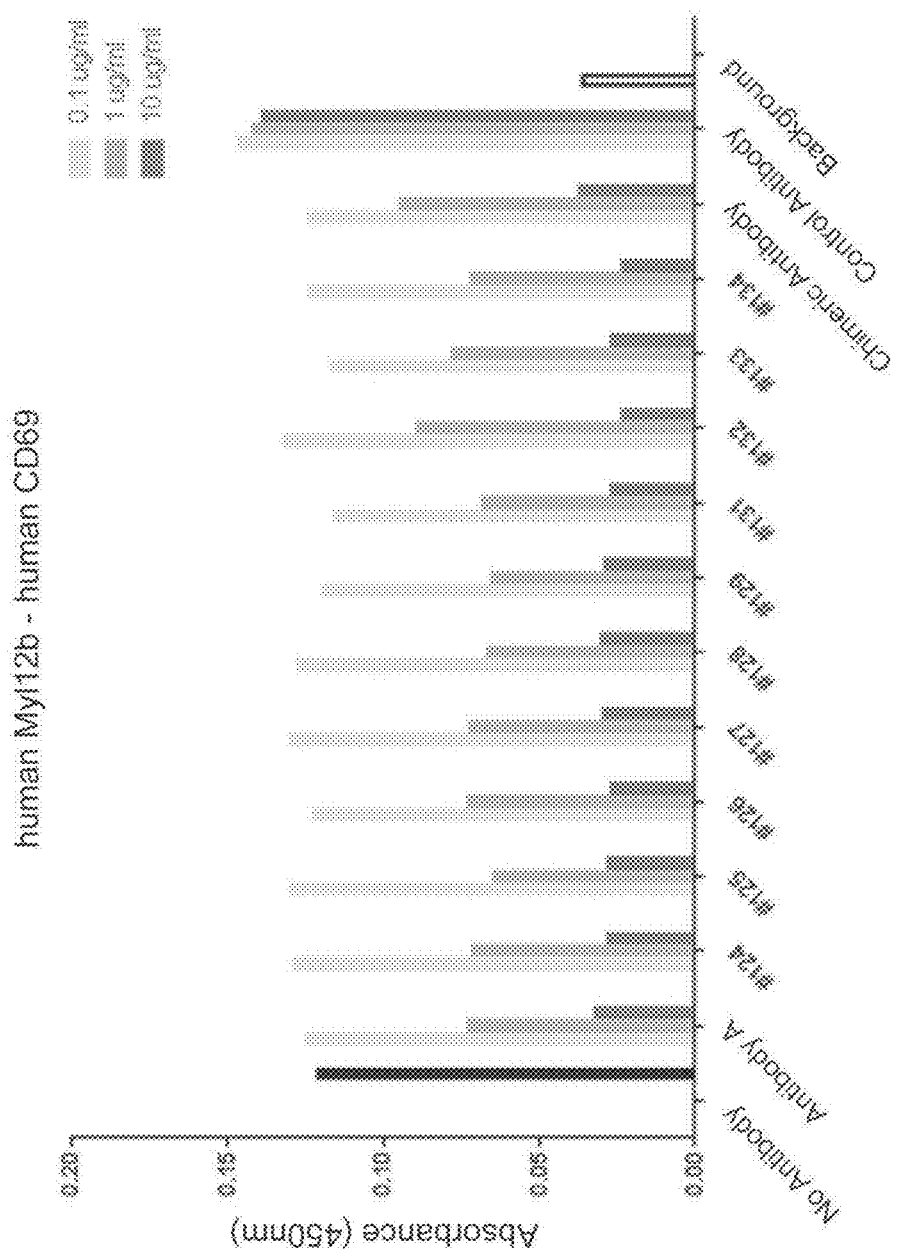
FIG. 14D is continued from FIG. 14C.

Antibody A showed concentration-dependent inhibition against the binding between human Myl9, human Myl12a and human Myl12b and human CD69 extracellular region protein (FIG. 12). The control antibody did not show inhibitory activity. The background in the figure means colorization between 3× Flag-human CD69 EC protein and horseradish peroxidase-labeled anti-Flag (M2) antibody (SIGMA) in a well on which human Myl9-His, human Myl12a-His or human Myl12b-His is not immobilized.

Evaluation of Inhibitory Activity of Chimeric and Humanized Antibodies Prepared from Antibody A Against Binding Activity of Human Myl9 and Human CD69 Extracellular Region Protein Evaluation of inhibitory activity of chimeric and humanized antibodies prepared from Antibody A against binding between human Myl9 and human CD69 extracellular region protein was carried out according to the following steps by ELISA. Human Myl9-His prepared in Example 5 were coated onto the wells of a 96-well plate (Nunc). After an overnight incubation at 4° C., the wells were blocked at room temperature for one hour with 1× Block Ace (DS Pharma. Biomedical Co., Ltd.). After washing three times with 0.02% Tween 20/PBS, seven serial dilutions by three folds of Antibody A, chimeric antibodies, humanized antibodies or control antibody (human IgG2, κ, Sigma) were made from a concentration of 30 μg/mL by 50 mM NaOAc (pH 5.5)/150 mM NaCl/0.02% Tween 20 and added to the wells. After incubation at room temperature for one hour and washing three times, 3× Flag-human CD69 EC protein were diluted to a concentration of 10 μg/mL by 50 mM NaOAc (pH 5.5)/150 mM NaCl/0.02% Tween 20 and added to the wells. After incubation at room temperature for one and half hour and washing three times with 50 mM NaOAc (pH 5.5)/150 mM NaCl/0.02% Tween 20, horseradish peroxidase-labeled anti-Flag (M2) antibody (SIGMA) was added, and this was incubated at room temperature for one hour. After washing 5 times, TMBZ (3,3',5,5'-tetramethylbenzidine) solution was added to the wells, and this was incubated for 5-20 minutes at room temperature. An equal amount of reaction quenching solution (2N $H_2SO_4$) was added to the wells, and absorbance at 450 nm was read with a microplate reader (Thermo Scientific).

Chimeric and humanized antibodies prepared from Antibody A showed concentration-dependent inhibition against the binding between human Myl9 and human CD69 extracellular region protein (FIGS. 13-1 to 13-5). The control antibody did not show inhibitory activity. The background in the figure means colorization between 3× Flag-human CD69 EC protein and horseradish peroxidase-labeled anti-Flag (M2) antibody (SIGMA) in a well on which human Myl9-His is not immobilized.

Evaluation of Inhibitory Activity of Chimeric and Humanized Antibodies Prepared from Antibody A Against Binding Activity of Human Myl12a and Human Myl12b and Human CD69 Extracellular Region Protein Evaluation of inhibitory activity of chimeric and humanized antibodies prepared from Antibody A against binding between human Myl12a and human Myl12b and human CD69 extracellular region protein was carried out according to the following steps by ELISA. Human Myl12a-His and Myl12b-His prepared in Example 5 were coated onto the wells of a 96-well plate (Nunc), respectively. After an overnight incubation at 4° C., the wells were blocked at room temperature for one hour with 1× Block Ace (DS Pharma Biomedical Co., Ltd.). After washing three times with 0.02% Tween 20/PBS, Antibody A, chimeric antibody, humanized antibodies or control antibody (human IgG2, κ, Sigma) were diluted to concentrations of 0.1, 1 and 10 μg/mL by 50 mM NaOAc (pH 5.5)/150 mM NaCl/0.02% Tween 20 and added to the wells. After incubation at room temperature for one hour and washing three times, 3× Flag-human CD69 EC protein were diluted to a concentration of 10 μg/mL by 50 mM NaOAc (pH 5.5)/150 mM NaCl/0.02% Tween 20 and added to the wells. After incubation at room temperature for one and half hour and washing three times with 50 mM NaOAc (pH 5.5)/150 mM NaCl/0.02% Tween 20, horseradish peroxidase-labeled anti-Flag (M2) antibody (SIGMA) was added, and this was incubated at room temperature for one hour. After washing 5 times, TMBZ (3,3',5,5'-tetramethylbenzidine) solution was added to the wells, and this was incubated for 5-20 minutes at room temperature. An equal amount of reaction quenching solution (2N $H_2SO_4$) was added to the wells, and absorbance at 450 nm was read with a microplate reader (Thermo Scientific).

Chimeric and humanized antibodies prepared from Antibody A showed concentration-dependent inhibition against the binding between human Myl12a and Myl12b and human CD69 extracellular region protein (FIGS. 14-1 to 14-4). The control antibody did not show inhibitory activity. The background in the figure means colorization between 3× Flag-human CD69 EC protein and horseradish peroxidase-labeled anti-Flag (M2) antibody (SIGMA) in a well on which human Myl12a-His or human Myl12b-His is not immobilized.

Example 7: Anti-Tumor Effect of Combination Administration of Antibody A and Anti-PD-1 Antibody Mouse colorectal cancer cell line CT26.WT (ATCC No. CRT-2638) cultured in RPMI1640 culture media containing 10% PBS and penicillin/streptomycin, was suspended in a phosphate buffered saline to obtain a cell suspension of a concentration of $1 \times 10^7$ cells/mL. The cell suspension was transplanted subcutaneously in the right back region of 6-week-old mice (BALB/c, female, Charles River Laboratories Japan, Inc.) at a dose of 0.1 mL. Six days after the transplantation, the longest diameter and the short axis of the tumor were measured with an electronic digital caliper (Digimatic™ Caliper, Mitutoyo Corporation). The tumor volume was calculated by the following calculation formula.

$$\text{Tumor volume (mm}^3\text{)} = \text{longest diameter (mm)} \times \text{short axis (mm)} \times \text{short axis (mm)}/2$$

Figure 15:
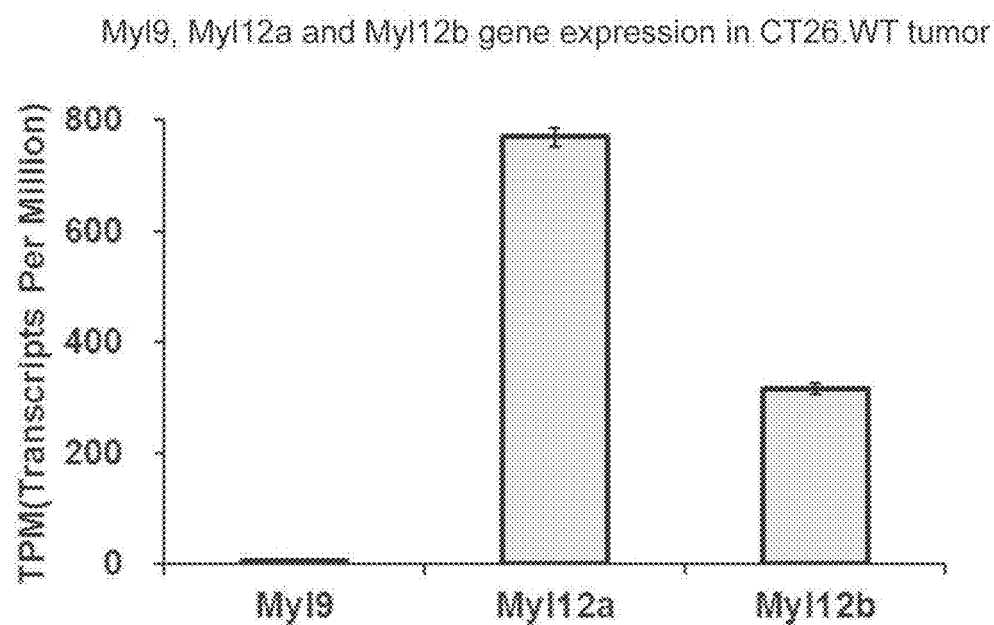
FIG. 15 shows the results of the analysis of expression of Myl9, Myl12a and Myl12b in subcutaneous tumor tissue in mouse colorectal cancer cell line CT26.WT.
Figure 16B:
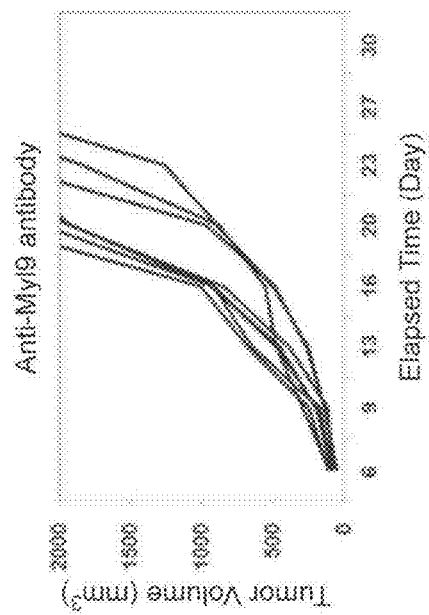
FIGS. 16A-16D show inhibition of tumor growth in control group (FIG. 16A), Antibody A alone administration group (FIG. 16B), anti PD-1 antibody alone administration group (FIG. 16C) and combination of Antibody A and anti PD-1 antibody administration group (FIG. 16D) in mouse colorectal cancer cell line CT26.WT subcutaneous transplantation models.
Figure 16D:
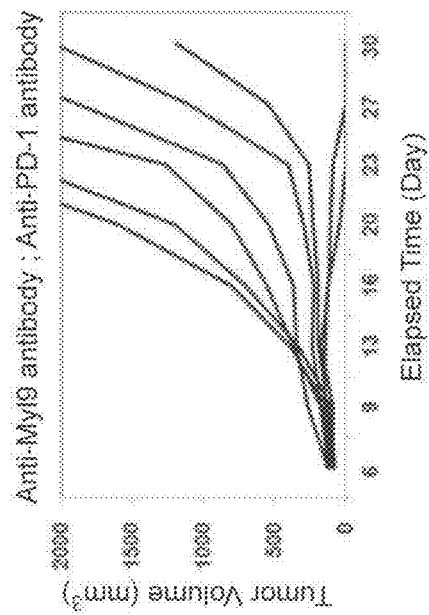
Figure 16A:
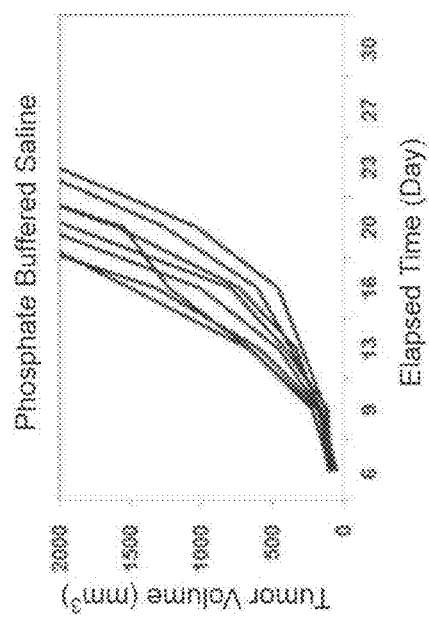
Figure 16C:
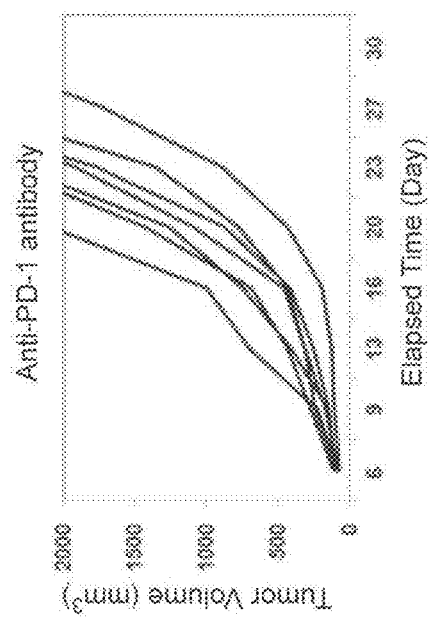

FIG. 15 shows the results of gene expression analysis of subcutaneous tumor tissue of mouse colorectal cancer cell line CT26.WT. Nucleic acid was extracted from tumor tissue derived from CT26.WT by TRIzol (Registered Trademark) Reagent (Thermo Fisher Scientific) and total RNA was prepared by Rneasy mini kit (Qiagen). From the total RNA a library was prepared by SureSelect Strand Specific RNA library preparation kit (Agilent Technologies) for RNASeq analysis and sequencing was performed by HiSeq4000 (illumine). Fastq files obtained by the sequencing were normalized by TPM (Transcript Per Million) method and the expression of Myl9, Myl12a and Myl12b were measured. The expression of Myl9 was low and the expressions of Myl12a and Myl12b were high in the tumor tissue.

The mice were divided into groups so that the average value of the tumor volume of each group was almost equal based on the tumor volume of the first day of the administration. Antibody A and the anti-PD-1 antibody (BoXCell, Catalog #: BE0146) were prepared to a solution of 2 mg/mL by a phosphate buffered saline and were intraperitoneally administered to mice at a dose of 0.1 mL/mouse at twice per seven days, four times in total (Days 6, 9, 13 and 16 after the cancer cell transplantation). In the control group, a phosphate buffered saline was intraperitoneally administered to mice at a dose of 0.2 mi./mouse at twice per seven days, four times in total (Days 6, 9, 13 and 16 after the cancer cell transplantation). Each group had 7-8 mice.

FIG. 16 shows the changes with the passage of days of the calculated tumor volumes in control group (A), Antibody A administration group (B), anti-PD-1 antibody administration group (C) and combination of Antibody A and anti-PD-1 antibody administration group (D) to the last days of the test (Day 30). As shown in FIG. 16B, Antibody A alone did not almost inhibit the growth of tumor. Anti-PD-1 antibody alone slightly inhibited the growth of tumor compared to control group (FIG. 16C). The combination administration of Antibody A and anti-PD-1 antibody significantly inhibited the growth of tumor and tumor-disappeared mice (2/10) were confirmed (FIG. 16D). The above results suggest synergistic effect by the combination administration of Antibody A and anti-PD-1 antibody.

INDUSTRIAL APPLICABILITY

An anti-Myl9 antibody or a Myl9 binding fragment thereof that binds to Myl9 and may inhibit the interaction between Myl9 and CD69, as well as a pharmaceutical composition comprising the same may be provided. The antibody or pharmaceutical composition according to the present invention may be useful for treating a disease attributed to the interaction between Myl9 and CD69, e.g. allergic airway inflammation such as asthma, chronic allergic rhinitis, or some sinusitis, airway inflammation disease such as sinusitis not included in allergic airway inflammation, and inflammatory bowel disease such as ulcerative colitis, Crohn's disease, Behcet's disease, and eosinophilic gastrointestinal dysfunction. The antibody according to the present invention may also inhibit the interaction between Myl12 and CD69. Accordingly the antibody or the pharmaceutical composition according to the present invention may be useful for treating a disease associated with the interaction between Myl9 and/or Myl12 and CD69, e.g. tumor such as colorectal cancer, malignant melanoma, non-small cell lung cancer, renal cell carcinoma, malignant lymphoma, multiple myeloma, head and neck cancer, urothelial cancer, breast cancer, hepatocellular carcinoma, gastric cancer, esophageal cancer, ovarian cancer, small cell lung cancer, mesothelioma and endometrial cancer when it is in combination with an immune checkpoint inhibitor.

---

The invention claimed is:

1. An anti-myosin regulatory light chain polypeptide (Myl)9 antibody or a Myl9 binding fragment thereof comprising:
   (a) a heavy chain CDR1 consisting of a peptide represented by the amino acid sequence set forth in SEQ ID NO. 28;
   (b) a heavy chain CDR2 consisting of a peptide represented by the amino acid sequence set forth in SEQ ID NO. 30;
   (c) a heavy chain CDR3 consisting of a peptide represented by the amino acid sequence set forth in SEQ ID NO. 32;
   (d) a light chain CDR1 consisting of a peptide represented by the amino acid sequence set forth in SEQ ID NO. 33;
   (e) a light chain CDR2 consisting of a peptide represented by the amino acid sequence set forth in SEQ ID NO. 34; and
   (f) a light chain CDR3 consisting of a peptide represented by the amino acid sequence set forth in SEQ ID NO. 35.

2. The anti-Myl9 antibody or Myl9 binding fragment thereof according to claim 1, wherein said antibody is a humanized or chimeric antibody.

3. The anti-Myl9 antibody or Myl9 binding fragment thereof according to claim 1, wherein said Myl9 is human Myl9.

4. The anti-Myl9 antibody or Myl9 binding fragment thereof according to claim 1 that inhibits the interaction between Myl9 and CD69, wherein
   said antibody comprises a heavy chain and a light chain,
   the variable region of said heavy chain comprises a peptide represented by the amino acid sequence set forth in SEQ ID NOs. 55, 56, 57, 58, 59, 60, 61, 62, 63, or 64, and
   the variable region of said light chain comprises a peptide represented by the amino acid sequence set forth in SEQ ID NOs. 65, 66, 67, or 68.

5. The anti-Myl9 antibody or Myl9 binding fragment thereof according to claim 1, wherein said antibody is selected from the group consisting of the following antibodies:
   (1) an antibody comprising a heavy chain variable region comprising a peptide represented by the amino acid sequence set forth in SEQ ID NO. 64 and a light chain variable region comprising a peptide represented by the amino acid sequence set forth in SEQ ID NO. 66;
   (2) an antibody comprising a heavy chain variable region comprising a peptide represented by the amino acid sequence set forth in SEQ ID NO. 63 and a light chain variable region comprising a peptide represented by the amino acid sequence set forth in SEQ ID NO. 66;
   (3) an antibody comprising a heavy chain variable region comprising a peptide represented by the amino acid sequence set forth in SEQ ID NO. 56 and a light chain variable region comprising a peptide represented by the amino acid sequence set forth in SEQ ID NO. 66;
   (4) an antibody comprising a heavy chain variable region comprising a peptide represented by the amino acid sequence set forth in SEQ ID NO. 57 and a light chain variable region comprising a peptide represented by the amino acid sequence set forth in SEQ ID NO. 66;
   (5) an antibody comprising a heavy chain variable region comprising a peptide represented by the amino acid sequence set forth in SEQ ID NO. 55 and a light chain variable region comprising a peptide represented by the amino acid sequence set forth in SEQ ID NO. 66;
   (6) an antibody comprising a heavy chain variable region comprising a peptide represented by the amino acid sequence set forth in SEQ ID NO. 58 and a light chain variable region comprising a peptide represented by the amino acid sequence set forth in SEQ ID NO. 66;
   (7) an antibody comprising a heavy chain variable region comprising a peptide represented by the amino acid sequence set forth in SEQ ID NO. 59 and a light chain variable region comprising a peptide represented by the amino acid sequence set forth in SEQ ID NO. 66;
   (8) an antibody comprising a heavy chain variable region comprising a peptide represented by the amino acid sequence set forth in SEQ ID NO. 60 and a light chain variable region comprising a peptide represented by the amino acid sequence set forth in SEQ ID NO. 66;
   (9) an antibody comprising a heavy chain variable region comprising a peptide represented by the amino acid sequence set forth in SEQ ID NO. 61 and a light chain variable region comprising a peptide represented by the amino acid sequence set forth in SEQ ID NO. 66;
   (10) an antibody comprising a heavy chain variable region comprising a peptide represented by the amino acid sequence set forth in SEQ ID NO. 64 and a light chain variable region comprising a peptide represented by the amino acid sequence set forth in SEQ ID NO. 68;
   (11) an antibody comprising a heavy chain variable region comprising a peptide represented by the amino acid sequence set forth in SEQ ID NO. 63 and a light chain variable region comprising a peptide represented by the amino acid sequence set forth in SEQ ID NO. 68;
   (12) an antibody comprising a heavy chain variable region comprising a peptide represented by the amino acid sequence set forth in SEQ ID NO. 56 and a light chain variable region comprising a peptide represented by the amino acid sequence set forth in SEQ ID NO. 68;
   (13) an antibody comprising a heavy chain variable region comprising a peptide represented by the amino acid sequence set forth in SEQ ID NO. 57 and a light chain variable region comprising a peptide represented by the amino acid sequence set forth in SEQ ID NO. 68;
   (14) an antibody comprising a heavy chain variable region comprising a peptide represented by the amino acid sequence set forth in SEQ ID NO. 55 and a light chain variable region comprising a peptide represented by the amino acid sequence set forth in SEQ ID NO. 68;
   (15) an antibody comprising a heavy chain variable region comprising a peptide represented by the amino acid sequence set forth in SEQ ID NO. 58 and a light chain variable region comprising a peptide represented by the amino acid sequence set forth in SEQ ID NO. 68;

(16) an antibody comprising a heavy chain variable region comprising a peptide represented by the amino acid sequence set forth in SEQ ID NO. 59 and a light chain variable region comprising a peptide represented by the amino acid sequence set forth in SEQ ID NO. 68;

(17) an antibody comprising a heavy chain variable region comprising a peptide represented by the amino acid sequence set forth in SEQ ID NO. 60 and a light chain variable region comprising a peptide represented by the amino acid sequence set forth in SEQ ID NO. 68;

(18) an antibody comprising a heavy chain variable region comprising a peptide represented by the amino acid sequence set forth in SEQ ID NO. 61 and a light chain variable region comprising a peptide represented by the amino acid sequence set forth in SEQ ID NO. 68;

(19) an antibody comprising a heavy chain variable region comprising a peptide represented by the amino acid sequence set forth in SEQ ID NO. 62 and a light chain variable region comprising a peptide represented by the amino acid sequence set forth in SEQ ID NO. 65;

(20) an antibody comprising a heavy chain variable region comprising a peptide represented by the amino acid sequence set forth in SEQ ID NO. 62 and a light chain variable region comprising a peptide represented by the amino acid sequence set forth in SEQ ID NO. 67;

(21) an antibody comprising a heavy chain variable region comprising a peptide represented by the amino acid sequence set forth in SEQ ID NO. 62 and a light chain variable region comprising a peptide represented by the amino acid sequence set forth in SEQ ID NO. 66; and

(22) an antibody comprising a heavy chain variable region comprising a peptide represented by the amino acid sequence set forth in SEQ ID NO. 62 and a light chain variable region comprising a peptide represented by the amino acid sequence set forth in SEQ ID NO. 68.

6. The anti-Myl9 antibody or Myl9 binding fragment thereof according to claim 1 that comprises heavy and light chains, wherein the constant region of said heavy chain is IgG.

7. The anti-Myl9 antibody or Myl9 binding fragment thereof according to claim 6, wherein the constant region of said heavy chain is the constant region of human IgG2.

8. The anti-Myl9 antibody or Myl9 binding fragment thereof according to claim 7, wherein said constant region of human IgG2 possesses mutations V234A and G237A.

9. The anti-Myl9 antibody or Myl9 binding fragment thereof according to claim 7, wherein said constant region has the C-terminal lysine residue deletion.

10. The anti-Myl9 antibody or Myl9 binding fragment thereof according to claim 6, wherein the constant region of said light chain comprises the constant region of human Igκ.

11. The anti-Myl9 antibody or Myl9 binding fragment thereof according to claim 1, wherein said antibody or Myl9 binding fragment thereof inhibits the interaction between Myl12a or Myl12b and CD69.

12. A pharmaceutical composition comprising the antibody or Myl9 binding fragment thereof according to claim 1, and a pharmaceutically acceptable carrier or additive.

13. A method of treating allergic airway inflammation or an inflammatory bowel disease in a human subject in need thereof, the method comprising administering to the human subject an effective amount of the pharmaceutical composition according to claim 12.

14. The method according to claim 13, wherein the inflammatory bowel disease is ulcerative colitis or Crohn's disease.

15. A method of treating a colorectal cancer in a human subject in need thereof, the method comprising administering to the human subject an effective amount of the pharmaceutical composition according to claim 12, wherein the pharmaceutical composition is administered in combination with an immune checkpoint inhibitor.

16. The method according to claim 15, wherein the immune checkpoint inhibitor is a PD-1 inhibitor.

17. The method according to claim 16, wherein the PD-1 inhibitor is an anti-PD-1 antibody or an anti-PD-L1 antibody.

18. The method according to claim 16, wherein the PD-1 inhibitor is an anti-PD-1 antibody.

19. An anti-Myl9 antibody or a Myl9 binding fragment thereof comprising a heavy chain variable region comprising the amino acid sequence set forth in SEQ ID NO:64 and a light chain variable region comprising the amino acid sequence set forth in SEQ ID NO:68.

20. An anti-Myl9 antibody or a Myl9 binding fragment thereof comprising a heavy chain variable region comprising the amino acid sequence set forth in SEQ ID NO:63 and a light chain variable region comprising the amino acid sequence set forth in SEQ ID NO:68.

21. An anti-Myl9 antibody or a Myl9 binding fragment thereof comprising a heavy chain variable region comprising the amino acid sequence set forth in SEQ ID NO:56 and a light chain variable region comprising the amino acid sequence set forth in SEQ ID NO:68.

22. An anti-Myl9 antibody or a Myl9 binding fragment thereof comprising a heavy chain variable region comprising the amino acid sequence set forth in SEQ ID NO:57 and a light chain variable region comprising the amino acid sequence set forth in SEQ ID NO:68.

23. An anti-Myl9 antibody or a Myl9 binding fragment thereof comprising a heavy chain variable region comprising the amino acid sequence set forth in SEQ ID NO:55 and a light chain variable region comprising the amino acid sequence set forth in SEQ ID NO:68.

24. An anti-Myl9 antibody or a Myl9 binding fragment thereof comprising a heavy chain variable region comprising the amino acid sequence set forth in SEQ ID NO:58 and a light chain variable region comprising the amino acid sequence set forth in SEQ ID NO:68.

25. An anti-Myl9 antibody or a Myl9 binding fragment thereof comprising a heavy chain variable region comprising the amino acid sequence set forth in SEQ ID NO:59 and a light chain variable region comprising the amino acid sequence set forth in SEQ ID NO:68.

26. An anti-Myl9 antibody or a Myl9 binding fragment thereof comprising a heavy chain variable region comprising the amino acid sequence set forth in SEQ ID NO:60 and a light chain variable region comprising the amino acid sequence set forth in SEQ ID NO:68.

27. An anti-Myl9 antibody or a Myl9 binding fragment thereof comprising a heavy chain variable region comprising the amino acid sequence set forth in SEQ ID NO:61 and a light chain variable region comprising the amino acid sequence set forth in SEQ ID NO:68.

28. An anti-Myl9 antibody or a Myl9 binding fragment thereof comprising a heavy chain variable region comprising the amino acid sequence set forth in SEQ ID NO:62 and a light chain variable region comprising the amino acid sequence set forth in SEQ ID NO:65.

29. An anti-Myl9 antibody or a Myl9 binding fragment thereof comprising a heavy chain variable region comprising the amino acid sequence set forth in SEQ ID NO:62 and a light chain variable region comprising the amino acid sequence set forth in SEQ ID NO:67.

30. An anti-Myl9 antibody or a Myl9 binding fragment thereof comprising a heavy chain variable region comprising the amino acid sequence set forth in SEQ ID NO:62 and a light chain variable region comprising the amino acid sequence set forth in SEQ ID NO:66.

31. An anti-Myl9 antibody or a Myl9 binding fragment thereof comprising a heavy chain variable region comprising the amino acid sequence set forth in SEQ ID NO:62 and a light chain variable region comprising the amino acid sequence set forth in SEQ ID NO:68.

* * * * *